US010626415B2

(12) United States Patent
Vandenberghe et al.

(10) Patent No.: US 10,626,415 B2
(45) Date of Patent: Apr. 21, 2020

(54) METHOD OF INCREASING THE FUNCTION OF AN AAV VECTOR

(71) Applicant: THE TRUSTEES OF THE UNIVERSITY OF PENNSYLVANIA, Philadelphia, PA (US)

(72) Inventors: Luk Vandenberghe, Weston, MA (US); Guangping Gao, Westborough, MA (US); James M. Wilson, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 152 days.

(21) Appl. No.: 15/796,115

(22) Filed: Oct. 27, 2017

(65) Prior Publication Data

US 2018/0057841 A1 Mar. 1, 2018

Related U.S. Application Data

(60) Continuation of application No. 15/408,567, filed on Jan. 18, 2017, now abandoned, which is a continuation of application No. 14/624,671, filed on Feb. 18, 2015, now Pat. No. 10,301,648, which is a division of application No. 11/887,679, filed as application No. PCT/US2006/013375 on Apr. 7, 2006, now Pat. No. 8,999,678.

(60) Provisional application No. 60/733,497, filed on Nov. 4, 2005, provisional application No. 60/669,083, filed on Apr. 7, 2005.

(51) Int. Cl.
*C12N 15/86* (2006.01)
*A61K 48/00* (2006.01)
*C07K 14/005* (2006.01)
*C12N 7/00* (2006.01)

(52) U.S. Cl.
CPC ............ *C12N 15/86* (2013.01); *A61K 48/005* (2013.01); *A61K 48/0091* (2013.01); *C07K 14/005* (2013.01); *C12N 7/00* (2013.01); *A61K 48/00* (2013.01); *C12N 2750/14122* (2013.01); *C12N 2750/14142* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| 6,156,303 | A | 12/2000 | Russell et al. |
|---|---|---|---|
| 6,703,237 | B2 | 3/2004 | Samulski et al. |
| 6,962,815 | B2 | 11/2005 | Bartlett |
| 7,252,997 | B1 | 8/2007 | Halleck et al. |
| 7,314,912 | B1 | 1/2008 | Halleck et al. |
| 2003/0138772 | A1 | 7/2003 | Gao et al. |
| 2004/0170611 | A1 | 9/2004 | Morgan et al. |
| 2007/0036760 | A1 | 2/2007 | Wilson et al. |
| 2009/0275107 | A1 | 11/2009 | Lock |
| 2009/0317417 | A1 | 12/2009 | Vandenberghe |
| 2012/0322861 | A1* | 12/2012 | Byrne .............. C12Y 302/0102 514/44 R |
| 2015/0023924 | A1* | 1/2015 | High ...................... C12N 15/86 424/93.2 |

FOREIGN PATENT DOCUMENTS

| EP | 1359217 A1 | 11/2003 |
|---|---|---|
| WO | WO-1998/011244 | 3/1998 |
| WO | WO-1999/061601 | 12/1999 |
| WO | WO-2000/028061 | 5/2000 |
| WO | WO-2003/093460 A1 | 11/2003 |
| WO | WO-2005/005610 A2 | 1/2005 |
| WO | WO-2005/033321 | 4/2005 |
| WO | WO-2007/127264 A2 | 11/2007 |
| WO | WO-2008/027084 A2 | 3/2008 |

OTHER PUBLICATIONS

Hauck & Xiao entitled "Characterization of Tissue Tropism Determinants of Adeno-Associated Virus Type 1" (Journal of Virology, Feb. 2003, vol. 77, No. 4, pp. 2768-2774; IDS reference). (Year: 2003).*
Gao et al entitled "Clades of Adeno-Associated Viruses Are Widely Disseminated in Human Tissue" (Journal of Virology, Jun. 2004, vol. 78, No. 12, pp. 6381-6388; IDS reference). (Year: 2004).*
Vandenberghe et al, Mutational Strategy to Enhance or Rescue Functionality of Existing AAV Vectors, Molecular Therapy, vol. 11, Supplement 1, 503. p. 195, (Aug. 15, 2005).
Gao et al, Clades of Adeno-Associated Viruses are Widely Disseminated in Human Tissues, Journal of Virology, vol. 78, No. 12, p. 6381-6388, (Jun. 2004).
Gao et al, Adeno-Associated Viruses Undergo Substantial Evolution in Primates during Natural Infections, PNAS, vol. 100, No. 10, pp. 6081-6086, (May 13, 2003).
Hauck et al, Characterization of Tissue Tropism Determinants of Adeno-Associated Virus Type 1 Journal of Virology, vol. 77, No. 4, p. 2768-2774, (Feb. 2003).
Wu et al, Mutational Analysis of the Adeno-Associated Virus Tyoe 2 (AAV2) Capsid Gene and Construction of AAV2 Vectors with Altered Tropism, Journal of Virology, (Sep. 2000).

(Continued)

*Primary Examiner* — Catherine S Hibbert
(74) *Attorney, Agent, or Firm* — Howson & Howson LLP; Colleen Schaller

(57) ABSTRACT

A method of correcting singletons in a selected AAV sequence in order to increasing the packaging yield, transduction efficiency, and/or gene transfer efficiency of the selected AAV is provided. This method involves altering one or more singletons in the parental AAV capsid to conform the singleton to the amino acid in the corresponding position(s) of the aligned functional AAV capsid sequences.

27 Claims, 21 Drawing Sheets

Specification includes a Sequence Listing.

(56) References Cited

OTHER PUBLICATIONS

Opie et al, Identification of Amino Acid Residues in the Capsid Proteins of Adeno-Associated Virus Type 2 that Contribute to Heparan Sulfate Proteoglycan Binding, Journal of Virology, vol. 77, No. 12, pp. 6995-7006, (Jun. 2003).
Huttner et al, Genetic Modifications of the Adeno-Associated Virus Type 2 Capsid Reduce the Affinity and the Neutralizing Effects of Human Serum Antibodies, Gene Therapy, 10, (26), pp. 2139-2147, (Dec. 2003).
Vandenberghe et al, Naturally Occurring Singleton Residues in AAV Capsid Impact Vector Performance and Illustrate Structural Constraints, Gene Therapy, 16(12):1416-1428, (Dec. 2009), Supplementary Information, pp. 1-4.
Office Action dated Mar. 2, 2010 issued in corresponding Chinese Patent Application No. 200680010566.6.
Second Office Action dated Aug. 31, 2011 issued in corresponding Chinese Patent Application No. 200680010566.6.
Third Office Action dated Jan. 6, 2012 issued in corresponding Chinese Patent Application No. 200680010566.6.
Notice of Reasons for Rejection dated Sep. 13, 2011 issued in corresponding Japanese Patent Application No. JP 2008-505635.
Final Rejection, dated Oct. 9, 2012, issued in corresponding Japanese Patent Application No. 2008-505635.
Interrogation and Pretrial Reexamination, dated May 14, 2014, issued in corresponding Japanese Patent Application No. 2008-505635.
Notice of Reasons for Rejection, dated Aug. 29, 2014, issued in corresponding Japanese Patent Application No. 2008-505635.
Communication from European Patent Office, dated Feb. 2, 2015, issued on related European Patent Application No. 06749685.1 and response.
Communication from European Patent Office, dated Nov. 23, 2011, issued on related European Patent Application No. 06749685.1 and response.
Communication from European Patent Office, dated Aug. 6, 2009, issued on related European Patent Application No. 06749685.1 and response.
Communication from European Patent Office, dated Aug. 21, 2008, issued on related European Patent Application No. 06749685.1 and response.
Communication from European Patent Office, dated Jul. 7, 2008, issued on related European Patent Application No. 06749685.1 and response.
First Examination Report, dated Mar. 14, 2013, issued on related Indian Patent Application No. 7650/DELNP/2007.
Response to Mar. 14, 2013 Examination Report issued on related Indian Patent Application No. 7650/DELNP/2007, dated Dec. 20, 2013.
Second Examination Report with Hearing Notice issued on Indian Patent Application No. 7650/DELNP/2007, dated Apr. 22, 2014.
Response to May 16, 2014 hearing with Controller and Apr. 22, 2014 Office Action regarding same for related Indian Patent Application No. 7650/DELNP/2007, dated May 26, 2014.
Restriction Requirement, dated Feb. 13, 2017, issued on U.S. Appl. No. 14/624,671, and response.
Office Action, dated Jun. 30, 2017, issued on U.S. Appl. No. 15/408,567, and response.
Gao et al., "Novel adeno-associated viruses from rhesus monkeys as vectors for human gene therapy", PNAS, vol. 99(18):11854-11859, Sep. 2002.
GenBank entry AF513851, Sep. 2002.
GenBank entry AF513852, Sep. 2002.
Gao et al., "Biology of Adenovirus vectors with E1 and E4 deletions for liver-directed gene therapy", Journal of Viroloy, vol. 70(12):8934-8943, Dec. 1996.
Rutledge et al., "Infectious clones and vectors derived from Adeno-Associated Virus (AAV) serotypes other than AAV Type 2", Journal of Virology, vol. 72(1):309-319, Jan. 1998.

Xiao et al., "Gene therapy vectors based on Adeno-Associated Virus Type 1", Journal of Virology, vol. 73(5):3994-4003, May 1999.
Durigon et al., "Multiple primer pairs for polymerase chain reaction (PCR) amplification of human parvovirus B19 DNA", Journal of Virological Methods, vol. 44:155-165, Feb. 1993.
Hernandez et al., "Latent Adeno-associated virus infection elicits humoral but no cell-mediated immune responses in a nonhuman primate model", Journal of Virology, vol. 73(10):8549-8558, Oct. 1999.
Afione et al., "In vivo model of adeno-associated virus vector persistence and rescue", Journal of Virology, vol. 70(5):3235-3241, May 1996.
Schnell et al., "Activation of innate immunity in nonhuman primates following intraportal administration of adenoviral vectors", Molecular Therapy, vol. 3(5):708-722, May 2001.
Molecular Therapy, "Information for Authors", pp. 1-13.
Green et al., "Rhesus and pig-tailed macaque parvoviruses: identification of two new members of the erythrovirus genus in monkeys", Virology, vol. 269:105-112, Jan. 2000.
Brown et al., "Cloning and sequencing of the simial parvovirus genome", Virology, vol. 210:314-322, May 1995.
Zadori et al., "A viral phospholipase A2 is required for parvovirus infectivity", Developmental Cell, vol. 1:291-302, Aug. 2001.
Weitzman et al., "Adeno-associated virus (AAV) Rep proteins mediate complex formation between AAV DNA and its integration site in human DNA", PNAS, vol. 91:5808-5812, Jun. 1994.
Wang et al., "Enhancing Transgene Expression from Recombinant AAV8 Vectors in Different Tissues Using Woodchuck Hepatitis Virus Post-Transcriptional Regulatory Element", International Journal of Medical Sciences, vol. 13(4):286-291, Apr. 2016.
Charan et al., "Adeno-associated Virus Serotype 8 (AAV8) Delivery of Recombinant A20 to Skeletal Muscle Reduces Pathological Activation of Nuclear Factor (NF)-kB in Muscle of mdx Mice", Molecular Medicine, vol. 18:1527-1535, Nov. 2012.
Childers et al., "Gene Therapy Prolongs Survival and Restores Function in Murine and Canine Models of Myotubular Myopathy", Sci Transl Med, vol. 6(220):1-31, Jan. 2014.
Zhu et al., "Sustained Whole-Body Functional Rescue by Systemic Delivery of AAV8 Vectors in Heart Failure and Muscular Dystrophy Hamsters", Molecular Therapy, vol. 11(suppl 1):916, May 2005.
Lytle et al., "Effects of FVIII immunity on hepatocyte and hematopoietic stem cell-directed gene therapy of murine hemophilia A", Methods & Clinical Development, vol. 3:15056, Feb. 2016.
Gilkes et al., "Mucopolysaccharidosis IIIB confers enhanced neonatal intracranial transduction by AAV8 but not by 5, 9 or rh10", Gene Therapy, vol. 23:263-271, Jan. 2016.
Pignataro et al., "Adeno-Associated Viral Vectors Serotype 8 for Cell-Specific Delivery of Therapeutic Genes in the Central Nervous System", Frontiers in Neuroanatomy, vol. 11(2):1-13, Feb. 2017.
Black et al., "Adeno-associated virus 8-mediated gene therapy for choroideremia: preclinical studies in in vitro and in vivo models", The Journal of Gene Medicine, vol. 16:122-130, Jun. 2014.
Dai et al., "Long-term retinal cone rescue using a capsid mutant AAV8 vector in a mouse model of CNGA3-achromatopsia", PLOS One, vol. 12(11):e0188032, Nov. 2017.
Fischer et al., "Codon-Optimized RPGR Improves Stability and Efficacy of AAV8 Gene Therapy in Two Mouse Models of X-Linked Retinitis Pigmentosa", Molecular Therapy, vol. 25(8):1854-1865, May 2017.
ClinicalTrials.org, "AAV8 Vector Trials", Nov. 2017.
Mountz, "Monkey see, monkey do", vol. 10:194-196, Gene Therapy, vol. 10:194, Jan. 2003.
Extended European Search Report, dated Oct. 11, 2019, in corresponding Divisional Patent Application No. 19178288.7, filed Apr. 7, 2006.
Statement of Opposition, dated Jun. 20, 2017, filed on related European Patent No. 1453547.
Proprietor's Response to the Opposition, dated Dec. 5, 2017, filed on related European Patent No. 1453547.

\* cited by examiner

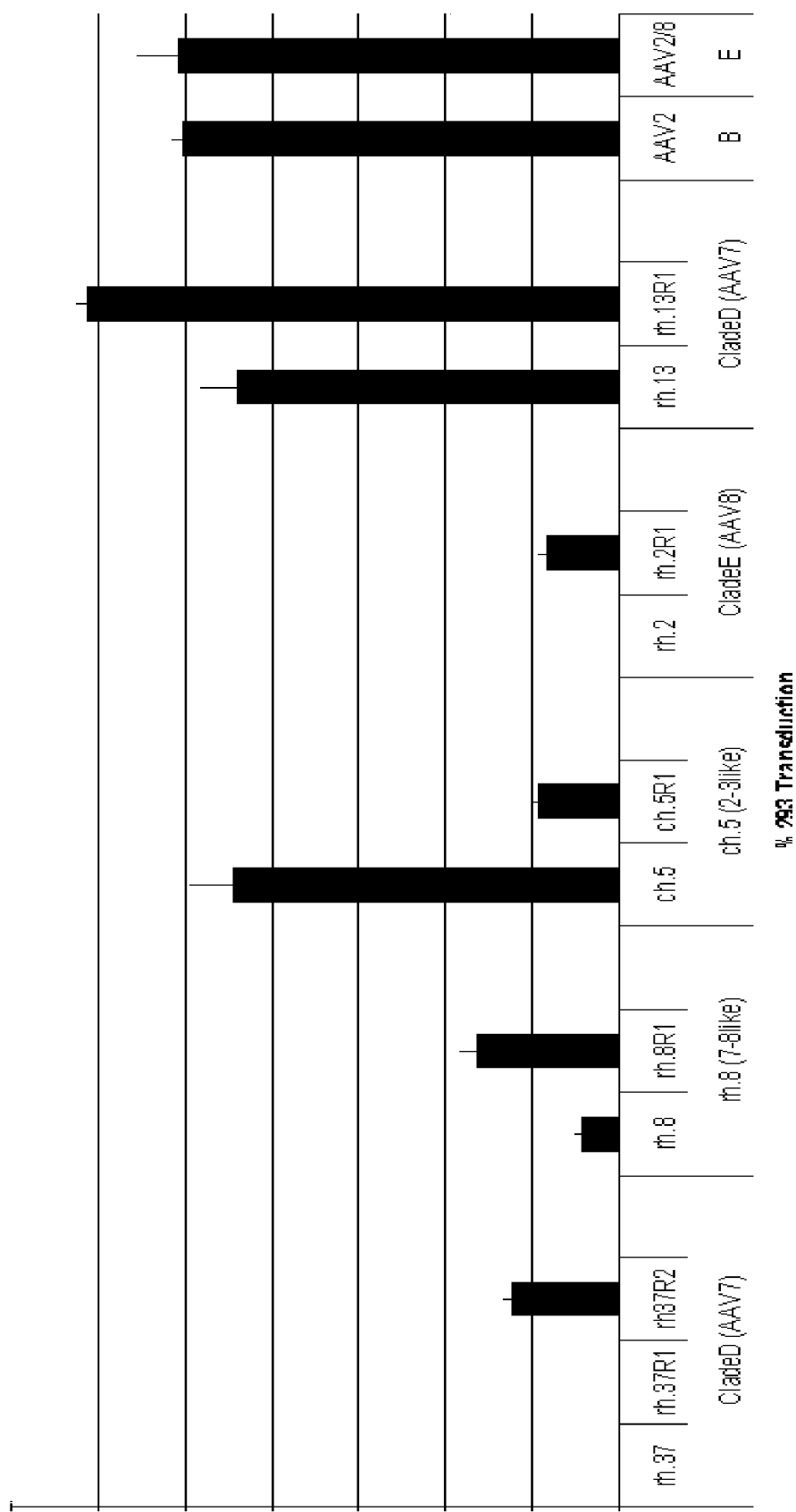
Fig. 1: Singleton In Vitro lysate Transduction

```
              2210       2220
         ....|....|....|....|
AAV2     acctgactcgtaatctgtaa
cy.5     .....c.....c........
rh.10    .....c.....c........
rh.13    .....c.....c........
AAV1     ...t..c.....ccc.....
AAV3     ...t..c...a..a..ct..
AAV6     .....c.....ccc......
AAV7     .....c.....c........
AAV8     .....c.....c........
hu.13    ....................
hu.26    ....................
hu.37    .....c..c...........
hu.53    .....c..c...........
hu.39    .....c..c...........
rh.43    .....c..c...........
rh.46    .....c..c...........
```

|         | 610                  | 620                  | 630                  | 640                  | 650                  | 660                  | 670                  | 680                  | 690                  | 700   |
|---------|----------------------|----------------------|----------------------|----------------------|----------------------|----------------------|----------------------|----------------------|----------------------|-------|
| AAV2    | TQGVLPGMVWQDRDVYLQGPIWAKIPHTDGHFHPSPLMGGFGLKHPPPQILIKNTPVPANPSTTFSAAKFASFITQYSTGQVSVEIEWELQKENSKRWNP | | | | | | | | | |
| cy.5    | S..A................................N................................PEV.TP...................... | | | | | | | | | |
| rh.10   | S..A................................N..............................D.P...Q.L...................... | | | | | | | | | |
| rh.13   | S..A................................N................................PEV.TP...................... | | | | | | | | | |
| AAV1    | AM.A..................................................................PAE..T...................... | | | | | | | | | |
| AAV3    | H..A...................................................................P..P....................... | | | | | | | | | |
| AAV6    | VM.A..................................................................PAE..T...................... | | | | | | | | | |
| AAV7    | N..A................................N................................PEV.TP...................... | | | | | | | | | |
| AAV8    | S..A................................N...............................D.P...NQS.LN.................. | | | | | | | | | |
| hu.13   | ....................................N.............................................................| | | | | | | | | |
| hu.26   | ..................................................................................................| | | | | | | | | |
| hu.37   | S..A................................N..............M................D.P...Q.L...................... | | | | | | | | | |
| hu.53   | H..A.................................................................D.P.N..S...................... | | | | | | | | | |
| rh.39   | S..A................................N..............................D.P...Q.L...................... | | | | | | | | | |
| rh.43   | S..A................................N...............................D.P...NQS.LN.................. | | | | | | | | | |
| rh.46   | S..A................................N...............................D.P.A.NQ..LN.................. | | | | | | | | | |

|         | 710                  | 720                  | 730                  | 740   |
|---------|----------------------|----------------------|----------------------|-------|
| AAV2    | EIQYTSNYNKSVNVDFTVDTNGVYSEPRPIGTRYLTRNL* | | | |
| cy.5    | ......A..N..E.A.NNE..T................* | | | |
| rh.10   | ......Y..T...A.N.D.T..................* | | | |
| rh.13   | ......A..N..E.A.NNE..T................* | | | |
| AAV1    | ..V...A..A.......N..L.T..............P.- | | | |
| AAV3    | ..V...A..A..........N..L.T...........P.- | | | |
| AAV6    | ......FE.QTG...A..SQ..................- | | | |
| AAV7    | ......Y..TS..A.N.E....................- | | | |
| AAV8    | .......................................*| | | |
| hu.13   | ........................................*| | | |
| hu.26   | ......Y..T...A.N.E.T..................* | | | |
| hu.37   | ........................................*| | | |
| hu.53   | ......Y..T...A.N.E.T..................* | | | |
| rh.39   | ......Y..T...A.N.E....................* | | | |
| rh.43   | ......Y..TS..A.N.E....................* | | | |
| rh.46   | ......Y..T...A.N.E....................* | | | |

FIG. 5D

```
         10         20         30         40         50         60         70         80         90        100
         |          |          |          |          |          |          |          |          |          |
rh.13    MAADGYLPDWLEDNLSEGIREWWDLKPGAPKPKANQQKQDDGRGLIVLPGYKYLGPFNGLDKGEPVNEADAAALEHDKAYDKQLEQGDNPYLKYNHADAEF
rh.2     ................................................................A.........Q.KA.......R.............
rh.37    ................................................................A.........Q.KA.......R.............
rh.8     .........T........Q..K....P..P..PAERHK...S.....................A.........Q.KA.......R.............
hu.29    ..................................................................................R.DS.............
rh.64    ................................................................A.........Q.KA.......R.............

110        120        130        140        150        160        170        180        190        200
         |          |          |          |          |          |          |          |          |          |
rh.13    QERLQEDTSFGGNLGRAVFQAKKRVLEPLGLVEEGAKTAPGKKRPIE----SPDSSTGIGKKGQQPAKKKLNFGQTGDSESVPDPQPLGEPPAAPSGLG
rh.2     ..........................................................V.PSPQR........H..R.R.................
rh.37    .................................................................D----.....................I..G..
rh.8     ...K.....................................................V.QSPQ-E....S...T......R...............SV
hu.29    ....................................................PV...V.HSP-AE...S.T.S.N..R.R.....D........I..SV
rh.64    ..........................................................V.PSPQR..........R.R.................

210        220        230        240        250        260        270        280        290        300
         |          |          |          |          |          |          |          |          |          |
rh.13    SGTMAAGGGAPMADNNEGADGVGNASGNWHCDSTWLGDRVITTSTRTWALPTYNNHLYKQIS-SQS-GATNDNHFFGYSTPWGYFDFNRFHCHFSPRDWQ
rh.2     ...............T...............................................NGT.G.S......TY..................
rh.37    ..PN...S........S...............................................-S..S....Y..................
rh.8     ..TN..T.S.......S...............................................NGT.G.S.....TY..................
hu.29    .................M..............................................--SQS..S...Y..................
rh.64    ................SS..............................................NGT.G.S......TY..................

310        320        330        340        350        360        370        380        390        400
         |          |          |          |          |          |          |          |          |          |
rh.13    RLINNNWGFRPRKLRFKLFNIQVKEVTTNDGVTTIANNLTSTIQVFSDSEYQLPYVLGSAHQGCLPPFPADVFMIPQYGYLTLNNGSQSVGRSSFYCLEY
rh.2     ....KR.N.................Q.E.TK.............T.............P...................A...............
rh.37    ....K....................................V.......T..........................................
rh.8     ....KR.N.................E.TK...........V..T...V..............................AL..............
hu.29    ....KR.N.................Q..T...........V..T...V.............................A...............G.
rh.64    ....KR.S.................Q.E.TK.........V..T...V.............................A...............
```

FIG. 6A

```
            410       420       430       440       450       460       470       480       490       500
            ....|....|....|....|....|....|....|....|....|....|....|....|....|....|....|....|....|....|....|....|
rh.13   FPSQMLRTGNNFEFSYTFEEVPFHSSYAHSQSLDRLMNPLIDQYLYYLARTQSTT--GSTRELQFHQAGPNTMAEQSKNWLPGPCYRQQRLSKNIDSNNN
rh.2    .........................D.........................S..GGTQG.QQ.L.S...AN.SA.A............V.TTLSQ...
rh.37   .........................D.....................................................................L.F
rh.8    .........................Q...................V..T.G-T.G.QT.A.S....SS..N.AR.V...............V.TTTNQ.
hu.29   .........................T...................S..NTPSGTTTQSR..S...ASDIRD..R................V..TSAD..
rh.64   .........................S.........................S...GGTAG.QQ.L.S....SN.SA.AR............V.TTLSQ.

510       520       530       540       550       560       570       580       590       600
            ....|....|....|....|....|....|....|....|....|....|....|....|....|....|....|....|....|....|....|....|
rh.13   SNFAWTGATKYHLNGRNSLTNPGVAMATNKDDEDQFFPINGVLVFGETGAAN-KTTLENVLMTSEEEIKTTNPVATEEYGVVSSNLQSSTAGPQTQTVNS
rh.2    ............D..V..........H.....ER...SS...M..KQ..GKDNVDYSS.ML..........Q......AD...QTNGA.IVG.......
rh.37   ....A............IP.........................K..................................................S.I
rh.8    .........A..FK...D..M.....SH...D.R...SS....I..KQ..G.DGVDYSQ..I.D....A............A.AI..N..AANTQA..GL.HN
hu.29   ....EYS......D..V..P......SH...EK...QS....I..KQ.PEKTNVDI.K.MI.D...R........Q..S..T....GNTQAA.AD..T
rh.64   ............D..V...............R...SS.I.M..KQ..GKDNVDYS..ML..........Q......AD...QQNTA.IVGA......

610       620       630       640       650       660       670       680       690       700
            ....|....|....|....|....|....|....|....|....|....|....|....|....|....|....|....|....|....|....|....|
rh.13   QGALPGMVWQNRDVYLQGPIWAKIPHTDGNFHPSPLMGGFGLKHPPPQILIKNTPVPANPPEVFTPAKFASFITQYSTGQVSVEIEWELQKENSKRWNPE
rh.2    ................................................................V....D..TT.SQ.L...................
rh.37   ....VI..........................E...............................................................
rh.8    ....V........D...................................................D..LT.NQ..LN..................
hu.29   .................................H..............................STT.SA......................
rh.64   .............................................................................D..TA.NQ..LN..........V..................R.

710       720       730
            ....|....|....|....|....|....|..
rh.13   IQYTSNYAKSNNVEFAVNNEGVYTEPRPIGTRYLTRNL*
rh.2    ....Y..T.D....T.T.S...............*
rh.37   ..............PD....S..............*
rh.8    ....Y..T.D...T.....S..............*
hu.29   ....N.V..D.T.DTN....S..............*
rh.64   ....Y..T.D....T.....S..............*
```

FIG. 6B

SEQUENCE LISTING

```
<160> NUMBER OF SEQ ID NOS: 49

<210> SEQ ID NO 1
<211> LENGTH: 738
<212> TYPE: PRT
<213> ORGANISM: Unknown
<220> FEATURE:
<223> OTHER INFORMATION: rhesus adeno-associated virus, 20

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
```

```
            180                 185                 190
Pro Ala Gly Pro Ser Gly Leu Gly Ser Gly Thr Met Ala Ala Gly Gly
            195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Ala Gly Thr Gln Gln Leu Leu
    450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
        515                 520                 525
His Lys Asp Asp Glu Glu Arg Phe Phe Pro Ser Ser Gly Val Leu Met
    530                 535                 540
Phe Gly Lys Gln Gly Ala Gly Lys Asp Asn Val Asp Tyr Ser Ser Val
545                 550                 555                 560
Met Leu Thr Ser Glu Glu Ile Lys Thr Thr Asn Pro Val Ala Thr
                565                 570                 575
Glu Gln Tyr Gly Val Val Ala Asp Asn Leu Gln Gln Gln Asn Ala Ala
            580                 585                 590
Pro Ile Val Gly Ala Val Asn Ser Gln Gly Ala Leu Pro Gly Met Val
        595                 600                 605
```

```
Trp Gln Asn Arg Asp Val Tyr Leu Gln Gly Pro Ile Trp Ala Lys Ile
        610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                645                 650                 655
Pro Ala Asp Pro Pro Thr Thr Phe Ser Gln Ala Lys Leu Ala Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
        690                 695                 700
Ser Asn Tyr Tyr Lys Ser Thr Asn Val Asp Phe Ala Val Asn Thr Glu
705                 710                 715                 720
Gly Thr Tyr Ser Glu Pro Arg Pro Ile Gly Thr Arg Tyr Leu Thr Arg
                725                 730                 735
Asn Leu

<210> SEQ ID NO 2
<211> LENGTH: 733
<212> TYPE: PRT
<213> ORGANISM: Unknown
<220> FEATURE:
<223> OTHER INFORMATION: capsid of Rhesus adeno-associated virus clone
      32/33

<400> SEQUENCE: 2

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Leu Glu Ser Pro Gln Glu Pro Asp Ser Ser Gly Ile Gly Lys
145                 150                 155                 160
Lys Gly Lys Gln Pro Ala Lys Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
Ser Asp Ile Glu Met Arg Ala Ala Pro Gly Gly Asn Ala Val Asp Ala
        195                 200                 205
Gly Gln Gly Ser Asp Gly Val Gly Asn Ala Ser Gly Asp Trp His Cys
    210                 215                 220
```

```
Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640
```

-continued

Pro Pro Gln Ile Phe Ile Lys Asn Thr Pro Val Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Tyr Gly Asn
        690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 3
<211> LENGTH: 738
<212> TYPE: PRT
<213> ORGANISM: Unknown
<220> FEATURE:
<223> OTHER INFORMATION: Rhesus adeno-associated virus clone 39 capsid

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

-continued

```
Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
```

```
              690             695             700
Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 4
<211> LENGTH: 738
<212> TYPE: PRT
<213> ORGANISM: Unknown
<220> FEATURE:
<223> OTHER INFORMATION: Rhesus adeno-associated virus clone 46 capsid
      protein

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Ser Val Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
```

-continued

|  |  |  |  |
|---|---|---|---|
| 305 | 310 | 315 | 320 |

Ile Gln Val Lys Glu Val Thr Gln Asn Glu Gly Thr Lys Thr Ile Ala
                    325                 330                 335

Asn Asn Leu Thr Ser Thr Ile Gln Val Phe Thr Asp Ser Glu Tyr Gln
                    340                 345                 350

Leu Pro Tyr Val Leu Gly Ser Ala His Gln Gly Cys Leu Pro Pro Phe
                    355                 360                 365

Pro Ala Asp Val Phe Met Ile Pro Gln Tyr Gly Tyr Leu Thr Leu Asn
                    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Ser Phe Ser Tyr
                    405                 410                 415

Thr Phe Glu Asp Val Pro Phe His Ser Ser Tyr Ala His Ser Gln Ser
                    420                 425                 430

Leu Asp Arg Leu Met Asn Pro Leu Ile Asp Gln Tyr Leu Tyr Tyr Leu
                    435                 440                 445

Ser Arg Thr Gln Ser Thr Gly Gly Thr Ala Gly Thr Gln Gln Leu Leu
450                 455                 460

Phe Ser Gln Ala Gly Pro Ser Asn Met Ser Ala Gln Ala Arg Asn Trp
465                 470                 475                 480

Leu Pro Gly Pro Cys Tyr Arg Gln Gln Arg Val Ser Thr Thr Leu Ser
                    485                 490                 495

Gln Asn Asn Asn Ser Asn Phe Ala Trp Thr Gly Ala Thr Lys Tyr His
                    500                 505                 510

Leu Asn Gly Arg Asp Ser Leu Val Asn Pro Gly Val Ala Met Ala Thr
                    515                 520                 525

Asn Lys Asp Asp Glu Asp Arg Phe Phe Pro Ser Ser Gly Ile Leu Met
                    530                 535                 540

Phe Gly Lys Gln Gly Ala Gly Lys Asp Asn Val Asp Tyr Ser Asn Val
545                 550                 555                 560

Met Leu Thr Ser Glu Glu Ile Lys Ala Thr Asn Pro Val Ala Thr
                    565                 570                 575

Glu Gln Tyr Gly Val Val Ala Asp Asn Leu Gln Gln Asn Thr Ala
                    580                 585                 590

Pro Ile Val Gly Ala Val Asn Ser Gln Gly Ala Leu Pro Gly Met Val
                    595                 600                 605

Trp Gln Asn Arg Asp Val Tyr Leu Gln Gly Pro Ile Trp Ala Lys Ile
                    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                    645                 650                 655

Pro Ala Asp Pro Pro Thr Ala Phe Asn Gln Ala Lys Leu Asn Ser Phe
                    660                 665                 670

Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
                    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                    725                 730                 735

-continued

Asn Leu

<210> SEQ ID NO 5
<211> LENGTH: 738
<212> TYPE: PRT
<213> ORGANISM: Unknown
<220> FEATURE:
<223> OTHER INFORMATION: Rhesus adeno-associated virus clone 73 capsid

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

```
Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Ser Phe Ser Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Ser Asn Met Ser Ala Gln Ala Arg Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

Asn Lys Asp Asp Glu Asp Arg Phe Phe Pro Ser Ser Gly Ile Leu Met
530                 535                 540

Phe Gly Lys Gln Gly Ala Gly Lys Asp Asn Val Asp Tyr Ser Asn Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Arg Gln Asn Thr Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Ala Phe Asn Gln Ala Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 6
<211> LENGTH: 736
<212> TYPE: PRT
<213> ORGANISM: Unknown
```

<220> FEATURE:
<223> OTHER INFORMATION: Rhesus adeno-associated virus clone 74 capsid

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Leu Asn Leu Lys Pro Gly Ala Pro Gln Pro
            20                  25                  30

Lys Ala Asn Gln Gln Lys Gln Asp Asn Ala Arg Gly Leu Val Leu Pro
        35                  40                  45

Gly Tyr Lys Tyr Leu Gly Pro Phe Asn Gly Leu Asp Lys Gly Asp Pro
    50                  55                  60

Val Asn Glu Ala Asp Ala Ala Leu Glu His Asp Lys Ala Tyr Gly
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Lys Asp Thr Ser Phe Gly Gly
            100                 105                 110

Asn Leu Gly Lys Ala Val Phe Gln Ala Lys Lys Arg Ile Leu Glu Pro
        115                 120                 125

Leu Gly Leu Val Glu Thr Pro Ala Lys Thr Ala Pro Gly Lys Lys Arg
    130                 135                 140

Pro Val Asp Pro Ser Pro Gln Arg Ser Pro Asp Ser Ser Ser Gly Ile
145                 150                 155                 160

Gly Lys Lys Ser Pro His Pro Ala Arg Lys Arg Leu Asn Phe Gly Gln
                165                 170                 175

Thr Gly Glu Ala Glu Ser Val Pro Asp Pro Gln Pro Ile Gly Glu Pro
            180                 185                 190

Pro Ser Asp Pro Ser Ser Val Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Thr Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

-continued

Ser Gln Met Leu Arg Thr Gly Asn Asn Phe Gln Phe Ser Tyr Thr Phe
            405                 410                 415

Glu Asp Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Ser Lys
    435                 440                 445

Thr Gln Gly Thr Asn Ala Thr Val Gln Gly Ala Lys Leu Gln Phe Ser
450                 455                 460

Gln Ala Gly Pro Ser Asn Met Arg Asp Gln Ala Arg Asn Trp Leu Pro
465                 470                 475                 480

Gly Pro Cys Tyr Arg Gln Gln Arg Val Ser Lys Thr Ala Asn Asp Asn
            485                 490                 495

Asn Asn Ser Glu Tyr Ala Trp Thr Gly Ala Thr Lys Tyr His Leu Asn
        500                 505                 510

Gly Arg Asp Ser Leu Val Asn Pro Gly Pro Ala Met Ala Ser His Lys
    515                 520                 525

Asp Asp Glu Glu Lys Phe Phe Pro Met Asn Gly Thr Leu Val Phe Gly
530                 535                 540

Lys Asn Gly Ala Gly Asn Ser Asn Val Asp Ile Glu Asn Val Met Ile
545                 550                 555                 560

Thr Asp Glu Glu Glu Ile Arg Thr Thr Asn Pro Val Ala Thr Glu Gln
            565                 570                 575

Tyr Gly Val Val Ser Asp Asn Leu Gln Ser Ser Asn Thr Arg Pro Ile
        580                 585                 590

Thr Gly Asp Val Asp Ser Gln Gly Val Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Ala Thr Thr Phe Thr Pro Gly Lys Phe Ala Ser Phe Ile Thr
        660                 665                 670

Gln Tyr Ser Thr Gly Gln Val Ser Val Gln Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 7
<211> LENGTH: 2208
<212> TYPE: DNA
<213> ORGANISM: Unknown
<220> FEATURE:
<223> OTHER INFORMATION: adeno-associated virus serotype 2 capsid

<400> SEQUENCE: 7
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180

```
aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt gggggcaacc tcggacgagc agtcttccag      360
gcgaaaaaga gggttcttga acctctgggc ctggttgagg aacctgttaa gacggctccg      420
ggaaaaaaga ggccggtaga gcactctcct gtggagccag actcctcctc gggaaccgga      480
aaggcgggcc agcagcctgc aagaaaaaga ttgaattttg gtcagactgg agacgcagac      540
tcagtacctg accccagcc tctcggacag ccaccagcag cccctctgg tctgggaact      600 aatacgatgg ctacaggcag tggcgcacca atggcagaca taacgagg cgccgacgga      660 gtgggtaatt cctcgggaaa ttggcattgc gattccacat ggatgggcga cagagtcatc      720
accaccagca cccgaacctg ggccctgccc acctacaaca accacctcta caaacaaatt      780
tccagccaat caggagcctc gaacgacaat cactactttg gctacagcac cccttggggg      840
tattttgact tcaacagatt ccactgccac ttttcaccac gtgactggca agactcatc      900 aacaacaact ggggattccg acccaagaga ctcaacttca gctctttaa cattcaagtc      960 aaagaggtca cgcagaatga cggtacgacg acgattgcca ataaccttac cagcacggtt      1020
caggtgttta ctgactcgga gtaccagctc ccgtacgtcc tcggctcggc catcaagga      1080 tgcctcccgc cgttcccagc agacgtcttc atggtccac agtatggata cctcaccctg      1140
aacaacggga gtcaggcagt aggacgctct tcatttact gcctggagta ctttccttct      1200
cagatgctgc gtaccggaaa caactttacc ttcagctaca cttttgagga cgttcctttc      1260
cacagcagct acgctcacag ccagagtctg accgtctca tgaatcctct catcgaccag      1320
tacctgtatt acttgagcag aacaaacact ccaagtggaa ccaccacgca gtcaaggctt      1380 cagtttttctc aggccggagc gagtgacatt cgggaccagt ctaggaactg gcttcctgga      1440
ccctgttacc gccagcagcg agtatcaaag acatctgcgg ataacaacaa cagtgaatac      1500
tcgtggactg gagctaccaa gtaccacctc aatggcagag actctctggt gaatccgggc      1560
ccggccatgg caagccacaa ggacgatgaa gaaaagtttt tcctcagag cggggttctc      1620 atctttggga agcaaggctc agagaaaaca atgtgtgaca ttgaaaaggt catgattaca      1680
gacgaagagg aaatcaggac aaccaatccc gtggctacgg agcagtatgg ttctgtatct      1740
accaacctcc agagaggcaa cagacaagca gctaccgcag atgtcaacac acaaggcgtt      1800
cttccaggca tggtctggca ggacagagat gtgtaccttc aggggcccat ctgggcaaag      1860
attccacaca cggacggaca ttttcacccc tctcccctca tgggtggatt cggacttaaa      1920
caccctcctc acagattctc catcaagaac ccccggtac ctgcgaatcc ttcgaccacc      1980
ttcagtgcgc aaagtttgc ttccttcatc acacagtact ccacgggaca ggtcagcgtg      2040
gagatcgagt gggagctgca gaaggaaaac agcaaacgct ggaatcccga aattcagtac      2100
acttccaact acaacaagtc tgttaatgtg gactttactg tggacactaa tggcgtgtat      2160
tcagagcctc gccccattgg caccagatac ctgactcgta atctgtaa                  2208
```

<210> SEQ ID NO 8
<211> LENGTH: 2187
<212> TYPE: DNA
<213> ORGANISM: Unknown
<220> FEATURE:
<223> OTHER INFORMATION: cynomolgus (cy.) 5 capsid

<400> SEQUENCE: 8

```
atggctgccg atggttatct tccagattgg ctcgagggca acctctctga gggcattcgc    60
gagtggtggg acttgaaacc tggagccccg aaacccaaag ccaaccagca aaagcaggac   120
gacggccggg gtctggtgct tcctggctac aggtacctcg gacccttcaa cggactcgac   180
aagggagagc cggtcaacga ggcagacgcc gcggccctcg agcacgacaa ggcctacgac   240
aagcagctcg agcaggggga caacccgtac ctcaagtaca ccacgccga cgccgagttt   300
caggagcgtc ttcaagaaga tacgtctttt gggggcaacc tcgggcgagc agtcttccag   360
gccaagaagc gggttctcga acctctcggt ctggttgagg aaggcgctaa gacggctcct   420
ggaaagaaga gacccataga atcccccgac tcctccacgg gcatcggcaa gaacggccag   480
ccgcccgcta aaaagaagct caactttggg cagactggcg actcagagtc agtgcccgac   540
ccccaacctc tcggagaacc tcccgccgcg ccctcaggtc tgggatctgg tacaatggct   600
gcaggcggtg gcgcaccaat ggcagacaat aacgaaggcg ccgacggagt gggtaatgcc   660
tccggaaatt ggcattgcga ttccacatgg ctgggcgaca gagtcatcac caccagcacc   720
cgcacctggg ccctgcccac ctacaacaac cacctctaca gcagatatc aagtcagagc   780
ggggctacca cgacaacca cttcttcggc tacagcaccc cctggggcta ttttgacttc   840
aacagattcc actgccactt ctcaccagt gactggcagc gactcatcaa caacaactgg   900
ggattccggc ccagaaagct gcggttcaag ttgttcaaca tccaggtcaa ggaggtcacg   960
acgaacgacg gcgttacgac catcgctaat aaccttacca gcacgattca ggtcttctcg  1020
gactcggagt accaactgcc gtacgtcctc ggctctgcgc accagggctg cctccctccg  1080
ttccctgcgg acgtgttcat gattcctcag tacggatatc tgactctaaa caacggcagt  1140
cagtctgtgg gacgttcctc cttctactgc ctggagtact ttccttctca gatgctgaga  1200
acgggcgata actttgaatt cagctacacc tttgaggaag tgcctttcca cagcagctat  1260
gcgcacagcc agagcctgga ccggctgatg aatcccctca tcgaccagta cctgtactac  1320
ctggcccgga cccagagcac tacggggtcc acaagggagc tgcagttcca tcaggctggg  1380
cccaacacca tggccgagca atcaaagaac tggctgcccg accctgtta tcggcagcag  1440
agactgtcaa aaacataga cagcaacaac aacagtaact tgcctggac cggggccact  1500
aaataccatc tgaatggtag aaattcatta accaacccgg gcgtagccat ggccaccaac  1560
aaggacgacg aggaccagtt cttttcccatc aacggagtgc tggttttgg caaaacgggg  1620
gctgccaaca agacaacgct ggaaaacgtg ctaatgacca gcgaggagga gatcaaaacc  1680
accaatcccg tggctacaga agaatacggt gtggtctcca gcaacctgca atcgtctacg  1740
gccggacccc agacacagac tgtcaacagc caggggctc tgcccggcat ggtctggcag  1800
aaccgggacg tgtacctgca gggtcccatc tgggccaaaa ttcctcacac ggacggcaac  1860
tttcacccgt ctcccctgat gggcggattt ggactcaaac acccgcctcc tcaaattctc  1920
atcaaaaaca ccccggtacc tgctaatcct ccagaggtgt ttactcctgc aagtttgcc  1980
tcatttatca cgcagtacag caccggccag gtcagcgtgg agatcgagtg gaactgcag  2040
aaagaaaaca gcaaacgctg gaatccagag attcagtaca cctcaaatta tgccaagtct  2100
aataatgtgg aatttgctgt caacaacgaa ggggtttata ctgagcctcg ccccattggc  2160
acccgttacc tcacccgtaa cctgtaa                                      2187
```

<210> SEQ ID NO 9
<211> LENGTH: 2217
<212> TYPE: DNA
<213> ORGANISM: Unknown

<220> FEATURE:
<223> OTHER INFORMATION: rhesus adeno-associated virus 10 capsid

<400> SEQUENCE: 9

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac      180
aaggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag ccagcagcc cgcgaaaaag agactcaact ttgggcagac tggcgactca     540
gagtcagtgc ccgaccctca accaatcgga gaaccccccg caggcccctc tggtctggga     600
tctggtacaa tggctgcagg cggtggcgct ccaatggcag acaataacga aggcgccgac     660
ggagtgggta gttcctcagg aaattggcat gcgattcca catggctggg cgacagagtc     720
atcaccacca gcacccgaac ctgggccctc cccacctaca caaccaccct ctacaagcaa     780
atctccaacg gacttcggg aggaagcacc aacgacaaca cctacttcgg ctacagcacc     840
ccctgggggt atttttgactt taacagattc cactgccact tctcaccacg tgactggcag     900
cgactcatca caacaactg gggattccgg cccaagagac tcaacttcaa gctcttcaac     960
atccaggtca aggaggtcac gcagaatgaa ggcaccaaga ccatcgccaa taaccttacc    1020
agcacgattc aggtctttac ggactcggaa taccagctcc cgtacgtcct cggctctgcg    1080
caccagggct gcctgcctcc gttcccggcg gacgtcttca tgattcctca gtacgggtac    1140
ctgactctga acaatggcag tcaggccgtg ggccgttcct ccttctactg cctggagtac    1200
tttcccttctc aaatgctgag aacgggcaac aactttgagt tcagctacca gtttgaggac    1260
gtgcctttc acagcagcta cgcgcacagc caaagcctgg accggctgat gaacccctc    1320
atcgaccagt acctgtacta cctgtctcgg actcagtcca cgggaggtac cgcaggaact    1380
cagcagttgc tattttctca ggccgggcct aataacatgt cggctcaggc caaaaactgg    1440
ctaccgggc cctgctaccg cagcaacgc gtctccacga cactgtcgca aaataacaac    1500
agcaactttg cctggaccgg tgccaccaag tatcatctga atggcagaga ctctctggta    1560
aatcccggtg tcgctatggc aacccacaag acgacgaag agcgattttt tccgtccagc    1620
ggagtcttaa tgtttgggaa acagggagct ggaaaagaca acgtggacta tagcagcgtt    1680
atgctaacca gtgaggaaga aattaaaacc accaacccag tggccacaga acagtacggc    1740
gtggtggccg ataacctgca acagcaaaac gccgctccta ttgtagggc cgtcaacagt    1800
caaggagcct tacctggcat ggtctggcag aaccggacg tgtacctgca gggtcctatc    1860
tgggccaaga ttcctcacac ggacggaaac tttcatccct cgccgctgat gggaggcttt    1920
ggactgaaac accgcctcc tcagatcctg attaagaata cacctgttcc cgcggatcct    1980
ccaactacct tcagtcaagc taagctgcg tcgttcatca cgcagtacag caccggacag    2040
gtcagcgtgg aaattgaatg ggagctgcag aaagaaaaca gcaaacgctg aacccagag    2100
attcaataca cttccaacta ctacaaatct acaaatgtgg actttgctgt taacacagat    2160
ggcacttatt ctgagcctcg ccccatcggc acccgttacc tcaccccgtaa tctgtaa     2217
```

<210> SEQ ID NO 10
<211> LENGTH: 2187
<212> TYPE: DNA
<213> ORGANISM: Unknown
<220> FEATURE:
<223> OTHER INFORMATION: rhesus adeno-associated virus 13 capsid

<400> SEQUENCE: 10

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac     180
aagggagagc cggtcaacga ggcagacgcc gcggccctcg agcacgacaa ggcctacgac     240
aagcagctcg agcaggggga caacccgtac ctcaagtaca ccacgccga cgccgagttt     300
caggagcgtc ttcaagaaga tacgtctttt gggggcaacc tcgggcgagc agtcttccag     360
gccaagaagc gggttctcga acctctcggt ctggttgagg aaggcgctaa gacggctcct     420
ggaaagaaga gacccataga atcccccgac tcctccacgg catcggcaa gaaaggccag     480
cagcccgcta aaaagaagct caactttggg cagactggcg actcagagtc agtgcccgac     540
ccccaacctc tcggagaacc tcccgccgcg ccctcaggtc tgggatctgg tacaatggct     600
gcaggcggtg gcgcaccaat ggcagacaat aacgaaggcg ccgacggagt gggtaatgcc     660
tccggaaatt ggcattgcga ttccacatgg ctgggcgaca gagtcatcac caccagcacc     720
cgcacctggg ccctgcccac ctacaacaac cacctctaca gcagatatc aagtcagagc     780
gggctacca cgacaacca cttcttcggc tacagcaccc cctggggcta ttttgacttc     840
aacagattcc actgccactt ctcaccacgt gactggcagc gactcatcaa caacaactgg     900
ggattccggc cagaaagct gcggttcaag ttgttcaaca tccaggtcaa ggaggtcacg     960
acgaacgacg gcgttacgac catcgctaat aaccttacca gcacgattca ggtcttctcg    1020
gactcggagt accaactgcc gtacgtcctc ggctctgcgc accagggctg cctccctccg    1080
ttccctgcgg acgtgttcat gattcctcag tacggatatc tgactctaaa caacggcagt    1140
cagtctgtgg acgttcctc cttctactgc ctggagtact tccttctca gatgctgaga    1200
acgggcaata actttgaatt cagctacacc tttgaggaag tgcctttcca cagcagctat    1260
gcgcacagcc agagcctgga ccggctgatg aatccccctca tcgaccagta cctgtactac    1320
ctggcccgga cccagagcac tacggggtcc acaagggagc tgcagttcca tcaggctggg    1380
cccaacacca tggccgagca atcaaagaac tggctgcccg accctgtta tcggcagcag    1440
agactgtcaa aaacataga cagcaacaac acagtaact ttgcctggac cggggccact    1500
aaataccatc tgaatggtag aaattcatta accaacccgg gcgtagccat ggccaccaac    1560
aaggacgacg aggaccagtt ctttcccatc aacggagtgc tggttttttgg cgaaacgggg    1620
gctgccaaca gacaacgct ggaaaacgtg ctaatgacca gcgaggagga gatcaaaacc    1680
accaatcccg tggctacaga agaatacggt gtggtctcca gcaacctgca atcgtctacg    1740
gccggacccc agacacagac tgtcaacagc aggggggctc tgcccggcat ggtctggcag    1800
aaccgggacg tgtacctgca gggtcccatc tgggccaaaa ttcctcacac ggacggcaac    1860
tttcacccgt ctcccctgat gggcggattt ggactcaaac cccgcctcc tcaaattctc    1920
atcaaaaaca ccccggtacc tgctaatcct ccagaggtgt ttactcctgc caagtttgcc    1980
tcatttatca cgcagtacag caccggccag gtcagcgtgg agatcgagtg gaactgcag    2040
aagaaaaca gcaaacgctg gaatccagag attcagtaca cctcaaatta tgccaagtct    2100
```

```
aataatgtgg aatttgctgt caacaacgaa ggggtttata ctgagcctcg ccccattggc    2160
acccgttacc tcacccgtaa cctgtaa                                        2187

<210> SEQ ID NO 11
<211> LENGTH: 2211
<212> TYPE: DNA
<213> ORGANISM: Unknown
<220> FEATURE:
<223> OTHER INFORMATION: adeno-associated virus serotype 1 capsid

<400> SEQUENCE: 11
atggctgccg atggttatct tccagattgg ctcgaggaca acctctctga gggcattcgc      60
gagtggtggg acttgaaacc tggagccccg aagcccaaag ccaaccagca aaagcaggac     120
gacggccggg gtctggtgct tcctggctac aagtacctcg gacccttcaa cggactcgac     180 aaggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaac gtccggtaga gcagtcgcca caagagccag actcctcctc gggcatcggc     480
aagacaggcc agcagcccgc taaaaagaga ctcaatttg gtcagactgg cgactcagag     540
tcagtccccg atccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
accaccagca cccgcacctg gccttgccc acctacaata accacctcta caagcaaatc     780
tccagtgctt caacggggc cagcaacgac aaccactact cggctacag caccccctgg     840 gggtattttg atttcaacag attccactgc cacttttcac cacgtgactg cagcgactc     900 atcaacaaca attggggatt ccggcccaag agactcaact tcaaactctt caacatccaa     960
gtcaaggagg tcacgacgaa tgatggcgtc acaaccatcg ctaataacct taccagcacg    1020
gttcaagtct tctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg gcagccaagc cgtgggacgt tcatcctttt actgcctgga atatttccct    1200
tctcagatgc tgagaacggg caacaacttt accttcagct acacctttga ggaagtgcct    1260
ttccacagca gctacgcgca gcgcagagc ctggaccggc tgatgaatcc tctcatcgac    1320
caatacctgt attacctgaa cagaactcaa aatcagtccg aagtgcccca aaacaaggac    1380
ttgctgttta gccgtgggtc tccagctggc atgtctgttc agcccaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac gaagacaagt tctttcccat gagcggtgtc    1620 atgattttg aaaagagag cgccggagct tcaaacactg cattggacaa tgtcatgatt    1680
acagacgaag aggaaattaa agccactaac cctgtggcca ccgaaagatt tgggaccgtg    1740
gcagtcaatt tccagagcag cagcacagac cctgcgaccg gagatgtgca tgctatggga    1800
gcattacctg gcatggtgtg gcaagataga gacgtgtacc tgcagggtcc catttggccc    1860
aaaattcctc acacagatgg acactttcac ccgtctcctc ttatgggcgg ctttggactc    1920
```

```
aagaacccgc tcctcagat cctcatcaaa acacgcctg ttcctgcgaa tcctccggcg    1980
gagttttcag ctacaaagtt tgcttcattc atcacccaat actccacagg acaagtgagt    2040
gtggaaattg aatgggagct gcagaaagaa acagcaagc gctggaatcc cgaagtgcag    2100
tacacatcca attatgcaaa atctgccaac gttgatttta ctgtggacaa caatggactt    2160
tatactgagc ctcgccccat tggcacccgt taccttaccc gtccctgta a    2211

<210> SEQ ID NO 12
<211> LENGTH: 2211
<212> TYPE: DNA
<213> ORGANISM: Unknown
<220> FEATURE:
<223> OTHER INFORMATION: adeno-associated virus serotype 3 capsid

<400> SEQUENCE: 12
atggctgctg acggttatct tccagattgg ctcgaggaca accttctga aggcattcgt      60 gagtggtggg ctctgaaacc tggagtccct caacccaaag cgaaccaaca acaccaggac     120
aaccgtcggg tcttgtgct tccgggttac aaataccctcg acccggtaa cggactcgac     180 aaaggagagc cggtcaacga ggcggacgcg gcagccctcg aacacgacaa agcttacgac     240
cagcagctca aggccggtga caacccgtac ctcaagtaca ccacgccga cgccgagttt     300 caggagcgtc ttcaagaaga tacgtctttt ggggggcaacc ttggcagagc agtcttccag     360
gccaaaaaga ggatccttga gcctcttggt ctggttgagg aagcagctaa aacggctcct     420
ggaaagaagg gggctgtaga tcagtctcct caggaaccgg actcatcatc tggtgttggc     480
aaatcgggca acagcctgc cagaaaaaga ctaaatttcg gtcagactgg agactcagag     540
tcagtcccag accctcaacc tctcggagaa ccaccagcag cccccacaag tttgggatct     600
aatacaatgg cttcaggcgg tggcgcacca atggcagaca taacgagggg tgccgatgga     660
gtgggtaatt cctcaggaaa ttggcattgc gattcccaat ggctgggcga cagagtcatc     720
accaccagca ccagaacctg gcccctgccc acttacaaca accatctcta caagcaaatc     780
tccagccaat caggagcttc aaacgacaac cactactttg gctacagcac cccttggggg     840
tattttgact ttaacagatt ccactgccac ttctcaccac gtgactggca gcgactcatt     900
aacaacaact ggggattccg gcccaagaaa ctcagcttca gctcttcaa catccaagtt     960 agaggggtca cgcagaacga tggcacgacg actattgcca ataacctttac cagcacggtt    1020 caagtgttta cggactcgga gtatcagctc ccgtacgtgc tcgggtcggc gcaccaaggc    1080
tgtctcccgc cgtttccagc ggacgtcttc atggtccctc agtatggata cctcaccctg    1140
aacaacggaa gtcaagcggt gggacgctca tccttttact gcctggagta cttcccttcg    1200
cagatgctaa ggactggaaa taacttccaa ttcagctata ccttcgagga tgtaccttttt    1260 cacagcagct acgctcacag ccagagtttg gatcgcttga tgaatcctct tattgatcag    1320
tatctgtact acctgaacag aacgcaagga acaacctctg gaacaaccaa ccaatcacgg    1380 ctgctttta gccaggctgg gcctcagtct atgtctttgc aggccagaaa ttggctacct    1440
gggccctgct accggcaaca gagactttca aagactgcta cgacaacaa caacagtaac    1500 tttcccttgga cagcggccag caaatatcat ctcaatggcc gcgactcgct ggtgaatcca    1560
ggaccagcta tggccagtca aaggacgat gaagaaaaat tttcccctat gcacggcaat    1620
ctaatatttg gcaaagaagg gacaacggca agtaacgcag aattagataa tgtaatgatt    1680
acggatgaag aagagattcg taccaccaat cctgtggcaa cagagcagta tggaactgtg    1740
gcaaataact tgcagagctc aaatacagct cccacgactg aactgtcaa tcatcagggg    1800
```

```
gccttacctg gcatggtgtg gcaagatcgt gacgtgtacc ttcaaggacc tatctgggca   1860
aagattcctc acacggatgg acactttcat ccttctcctc tgatgggagg ctttggactg   1920
aaacatccgc ctcctcaaat catgatcaaa aatactccgg taccggcaaa tcctccgacg   1980
actttcagcc cggccaagtt tgcttcattt atcactcagt actccactgg acaggtcagc   2040
gtggaaattg agtgggagct acagaaagaa acagcaaac gttggaatcc agagattcag   2100
tacacttcca actacaacaa gtctgttaat gtggacttta ctgtagacac taatggtgtt   2160
tatagtgaac ctcgccctat tggaacccgg tatctcacac gaaacttgtg a            2211
```

<210> SEQ ID NO 13
<211> LENGTH: 2208
<212> TYPE: DNA
<213> ORGANISM: Unknown
<220> FEATURE:
<223> OTHER INFORMATION: adeno-associated virus serotype 6 capsid

<400> SEQUENCE: 13

```
atggctgccg atggttatct tccagattgg ctcgaggaca acctctctga gggcattcgc    60
gagtggtggg acttgaaacc tggagccccg aaacccaaag ccaaccagca aaagcaggac   120
gacggccggg gtctggtgct tcctggctac aagtacctcg gacccttcaa cggactcgac   180 aaggggggagc ccgtcaacgc ggcggatgca gcggccctcg agcacgacaa ggcctacgac   240
cagcagctca agcgggtgaa caatccgtac ctgcggtata accacgccga cgccgagttt   300
caggagcgtc tgcaagaaga tacgtctttt gggggcaacc tcgggcgagc agtcttccag   360
gccaagaaga gggttctcga acctttttggt ctggttgagg aaggtgctaa gacggctcct   420
ggaaagaaac gtccggtaga gcagtcgcca aagagccag actcctcctc gggcattggc   480
aagacaggcc agcagcccgc taaaaagaga ctcaattttg gtcagactgg cgactcagag   540
tcagtccccg acccacaacc tctcggagaa cctccagcaa ccccgctgc tgtgggacct   600 actacaatgg cttcaggcgg tggcgcacca atggcagaca taacgaagg cgccgacgga   660 gtgggtaatg cctcaggaaa ttggcattgc gattccacat ggctgggcga cagagtcatc   720
accaccagca cccgaacatg ggccttgccc acctataaca accacctcta caagcaaatc   780
tccagtgctt caacgggggc cagcaacgac aaccactact cggctacag cacccctggg   840 gggtattttg attcaacag attccactgc catttctcac cacgtgactg cagcgactc   900 atcaacaaca attggggatt ccggcccaag agactcaact tcaagctctt caacatccaa   960
gtcaaggagg tcacgacgaa tgatggcgtc acgaccatcg ctaataacct taccagcacg   1020
gttcaagtct ctctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atatttccca   1200
tcgcagatgc tgagaacggg caataacttt acctttcagct acaccttcga ggacgtgcct   1260
ttccacagca gctacgcgca cagccagagc ctggaccggc tgatgaatcc tctcatcgac   1320
cagtacctgt attacctgaa cagaactcag aatcagtccg gaagtgccca aaacaaggac   1380
ttgctgttta gccgggggtc tccagctggc atgtctgttc agcccaaaaa ctggctacct   1440
ggaccctgtt accggcagca gcgcgtttct aaaacaaaaa cagacaacaa caacagcaac   1500
tttacctgga ctggtgcttc aaaatataac cttaatgggc gtgaatctat aatcaaccct   1560
ggcactgcta tggcctcaca caaagacgac aaagacaagt tctttcccat gagcggtgtc   1620
```

```
atgattttg gaaaggagag cgccggagct tcaaacactg cattggacaa tgtcatgatc      1680
acagacgaag aggaaatcaa agccactaac cccgtggcca ccgaaagatt tgggactgtg      1740
gcagtcaatc tccagagcag cagcacagac cctgcgaccg gagatgtgca tgttatggga      1800
gccttacctg gaatggtgtg gcaagacaga gacgtatacc tgcagggtcc tatttgggcc      1860
aaaattcctc acacggatgg acactttcac ccgtctcctc tcatgggcgg ctttggactt      1920
aagcacccgc ctcctcagat cctcatcaaa aacacgcctg ttcctgcgaa tcctccggca      1980
gagttttcgg ctacaaagtt tgcttcattc atcacccagt attccacagg acaagtgagc      2040
gtggagattg aatgggagct gcagaaagaa acagcaaac gctggaatcc gaagtgcag      2100 tatacatcta actatgcaaa atctgccaac gttgatttca ctgtggacaa caatggactt      2160
tatactgagc ctcgccccat tggcacccgt tacctcaccc gtcccctg               2208
```

```
<210> SEQ ID NO 14
<211> LENGTH: 2214
<212> TYPE: DNA
<213> ORGANISM: Unknown
<220> FEATURE:
<223> OTHER INFORMATION: adeno-associated virus serotype 7 capsid

<400> SEQUENCE: 14
```

```
atggctgccg atggttatct tccagattgg ctcgaggaca acctctctga gggcattcgc      60
gagtggtggg acctgaaacc tggagccccg aaacccaaag ccaaccagca aaagcaggac     120
aacggccggg gtctggtgct tcctggctac aagtacctcg acccttcaa cggactcgac     180 aaggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtcattt ggggcaacc tcgggcgagc agtcttccag     360
gccaagaagc gggttctcga acctctcggt ctggttgagg aaggcgctaa gacggctcct     420
gcaaagaaga gaccggtaga gccgtcacct cagcgttccc ccgactcctc cacgggcatc     480
ggcaagaaag gccagcagcc cgccagaaag agactcaatt tcggtcagac tggcgactca     540
gagtcagtcc ccgaccctca acctctcgga gaacctccag cagcgccctc tagtgtggga     600
tctggtacag tggctgcagg cggtggcgca ccaatggcag acaataacga aggtgccgac     660
ggagtgggta tgcctcagg aaattggcat gcgattcca catggctggg cgacagagtc     720
attaccacca gcacccgaac ctgggccctg cccacctaca acaaccacct ctacaagcaa     780
atctccagtg aaactgcagg tagtaccaac gacaacacct acttcggcta cagcacccc     840 tgggggtatt ttgactttaa cagattccac tgccacttct caccacgtga ctggcagcga     900
ctcatcaaca caactggggg attccggccc aagaagctgc ggttcaagct cttcaacatc     960
caggtcaagg aggtcacgac gaatgacggc gttacgacca tcgctaataa ccttaccagc    1020
acgattcagg tattctcgga ctcggaatac cagctgccgt acgtcctcgg ctctgcgcac    1080
cagggctgcc tgcctccgtt cccggcggac gtcttcatga ttcctcagta cggctacctg    1140
actctcaaca atggcagtca gtctgtggga cgttcctcct tctactgcct ggagtacttc    1200
ccctctcaga tgctgagaac gggcaacaac tttgagttca gctacagctt cgaggacgtg    1260
cctttccaca gcagctacgc acacagccag agcctggacc ggctgatgaa tcccctcatc    1320
gaccagtact tgtactacct ggccagaaca cagagtaacc caggaggcac agctggcaat    1380
cgggaactgc agtttaccca gggcgggcct tcaactatgg ccgaacaagc caagaattgg    1440
ttacctggac cttgcttccg gcaacaaaga gtctccaaaa cgctggatca aaacaacaac    1500
```

```
agcaactttg cttggactgg tgccaccaaa tatcacctga acggcagaaa ctcgttggtt    1560
aatcccggcg tcgccatggc aactcacaag gacgacgagg accgcttttt cccatccagc    1620
ggagtcctga tttttggaaa aactggagca actaacaaaa ctacattgga aaatgtgtta    1680
atgacaaatg aagaagaaat tcgtcctact aatcctgtag ccacggaaga atacgggata    1740
gtcagcagca acttacaagc ggctaatact gcagcccaga cacaagttgt caacaaccag    1800
ggagccttac ctgcatggt ctggcagaac cgggacgtgt acctgcaggg tcccatctgg    1860
gccaagattc ctcacacgga tggcaacttt caccgtctc ctttgatggg cggctttgga    1920
cttaaacatc cgcctcctca gatcctgatc aagaacactc ccgttccgc taatcctccg    1980 gaggtgttta ctcctgccaa gtttgcttcg ttcatcacac agtacagcac cggacaagtc    2040
agcgtggaaa tcgagtggga gctgcagaag gaaaacagca gcgctggaa cccggagatt    2100 cagtacaccct ccaactttga aaagcagact ggtgtggact ttgccgttga cagccagggt    2160
gtttactctg agcctcgccc tattggcact cgttacctca cccgtaatct gtaa          2214
```

<210> SEQ ID NO 15
<211> LENGTH: 2217
<212> TYPE: DNA
<213> ORGANISM: Unknown
<220> FEATURE:
<223> OTHER INFORMATION: adeno-associated virus serotype 8 capsid

<400> SEQUENCE: 15

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg acccttcaa cggactcgac    180 aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag ccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca tggctggg cgacagagtc    720 atcaccacca gcacccgaac ctgggccctg cccacctaca acaaccacct ctacaagcaa    780
atctccaacg gacatcggg aggagccacc aacgacaaca cctacttcgg ctacagcacc    840 ccctggggt attttgactt taacagattc cactgccact tttcaccacg tgactggcag    900
cgactcatca caacaactg gggattccgg cccaagagac tcagcttcaa gctcttcaac    960
atccaggtca aggaggtcac gcagaatgaa ggcaccaaga ccatcgccaa taacctcacc    1020
agcaccatcc aggtgtttac ggactcggag taccagctgc cgtacgttct cggctctgcc    1080
caccagggct gcctgcctcc gttcccggcg gacgtgttca tgattcccca gtacggctac    1140
ctaacactca acaacggtag tcaggccgtg ggacgctcct ccttctactg cctggaatac    1200
tttccttcgc agatgctgag aaccggcaac aacttccagt ttacttacac cttcgaggac    1260
gtgcctttcc acagcagcta cgcccacagc cagagcttgg accggctgat gaatcctctg    1320
```

| | |
|---|---|
| attgaccagt acctgtacta cttgtctcgg actcaaacaa caggaggcac ggcaaatacg | 1380 |
| cagactctgg gcttcagcca aggtgggcct aatacaatgg ccaatcaggc aaagaactgg | 1440 |
| ctgccaggac cctgttaccg ccaacaacgc gtctcaacga caaccgggca aaacaacaat | 1500 |
| agcaactttg cctggactgc tgggaccaaa taccatctga atggaagaaa ttcattggct | 1560 |
| aatcctggca tcgctatggc aacacacaaa gacgacgagg agcgtttttt tcccagtaac | 1620 |
| gggatcctga tttttggcaa acaaaatgct gccagagaca atgcggatta cagcgatgtc | 1680 |
| atgctcacca gcgaggaaga aatcaaaacc actaaccctg tggctacaga ggaatacggt | 1740 |
| atcgtggcag ataacttgca gcagcaaaac acggctcctc aaattggaac tgtcaacagc | 1800 |
| cagggggcct acccggtat ggtctggcag aaccgggacg tgtacctgca gggtcccatc | 1860 |
| tgggccaaga ttcctcacac ggacggcaac ttccacccgt ctccgctgat gggcggcttt | 1920 |
| ggcctgaaac atcctccgcc tcagatcctg atcaagaaca cgcctgtacc tgcggatcct | 1980 |
| ccgaccacct tcaaccagtc aaagctgaac tctttcatca cgcaatacag caccggacag | 2040 |
| gtcagcgtgg aaattgaatg ggagctgcag aaggaaaaca gcaagcgctg gaaccccgag | 2100 |
| atccagtaca cctccaacta ctacaaatct acaagtgtgg actttgctgt taatacagaa | 2160 |
| ggcgtgtact ctgaaccccg ccccattggc acccgttacc tcacccgtaa tctgtaa | 2217 |

<210> SEQ ID NO 16
<211> LENGTH: 2208
<212> TYPE: DNA
<213> ORGANISM: Unknown
<220> FEATURE:
<223> OTHER INFORMATION: adeno-associated virus, hu.13 capsid

<400> SEQUENCE: 16

| | |
|---|---|
| atggctgccg atggttatct tccagattgg ctcgaggaca ctctctctga aggaataaga | 60 |
| cagtggtgga agctcaaacc tggccccacca ccaccaaagc ccgcagagcg gcataaggac | 120 |
| gacagcaggg tcttgtgct tcctgggtac aagtacctcg acccttcaa cggactcgac | 180 |
| aagggagagc cggtcaacga ggcagacgcc gcggccctcg agcacgacaa ggcctacgac | 240 |
| cggcagctcg acagcggaga caaccccgtac ctcaagtaca accacgccga cgcggagttt | 300 |
| caggagcgcc ttaaagaaga tacgtctttt gggggcaacc tcggacgagc agtcttccag | 360 |
| gcaaaaagga gggttcttga acctctgggc ctggttgagg agcctgttaa acgggctccg | 420 |
| ggaaaaaga ggccggtaga gcactctcct gcggagccag actcctcctc gggaaccgga | 480 |
| aaagcgggcc agcagcctgc aagaaaaaga ttgaatttcg gtcagactgg agacgcagac | 540 |
| tccgtacctg accccagcc tctcggacag ccaccagcag cccctctgg tctgggaact | 600 |
| aatacgatgg cttcaggcag tggcgcacca atgcagacaa taacgagggg cgccgacgga | 660 |
| gtgggtaatt cctcgggaaa ttggcattgc gattccacat ggatgggcga cagagtcatc | 720 |
| accaccagca cccgaacttg gccctgccc acctacaaca accatctcta caagcaaatc | 780 |
| tccagccaat caggagccag caacgacaac cactactttg gctacagcac cccttggggg | 840 |
| tattttgact tcaacagatt ccactgccac ttttcaccac gtgactggca aagactcatc | 900 |
| aacaacaact gggggattcg gcccaagaga ctcaacttca agctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga gtcaggcagt aggacgctct ctcattttact gcctggagta ctttccttct | 1200 |

```
cagatgctgc gtaccggaaa caactttacc ttcagctaca cctttgagga cgttcctttc    1260
cacagcagct acgctcacag ccagagtttg gaccgtctca tgaatcctct catcgaccag    1320
tacctgtatt acttgagcag aacaaacact ccaagcggaa ccaccacgca gtccaggctt    1380
cagttttctc aggccggagc aagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg ccagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac caccaatccc gtggctacgg agcagtatgg ttctgtatct    1740
accaacctgc agggcggcaa cacacaagca gctaccgcag atgtcaacac acaaggcgtt    1800
cttccaggca tggtctggca ggacagagac gtgtacctgc aggggcccat ctgggcaaag    1860
attccacaca cggacggaca ttttcacccc tctcccctca tgggcggatt cggacttaaa    1920
cacccctcct cacagattct catcaagaac accccggtac ctgcgaatcc ttcgaccacc    1980
ttcagtgcgg caaagtttgc ttctttcatc acacagtatt ccacggggca ggtcagcgtg    2040
gagatcgagt gggagctgca gaaggagaac agcaaacgct ggaatcccga gatccagtac    2100
acttccaact acaacaaatc tgttaatgtg gactttactg ttgacactaa tggcgtgtat    2160
tcagagcctc gccccattgg caccagatac ctgactcgta atctgtaa                 2208

<210> SEQ ID NO 17
<211> LENGTH: 2208
<212> TYPE: DNA
<213> ORGANISM: Unknown
<220> FEATURE:
<223> OTHER INFORMATION: adeno-associated virus, hu.26 capsid

<400> SEQUENCE: 17
atggctgccg atggttatct tccagattgg ctcgaggaca ctctctctga aggaataaga    60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgcc gcggccctcg agcacgacaa ggcctacgac    240
cggcagctcg acagcggaga caacccgtac ctcaagtaca accacgccga cgcggagttt    300
caggagcgtc ttaaagaaga tacgtctttt gggggcaacc tcggacgagc agtcttccag    360
gccaaaaaga ggattcttga acctctgggc ctggttgagg aacctgttaa gacggctccg    420
ggaaaaaaga ggccggtaga gcactctcct gcggagccag actcctcctc gggaaccgga    480
aaagcgggcc agcagcctgc aagaaagaga ttgaattttg gtcagactgg agacgcagac    540
tcagtacctg accccagcc tctcggacag ccaccagcag cccctctgg tctgggaact    600 aatacgatgg cttcaggcag tggcgcacca atggcagaca ataacgaggg cgccgacgga    660
gtgggtaatt cctcgggaaa ttggcattgc gattccacat ggatgggcga cagagtcatc    720
accaccagca cccgcacctg ggccctgccc acctacaaca accatctgta caagcaaatc    780
tccagccagt ctggagccag caacgacaac cactactttg gctacagcac ccctggggg    840 tattttgact tcaacagatt ccactgccac ttctccccac gtgactggca aagactcatc    900
aacaacaact ggggattccg gcccaagaga ctcagcttca agctctttaa cattcaagtc    960
aaagaggtca cgcagaatga cggtacgacg acgattgcca ataaccttac cagcacggtt    1020
```

```
caggtgttta ctgactcgga gtaccagctc ccgtacgtcc tcggctcggc gcatcaagga    1080
tgcctcccgc cgttcccagc agacgtcttc atggtgccac agtatggata cctcaccctg    1140
aacaacggca gtcaggcggt aggacgctct tcctttact gcctggagta ctttccttct     1200
cagatgcttc gtaccggaaa caactttacc ttcagctaca cctttgaaga cgttcctttc    1260
catagcagct acgctcacag ccaaagtctg daccgtctca tgaatcctct catcgaccag    1320
tacctgtatt acttgagcag aacaaacact ccaagcggaa ccaccacgat gtccaggctt    1380 cagtttctc aggccggagc aagtgacatt cggaccagt ctagaaactg gcttcctgga      1440
ccctgttacc gccagcagcg agtatcaaag acagctgcgg acaacaacaa cagtgattac    1500
tcgtggactg gagctaccaa gtaccacctc aatggaagag actctctggt gaatccgggc    1560
ccagctatgg ccagccacaa ggacgatgaa gaaaaatatt tccctcagag cggggttctc    1620
atctttggaa acaagactc gggaaaaact aatgtggaca ttgaaaaggt tatgattaca     1680
gacgaagagg aaatcaggac caccaatccc gtggctacgg agcagtatgg ttctgtatct    1740
accaacctcc agagcggcaa cacacaagca gctacctcag atgtcaacac acaaggcgtt    1800
cttccaggca tggtctggca ggacagagac gtgtacctgc aggggcccat ctgggcaaag    1860
attccacaca cggacggaca ttttcacccc ctcccctca tgggcggatt cggacttaaa     1920
caccctcctc acaaattct catcaagaac accccggtac ctgcgaatcc ttcgaccact    1980
ttcagtgcgg caaagtttgc ttccttcatc acacagtact ccacggggca ggtcagcgtg    2040
gagatcgagt gggagctgca gaaggagaac agcaaacgct ggaatccga aattcagtac    2100 acttccaact acaacaaatc tgttaatgtg gactttactg tggacactaa tggtgtgtat    2160
tcagagcctc gccccattgg caccagatac ctgactcgta atctgtaa                 2208

<210> SEQ ID NO 18
<211> LENGTH: 2217
<212> TYPE: DNA
<213> ORGANISM: Unknown
<220> FEATURE:
<223> OTHER INFORMATION: adeno-associated virus, hu.37 capsid

<400> SEQUENCE: 18
atggctgctg acggttatct tccagattgg ctcgaggaca acctctctga gggcattcgc     60
gagtggtggg acctgaaacc tggagccccc aagcccaagg ccaaccagca gaagcaggac    120
gacggccggg gtctggtgct tcctggctac aagtaccctcg gacccttcaa cggactcgac    180 aaggggagc ccgtcaacgc ggcggacgca gcggccctcg agcacgacaa ggcctacgac    240
cagcagctca aagcgggtga caatccgtac ctgcggtata ccacgccga cgccgagttt    300 caggagcgtc tgcaagaaga tacgtctttt ggggcaacc tcgggcgagc agtcttccag    360
gccaagaagc gggttctcga acctctcggt ctggttgagg aagctgctaa gacggctcct    420
ggaaagaaga ccggtaga accgtcacct cagcgttccc ccgactcctc cacgggcatc    480
ggcaagaaag ccagcagcc cgctaaaaag agactgaact tggtcagac tggcgactca    540 gagtcagtcc ccgaccctca accaatcgga gaaccaccag caggcccctc tggtctggga    600
tctggtacaa tggctgcagg cggtggcgct ccaatggcag acaataacga aggcgccgac    660
ggagtgggta gttcctcagg aaattggcat gcgattcca catggctggg cgacagagtc    720
atcaccacca gcacccgaac ctgggccctg cccacctaca acaaccacct ctacaagcaa    780
atatccaatg gacatcggg aggaagcacc aacgacaaca cctacttcgg ctacagcacc    840
ccctgggggt atttttgactt caacagattc cactgccact tctcaccacg tgactggcag    900
```

```
cgactcatca acaacaactg gggattccgg ccaaaaagac tcagcttcaa gctcttcaac    960
atccaggtca aggaggtcac gcagaatgaa ggcaccaaga ccatcgccaa taaccttacc   1020
agcacgattc aggtatttac ggactcggaa taccagctgc cgtacgtcct cggctccgcg   1080
caccagggct gcctgcctcc gttcccggcg gacgtcttca tgattcccca gtacggctac   1140
cttacactga caatggaag tcaagccgta ggccgttcct ccttctactg cctggaatat    1200
tttccatctc aaatgctgcg aactggaaac aattttgaat tcagctacac cttcgaggac   1260
gtgcctttcc acagcagcta cgcacacagc cagagcttgg accgactgat gaatcctctc   1320
atcgaccagt acctgtacta cttatccaga actcagtcca caggaggaac tcaaggtacc   1380
cagcaattgt tattttctca agctgggcct gcaaacatgt cggctcaggc taagaactgg   1440
ctacctggac cttgctaccg gcagcagcga gtctctacga cactgtcgca aaacaacaac   1500
agcaactttg cttggactgg tgccaccaaa tatcacctga acggaagaga ctctttggta   1560
aatcccggtg tcgccatggc aacccacaag gacgacgagg aacgcttctt cccgtcgagt   1620
ggagtcctga tgttcggaaa acagggtgct ggaagagaca atgtggacta cagcagcgtt   1680
atgctaacca gcgaagaaga aattaaaacc actaaccccg tagccacaga acaatacggt   1740
gtggtggctg acaacttgca gcaaaccaat acagggccta ttgtgggaaa tgtcaacagc   1800
caaggagcct tacctggcat ggtctggcag aaccgagacg tgtacctgca gggtcccatc   1860
tgggccaaga ttcctcacac ggacggcaac ttccacccct taccgctaat gggaggattt   1920
ggactgaagc acccacctcc tcagatcctg atcaagaaca gccggtacc tgcggatcct   1980 ccaacaacgt tcagccaggc gaaattggct tccttcatta cgcagtacag caccggacag   2040
gtcagcgtgg aaatcgagtg ggagctgcag aaggagaaca gcaaacgctg gaacccagag   2100
attcagtaca cttcaaacta ctacaaatct acaaatgtgg actttgctgt caatacagag   2160
ggaacttatt ctgagcctcg ccccattggt actcgttacc tcacccgtaa tctgtaa     2217
```

<210> SEQ ID NO 19
<211> LENGTH: 2205
<212> TYPE: DNA
<213> ORGANISM: Unknown
<220> FEATURE:
<223> OTHER INFORMATION: adeno-associated virus, hu.53 capsid

<400> SEQUENCE: 19

```
atggctgccg atggttatct tccagattgg ctcgaggaca ctctctctga aggaataaga    60
cagtggtgga agctcaaacc tggcccacca ccaccaaagc ccgcagagcg gcataaggac   120
gacagcaggg gtcttgtgct tcctgggtac aagtacctcg gacccttcaa cggactcgac   180
aagggagagc cggtcaacga ggcagacgcc gcggccctcg agcacgacaa ggcctacgac   240
cggcagctcg acagcggaga caacccgtac ctcaagtaca accacgccga cgcggagttt   300
caggagcgtc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gcggagccag actcctcctc gggaaccgga   480
aaagcgggcc agcagcctgc aagaaaaaga ctgaatttcg gtcagactgg agacgcagac   540
tccgtacctg accccagcc tctcagacag ccaccagcag ccccacaag tttgggatct   600 actacaatgg ctacaggcag tggcgcacca atggcagaca taacgagggg tgccgatgga   660
gtgggtaatt cctcaggaaa ttggcattgc gattcccaat ggctgggcga cagagtcatc   720
```

```
accaccagca cccgaacctg ggccctgccc acctacaaca accacctttta caagcaaatc    780 tccagccaat caggagcctc aaacgacaac cactactttg ctacagcac ccctgggg       840 tattttgact tcaacagatt ccactgccac ttttcaccac gtgactggca aagactcatc    900
aacaacaact ggggattccg acccaagaga ctcaacttca agctctttaa cattcaagtc    960
aaagaggtca cgcagaatga cggtacgacg acgattgcca ataaccttac cagcacggtt   1020
caggtgttta ctgactcgga gtaccagctc ccgtacgtcc tcggctcggc gcatcaagga   1080
tgcctcccgc cgtttccagc ggacgtcttc atggtcccac agtatggata cctcacctg    1140 aacaacggga gtcaggcggt aggacgctct tccttttact gcctggagta ctttccttct   1200
cagatgctgc gtactggaaa caactttcag ttcagctaca cttttgaaga cgtgcctttc   1260
cacagcagct acgctcacag ccagagtttg atcggctga tgaatcctct gatcgaccag    1320
tacctgtatt atctaaacag aacacaaaca gctagtggaa ctcagcagtc tcggctactg   1380
tttagccaag ctggacccac aagcatgtct cttcaagcta aaaactggct gcctggaccg   1440
tgttatcgcc agcagcgttt gtcaaagcag gcaaacgaca caacaacag caactttccc    1500 tggactggag ctaccaagta ctacctcaat ggcagagact cttttggtgaa cccgggcccg   1560 gccatggcca ccacaagga cgatgaagaa agttttttcc ccatgcatgg aaccctaata    1620
tttggtaaag aaggaacaaa tgctaccaac gcggaattgg aaaatgtcat gattacagat   1680
gaagaggaaa tcaggaccac caatcccgtg gctacagagc agtacggata tgtgtcaaat   1740
aatttgcaaa actcaaatac tgctgcaagt actgaaactg tgaatcacca aggagcatta    1800
cctggtatgg tgtggcagga tcgagacgtg tacctgcagg gacccatttg gccaagatt    1860 cctcacaccg atggacactt tcatccttct ccactgatgg aggttttgg actcaaacac    1920 ccgcctcctc agattatgat caaaaacact cccgttccag ccaatcctcc cacaaacttc    1980
agttctgcca gtttgcttc cttcatcaca cagtattcca cgggacaggt cagcgtggag    2040
atcgagtggg agctgcagaa ggagaacagc aaacgctgga atcccgaaat tcagtacact   2100
tccaactaca caaatctgt taatgtggac tttactgtgg acactaatgg tgtgtattca   2160
gagcctcgcc ccattggcac cagatacctg actcgtaatc tgtaa                   2205
```

<210> SEQ ID NO 20
<211> LENGTH: 2217
<212> TYPE: DNA
<213> ORGANISM: Unknown
<220> FEATURE:
<223> OTHER INFORMATION: rhesus adeno-associated virus, rh.39 capsid

<400> SEQUENCE: 20

```
atggctgctg acggttatct tccagattgg ctcgaggaca acctctctga gggcattcgc    60
gagtggtggg acctgaaacc tggagccccc aagcccaagg ccaaccagca gaagcaggac   120 gacgcgggg gtctggtgct tcctggctac aagtacctcg accccttcaa cggactcgac   180 aaggggagc ccgtcaacgc ggcggacgca gcggccctcg agcacgacaa ggcctacgac   240
cagcagctca aagcgggtga caatccgtac ctgcggtata accacgccga cgccgagttt   300
caggagcgtc tgcaagaaga tacgtctttt ggggcaacc tcgggcgagc agtcttccag    360
gccaagaagc gggttctcga acctctcggt ctggttgagg aagctgctaa gacggctcct   420
ggaaagaaga gaccggtaga accgtcacct cagcgttccc ccgactcctc acgggcatc    480 ggcaagaaag ccagcagcc cgctaaaaag agactgaact ttggtcagac tggcgactca    540
gagtcagtcc ccgaccctca accaatcgga gaaccaccag caggcccctc tggtctggga    600
```

```
tctggtacaa tggctgcagg cggtggcgct ccaatggcag acaataacga aggcgccgac      660
ggagtgggta gttcctcagg aaattggcat tgcgattcca catggctggg cgacagagtc      720
atcaccacca gcacccgaac ctgggccctg cccacctaca caaccaccct ctacaagcaa      780
atatccaatg ggacatcggg aggaagcacc aacgacaaca cctacttcgg ctacagcacc      840
ccctgggggt attttgactt caacagattc cactgccact tctcaccacg tgactggcag      900
cgactcatca caacaactg gggattccgg ccaaaaagac tcagcttcaa gctcttcaac      960
atccaggtca aggaggtcac gcagaatgaa ggcaccaaga ccatcgccaa taaccttacc     1020
agcacgattc aggtatttac ggactcggaa taccagctgc cgtacgtcct cggctccgcg     1080
caccagggct gcctgcctcc gttcccggcg gacgtcttca tgattcccca gtacggctac     1140
cttacactga caatggaag tcaagccgta ggccgttcct ccttctactg cctgaatat     1200
tttccatctc aaatgctgcg aactggaaac aattttgaat tcagctacac cttcgaggac     1260
gtgcctttcc acagcagcta cgcacacagc cagagcttgg accgactgat gaatcctctc     1320
atcgaccagt acctgtacta cttatccaga actcagtcca caggaggaac tcaaggtacc     1380
cagcaattgt tatttctca agctgggcct gcaaacatgt cggctcaggc taagaactgg     1440
ctacctggac cttgctaccg gcagcagcga gtctctacga cactgtcgca aacaacaac     1500
agcaactttg cttggactgg tgccaccaaa tatcacctga acggaagaga ctctttggta     1560
aatcccggtg tcgccatggc aaacccacaa gacgacgagg aacgcttctt cccgtcgagt     1620
ggagtcctga tgtttggaaa acagggtgct ggaagagaca atgtggacta cagcagcgtt     1680
atgctaacca gcgaagaaga aattaaaacc actaaccctg tagccacaga acaatacggt     1740
gtggtggctg ataacttgca gcaaaccaat acggggccta ttgtgggaaa tgtcaacagc     1800
caaggagcct tacctggcat ggtctggcag aaccgagacg tgtacctgca gggtcccatc     1860
tgggccaaga ttcctcacac ggacggcaac ttccacccct taccgctaat gggaggattt     1920
ggactgaagc acccacctcc tcagatcctg atcaagaaca cgccggtacc tgcggatcct     1980
ccaacaacgt tcagccaggc gaaattggct tccttcatta cgcagtacag caccggacag     2040
gtcagcgtgg aaatcgagtg ggagctgcag aaggagaaca gcaaacgctg gaacccagag     2100
attcagtaca cttcaaacta ctacaaatct acaaatgtgg actttgctgt caatacagag     2160
ggaacttatt ctgagcctcg cccccattgg actcgttacc tcacccgtaa tctgtaa      2217
```

<210> SEQ ID NO 21
<211> LENGTH: 2211
<212> TYPE: DNA
<213> ORGANISM: Unknown
<220> FEATURE:
<223> OTHER INFORMATION: rhesus adeno-associated virus, 43 capsid

<400> SEQUENCE: 21

```
atggctgccg atggttatct tccagattgg ctcgaggaca acctctctga gggcattcgc       60
gagtggtggg acttgaaacc tggagccccg aaacccaaag ccaaccagca aaagcaggac      120
gacggccggg gcctggtgct tcctggctac aagtacctcg acccttcaa cggactcgac      180
aagggggagc ccgtcaacgc ggcggacgca gcggccctcg agcacgacaa ggcctacgac      240
cagcagctcg aagcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
```

```
ggaaagaaga gaccagtaga gcagtcaccc caagaaccag actcctcctc gggcatcggc      480
aagaaaggcc aacagcccgc cagaaaaaga ctcaattttg gccagactgg cgactcagag      540
tcagttccag accctcaacc tctcggagaa cctccagcag cgccctctgg tgtgggacct      600
aatacaatgg ctgcaggcgg tggcgcacca atggcagaca taacgaagg cgccgacgga       660 gtgggtagtt cctcgggaaa ttggcattgc gattccacat ggctgggcga cagagtcatc      720
accaccagca cccgaacctg ggccctgccc acctacaaca accacctcta caagcaaatc      780
tccaacggga catcgggagg agccaccaac acaacacct acttcggcta cagcaccccc       840
tgggggtatt ttgactttaa cagattccac tgccactttt caccacgtga ctggcagcga      900
ctcatcaaca caactgggg attccggccc aagagactca gcttcaagct cttcaacatc       960
caggtcaagg aggtcacgca gaatgaaggc accaagacca tcgccaataa cctcaccagc     1020
accatccagg tgtttacgga ctcggagtac cagctgccgt acgttctcgg ctctgcccac     1080
cagggctgcc tgcctccgtt cccggcggac gtgttcatga ttccccagta cggctaccta     1140
acactcaaca acggtagtca ggccgtggga cgctcctcct tctactgcct ggaatacttt     1200
ccttcgcaga tgctgagaac cggcaacaac ttccagttta cttacacctt cgaggacgtg     1260
cctttccaca gcagctacgc ccacagccag agcttggacc ggctgatgaa tcctctgatt     1320
gaccagtacc tgtactactt gtctcggact caaacaacag gaggcacggc aaatacgcag     1380
actctgggct tcagccaagg tgggcctaat acaatggcca tcaggcaaa gaactggctg      1440 ccaggaccct gttaccgcca acaacgcgtc tcaacgacaa ccgggcaaaa caacaatagc     1500
aactttgcct ggactgctgg gaccaaatac catctgaatg gaagaaattc attggctaat     1560
cctggcatcg ctatggcaac acacaaagac gacgaggagc gttttttccc agtaacggga     1620
tcctgttttt ggcaacaaaa tgctgccaga gacaatgcgg attacagcga tgtcatgctc     1680
accagcgagg aagaaatcaa aaccactaac cctgtggcta cagaggaata cggtatcgtg     1740
gcagataact tgcagcagca aaacacggct cctcaaattg gaactgtcaa cagccagggg     1800
gccttacccg gtatggtctg gcagaaccgg gacgtgtacc tgcagggtcc catctgggcc     1860
aagattcctc acacgacgg caacttccac cgtctccgc tgatgggcgg ctttggcctg       1920
aaacatcctc cgcctcagat cctgatcaag aacacgcctg tacctgcgga tcctccgacc     1980
accttcaacc agtcaaagct gaactctttc atcacgcaat acagcaccgg acaggtcagc     2040
gtggaaattg aatgggagct acagaaggaa aacagcaagc gctggaaccc cgagatccag     2100
tacacctcca actactacaa atctacaagt gtggactttg ctgttaatac agaaggcgtg     2160
tactctgaac cccgccccat tggcacccgt tacctcaccc gtaatctgta a              2211
```

<210> SEQ ID NO 22  
<211> LENGTH: 2217  
<212> TYPE: DNA  
<213> ORGANISM: Unknown  
<220> FEATURE:  
<223> OTHER INFORMATION: rhesus adeno-associated virus 46 capsid

<400> SEQUENCE: 22

```
atggctgccg atggttatct tccagattgg ctcgaggaca acctctctga gggcattcgc       60
gagtggtggg acctgaaacc tggagcccg aaacccaaag ccaaccagca aaagcaggac       120
gacggccggg gtctggtgct tcctggctac aagtacctcg accccttcaa cggactcgac      180 aaggggggagc ccgtcaacgc ggcggacgca gcggccctcg agcacgacaa ggcctacgac      240
cagcagctca agcgggtga caatccgtac ctgcggtata atcacgccga cgccgagttt      300
```

| | |
|---|---|
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaga gaccggtaga gccgtcacca cagcgttccc ccgactcctc cacgggcatc | 480 |
| ggcaagaaag gccagcagcc cgccagaaag agactcaatt tcggtcagac tggcgactca | 540 |
| gagtcagtcc ccgaccctca acctatcgga gaacctccag cagcgccctc tagtgtggga | 600 |
| tctggtacaa tggctgcagg cggtggcgca ccaatggcag acaataacga aggtgccgac | 660 |
| ggagtgggta gttcctcggg aaattggcat gcgattcca catggctggg cgacagagtc | 720 |
| atcaccacca gcacccgaac ctgggccctg cccacctaca caaccaccct ctacaagcaa | 780 |
| atctccaacg gacctcggg aggcagcacc aacgacaaca cctactttgg ctacagcacc | 840 |
| ccctgggggt attttgactt taacagattc cactgccact tctcaccacg tgactggcag | 900 |
| cgactcatca acaacaactg gggattccgg cccaagagac tcagcttcaa gctcttcaac | 960 |
| atccaggtca agaggtcac gcagaatgaa ggcaccaaga ccatcgccaa taacctcacc | 1020 |
| agcaccatcc aggtgtttac ggactcggaa taccagctgc cgtacgtcct cggctctgcc | 1080 |
| caccagggct gcctgcctcc gttcccggcg gacgtcttca tgattcctca gtacggctac | 1140 |
| ctgactctca acaacggtag tcaggccgtg gacgttcct ccttctactg cctggagtac | 1200 |
| ttccctctc agatgctgag aacgggcaac aactttttcct tcagctacac tttcgaggac | 1260 |
| gtgcctttcc acagcagcta cgcgcacagc cagagtttgg acaggctgat gaatcctctc | 1320 |
| atcgaccagt acctgtacta cctgtcaaga acccagtcta cgggaggcac agcgggaacc | 1380 |
| cagcagttgc tgtttttctca ggccgggcct agcaacatgt cggctcaggc cagaaactgg | 1440 |
| ctgcctggac cctgctacag acagcagcgc gtctccacga cactgtcgca aaacaacaac | 1500 |
| agcaactttg cctggactgg tgccaccaag tatcatctga acggcagaga ctctctggtg | 1560 |
| aatccgggcg tcgccatggc aaccaacaag gacgacgagg accgcttctt cccatccagc | 1620 |
| ggcatcctca tgtttggcaa gcagggagct ggaaaagaca acgtggacta tagcaacgtg | 1680 |
| atgctaacca gcgaggaaga aatcaaggcc accaaccccg tggccacaga acagtatggc | 1740 |
| gtggtggctg ataacctaca gcagcaaaac accgctccta ttgtgggggc cgtcaacagc | 1800 |
| cagggagcct acctggcat ggtctggcag aaccgggacg tgtacctgca gggtcctatt | 1860 |
| tgggccaaga ttcctcacac agatggcaac tttcacccgt ctccttaat gggcggcttt | 1920 |
| ggacttaaac atccgcctcc tcagatcctc atcaaaaaca ctcctgttcc tgcggatcct | 1980 |
| ccaacagcgt tcaaccaggc caagctgaat tctttcatca cgcagtacag caccggacaa | 2040 |
| gtcagcgtgg agatcgagtg ggagctgcag aaggagaaca gcaagcgctg gaacccagag | 2100 |
| attcagtata cttccaacta ctacaaatct acaaatgtgg actttgctgt taatactgag | 2160 |
| ggtgtttact ctgagcctcg ccccattggc actcgttacc tcacccgtaa tctgtaa | 2217 |

<210> SEQ ID NO 23
<211> LENGTH: 735
<212> TYPE: PRT
<213> ORGANISM: Unknown
<220> FEATURE:
<223> OTHER INFORMATION: capsid protein of adeno-associated virus
      serotype 2

<400> SEQUENCE: 23

Met Ala Ala Asp Gly Tyr Leu Pro Asp Trp Leu Glu Asp Thr Leu Ser
1               5                   10                  15

-continued

```
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
```

435                 440                 445
Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                    485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                    565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                    645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                    725                 730                 735

<210> SEQ ID NO 24
<211> LENGTH: 728
<212> TYPE: PRT
<213> ORGANISM: Unknown
<220> FEATURE:
<223> OTHER INFORMATION: capsid protein of cy.5

<400> SEQUENCE: 24

Met Ala Ala Asp Gly Tyr Leu Pro Asp Trp Leu Glu Gly Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Arg Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp

-continued

```
                65                  70                  75                  80
Lys Gln Leu Glu Gln Gly Asp Asn Pro Tyr Leu Lys Tyr Asn His Ala
                    85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Gly Ala Lys Thr Ala Pro Gly Lys Lys Arg
        130                 135                 140
Pro Ile Glu Ser Pro Asp Ser Ser Thr Gly Ile Gly Lys Asn Gly Gln
145                 150                 155                 160
Pro Pro Ala Lys Lys Lys Leu Asn Phe Gly Thr Gly Asp Ser Glu
                165                 170                 175
Ser Val Pro Asp Pro Gln Pro Leu Gly Glu Pro Ala Ala Pro Ser
            180                 185                 190
Gly Leu Gly Ser Gly Thr Met Ala Ala Gly Gly Ala Pro Met Ala
        195                 200                 205
Asp Asn Asn Glu Gly Ala Asp Gly Val Gly Asn Ala Ser Gly Asn Trp
210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
        275                 280                 285
Pro Arg Asp Trp Gln Arg Leu Ile Asn Asn Asn Trp Gly Phe Arg Pro
    290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
    370                 375                 380
Arg Ser Ser Phe Tyr Cys Leu Glu Tyr Phe Pro Ser Gln Met Leu Arg
385                 390                 395                 400
Thr Gly Asp Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
    450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
```

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 25
<211> LENGTH: 738
<212> TYPE: PRT
<213> ORGANISM: Unknown
<220> FEATURE:
<223> OTHER INFORMATION: capsid protein of rhesus adeno-associated
      virus, 10

<400> SEQUENCE: 25

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro

```
            115                 120                 125
Leu Gly Leu Val Glu Glu Gly Ala Lys Thr Ala Pro Gly Lys Lys Arg
            130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                    165                 170                 175
Thr Gly Asp Ser Glu Ser Val Pro Asp Pro Gln Pro Ile Gly Glu Pro
                180                 185                 190
Pro Ala Gly Pro Ser Gly Leu Gly Ser Gly Thr Met Ala Ala Gly Gly
            195                 200                 205
Gly Ala Pro Met Ala Asp Asn Asn Glu Gly Ala Asp Gly Val Gly Ser
        210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                    245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
            275                 280                 285
Arg Phe His Cys His Phe Ser Pro Arg Asp Trp Gln Arg Leu Ile Asn
        290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                    325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
        370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                    405                 410                 415
Gln Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
        450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                    485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
        530                 535                 540
```

-continued

```
Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 26
<211> LENGTH: 728
<212> TYPE: PRT
<213> ORGANISM: Unknown
<220> FEATURE:
<223> OTHER INFORMATION: capsid protein of rhesus adeno-associated
      virus,13

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160
```

```
Gln Pro Ala Lys Lys Leu Asn Phe Gly Gln Thr Gly Asp Ser Glu
            165                 170                 175

Ser Val Pro Asp Pro Gln Pro Leu Gly Glu Pro Ala Ala Pro Ser
            180                 185                 190

Gly Leu Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Ser Thr
225                 230                 235                 240

Arg Thr Trp Ala Leu Pro Thr Tyr Asn Asn His Leu Tyr Lys Gln Ile
                    245                 250                 255

Ser Ser Gln Ser Gly Ala Thr Asn Asp Asn His Phe Phe Gly Tyr Ser
                260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Asn Trp Gly Phe Arg Pro
            290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                    325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
            370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                    405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                    485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Glu Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575
```

-continued

```
Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 27
<211> LENGTH: 736
<212> TYPE: PRT
<213> ORGANISM: Unknown
<220> FEATURE:
<223> OTHER INFORMATION: capsid protein of adeno-associated virus
      serotype 1

<400> SEQUENCE: 27

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205
```

```
Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
    515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
    595                 600                 605

Asp Arg Asp Val Tyr Leu Gln Gly Pro Ile Trp Ala Lys Ile Pro His
610                 615                 620
```

```
Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 28
<211> LENGTH: 736
<212> TYPE: PRT
<213> ORGANISM: Unknown
<220> FEATURE:
<223> OTHER INFORMATION: capsid protein of adeno-associated virus
      serotype 3

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
    515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 29
<211> LENGTH: 736
<212> TYPE: PRT
<213> ORGANISM: Unknown
<220> FEATURE:
<223> OTHER INFORMATION: capsid protein of adeno-associated virus
      serotype 6

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300
```

```
Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720
```

Tyr Thr Glu Pro Arg Pro Ile Gly Thr Arg Tyr Leu Thr Arg Pro Leu
            725                 730                 735

<210> SEQ ID NO 30
<211> LENGTH: 737
<212> TYPE: PRT
<213> ORGANISM: Unknown
<220> FEATURE:
<223> OTHER INFORMATION: capsid protein of adeno-associated virus
      serotype 7

<400> SEQUENCE: 30

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

```
                Pro Tyr Val Leu Gly Ser Ala His Gln Gly Cys Leu Pro Phe Pro
                            355                 360                 365
                Ala Asp Val Phe Met Ile Pro Gln Tyr Gly Tyr Leu Thr Leu Asn Asn
                370                 375                 380
                Gly Ser Gln Ser Val Gly Arg Ser Ser Phe Tyr Cys Leu Glu Tyr Phe
                385                 390                 395                 400
                Pro Ser Gln Met Leu Arg Thr Gly Asn Asn Phe Glu Phe Ser Tyr Ser
                                405                 410                 415
                Phe Glu Asp Val Pro Phe His Ser Ser Tyr Ala His Ser Gln Ser Leu
                            420                 425                 430
                Asp Arg Leu Met Asn Pro Leu Ile Asp Gln Tyr Leu Tyr Tyr Leu Ala
                        435                 440                 445
                Arg Thr Gln Ser Asn Pro Gly Gly Thr Ala Gly Asn Arg Glu Leu Gln
                    450                 455                 460
                Phe Tyr Gln Gly Gly Pro Ser Thr Met Ala Glu Gln Ala Lys Asn Trp
                465                 470                 475                 480
                Leu Pro Gly Pro Cys Phe Arg Gln Gln Arg Val Ser Lys Thr Leu Asp
                                485                 490                 495
                Gln Asn Asn Asn Ser Asn Phe Ala Trp Thr Gly Ala Thr Lys Tyr His
                            500                 505                 510
                Leu Asn Gly Arg Asn Ser Leu Val Asn Pro Gly Val Ala Met Ala Thr
                        515                 520                 525
                His Lys Asp Asp Glu Asp Arg Phe Phe Pro Ser Ser Gly Val Leu Ile
                    530                 535                 540
                Phe Gly Lys Thr Gly Ala Thr Asn Lys Thr Thr Leu Glu Asn Val Leu
                545                 550                 555                 560
                Met Thr Asn Glu Glu Glu Ile Arg Pro Thr Asn Pro Val Ala Thr Glu
                                565                 570                 575
                Glu Tyr Gly Ile Val Ser Ser Asn Leu Gln Ala Ala Asn Thr Ala Ala
                            580                 585                 590
                Gln Thr Gln Val Val Asn Asn Gln Gly Ala Leu Pro Gly Met Val Trp
                        595                 600                 605
                Gln Asn Arg Asp Val Tyr Leu Gln Gly Pro Ile Trp Ala Lys Ile Pro
                    610                 615                 620
                His Thr Asp Gly Asn Phe His Pro Ser Pro Leu Met Gly Gly Phe Gly
                625                 630                 635                 640
                Leu Lys His Pro Pro Pro Gln Ile Leu Ile Lys Asn Thr Pro Val Pro
                                645                 650                 655
                Ala Asn Pro Pro Glu Val Phe Thr Pro Ala Lys Phe Ala Ser Phe Ile
                            660                 665                 670
                Thr Gln Tyr Ser Thr Gly Gln Val Ser Val Glu Ile Glu Trp Glu Leu
                        675                 680                 685
                Gln Lys Glu Asn Ser Lys Arg Trp Asn Pro Glu Ile Gln Tyr Thr Ser
                    690                 695                 700
                Asn Phe Glu Lys Gln Thr Gly Val Asp Phe Ala Val Asp Ser Gln Gly
                705                 710                 715                 720
                Val Tyr Ser Glu Pro Arg Pro Ile Gly Thr Arg Tyr Leu Thr Arg Asn
                                725                 730                 735
                Leu

<210> SEQ ID NO 31
<211> LENGTH: 738
<212> TYPE: PRT
```

```
<213> ORGANISM: Unknown
<220> FEATURE:
<223> OTHER INFORMATION: capsid protein of adeno-associated virus
      serotype 8

<400> SEQUENCE: 31
```

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

```
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 32
<211> LENGTH: 735
<212> TYPE: PRT
<213> ORGANISM: Unknown
<220> FEATURE:
<223> OTHER INFORMATION: capsid protein of adeno-associated virus, hu.13

<400> SEQUENCE: 32

Met Ala Ala Asp Gly Tyr Leu Pro Asp Trp Leu Glu Asp Thr Leu Ser
```

-continued

```
1               5                   10                  15
Glu Gly Ile Arg Gln Trp Trp Lys Leu Lys Pro Gly Pro Pro Pro
                20                  25                  30
Lys Pro Ala Glu Arg His Lys Asp Asp Ser Arg Gly Leu Val Leu Pro
                35                  40                  45
Gly Tyr Lys Tyr Leu Gly Pro Phe Asn Gly Leu Asp Lys Gly Glu Pro
 50                  55                  60
Val Asn Glu Ala Asp Ala Ala Leu Glu His Asp Lys Ala Tyr Asp
 65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Glu Pro Val Lys Thr Ala Pro Gly Lys Lys Arg
                130                 135                 140
Pro Val Glu His Ser Pro Ala Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
                180                 185                 190
Ala Ala Pro Ser Gly Leu Gly Thr Asn Thr Met Ala Ser Gly Ser Gly
                195                 200                 205
Ala Pro Met Ala Asp Asn Asn Glu Gly Ala Asp Gly Val Gly Asn Ser
                210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
                290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
                370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
```

```
Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Gly Gly Asn Thr Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 33
<211> LENGTH: 735
<212> TYPE: PRT
<213> ORGANISM: Unknown
<220> FEATURE:
<223> OTHER INFORMATION: capsid protein of adeno-associated virus, hu.26

<400> SEQUENCE: 33

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60
```

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Ala Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Ser Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Met Ser Arg Leu Gln Phe Ser Gln
450                 455                 460

Ala Gly Ala Ser Asp Ile Arg Asp Gln Ser Arg Asn Trp Leu Pro Gly
465                 470                 475                 480
```

Pro Cys Tyr Arg Gln Gln Arg Val Ser Lys Thr Ala Ala Asp Asn Asn
                485                 490                 495

Asn Ser Asp Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Tyr Phe Pro Gln Ser Gly Val Leu Ile Phe Gly Lys
            530                 535                 540

Gln Asp Ser Gly Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Ser Gly Asn Thr Gln Ala Ala Thr
            580                 585                 590

Ser Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 34
<211> LENGTH: 738
<212> TYPE: PRT
<213> ORGANISM: Unknown
<220> FEATURE:
<223> OTHER INFORMATION: capsid protein of adeno-associated virus, hu.37

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

-continued

```
Asn Leu Gly Arg Ala Val Phe Gln Ala Lys Lys Arg Val Leu Glu Pro
            115                 120                 125

Leu Gly Leu Val Glu Glu Ala Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
```

```
                530             535             540
Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
                580                 585                 590

Pro Ile Val Gly Asn Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 35
<211> LENGTH: 734
<212> TYPE: PRT
<213> ORGANISM: Unknown
<220> FEATURE:
<223> OTHER INFORMATION: capsid protein of adeno-associated virus, hu.53

<400> SEQUENCE: 35

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
                50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Pro Val Lys Thr Ala Pro Gly Lys Lys Arg
                130                 135                 140

Pro Val Glu His Ser Pro Ala Glu Pro Asp Ser Ser Ser Gly Thr Gly
145                 150                 155                 160
```

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Arg Gln Pro Pro
            180                 185                 190

Ala Ala Pro Thr Ser Leu Gly Ser Thr Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Thr Ala Ser Gly Thr Gln Gln Ser Arg Leu Leu Phe Ser Gln Ala
    450                 455                 460

Gly Pro Thr Ser Met Ser Leu Gln Ala Lys Asn Trp Leu Pro Gly Pro
465                 470                 475                 480

Cys Tyr Arg Gln Gln Arg Leu Ser Lys Gln Ala Asn Asp Asn Asn Asn
                485                 490                 495

Ser Asn Phe Pro Trp Thr Gly Ala Thr Lys Tyr Tyr Leu Asn Gly Arg
            500                 505                 510

Asp Ser Leu Val Asn Pro Gly Pro Ala Met Ala Ser His Lys Asp Asp
        515                 520                 525

Glu Glu Lys Phe Phe Pro Met His Gly Thr Leu Ile Phe Gly Lys Glu
    530                 535                 540

Gly Thr Asn Ala Thr Asn Ala Glu Leu Glu Asn Val Met Ile Thr Asp
545                 550                 555                 560

Glu Glu Glu Ile Arg Thr Thr Asn Pro Val Ala Thr Glu Gln Tyr Gly
                565                 570                 575

```
Tyr Val Ser Asn Asn Leu Gln Asn Ser Asn Thr Ala Ala Ser Thr Glu
            580                 585                 590

Thr Val Asn His Gln Gly Ala Leu Pro Gly Met Val Trp Gln Asp Arg
            595                 600                 605

Asp Val Tyr Leu Gln Gly Pro Ile Trp Ala Lys Ile Pro His Thr Asp
            610                 615                 620

Gly His Phe His Pro Ser Pro Leu Met Gly Gly Phe Gly Leu Lys His
625                 630                 635                 640

Pro Pro Pro Gln Ile Met Ile Lys Asn Thr Pro Val Pro Ala Asn Pro
                    645                 650                 655

Pro Thr Asn Phe Ser Ser Ala Lys Phe Ala Ser Phe Ile Thr Gln Tyr
            660                 665                 670

Ser Thr Gly Gln Val Ser Val Glu Ile Glu Trp Glu Leu Gln Lys Glu
            675                 680                 685

Asn Ser Lys Arg Trp Asn Pro Glu Ile Gln Tyr Thr Ser Asn Tyr Asn
            690                 695                 700

Lys Ser Val Asn Val Asp Phe Thr Val Asp Thr Asn Gly Val Tyr Ser
705                 710                 715                 720

Glu Pro Arg Pro Ile Gly Thr Arg Tyr Leu Thr Arg Asn Leu
                    725                 730

<210> SEQ ID NO 36
<211> LENGTH: 738
<212> TYPE: PRT
<213> ORGANISM: Unknown
<220> FEATURE:
<223> OTHER INFORMATION: capsid protein of rhesus adeno-associated
      virus, rh.39

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205
```

-continued

```
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
            245                 250                 255
Leu Tyr Lys Gln Ile Ser Asn Gly Thr Ser Gly Ser Thr Asn Asp
        260                 265                 270
Asn Thr Tyr Phe Gly Tyr Ser Thr Pro Trp Gly Tyr Phe Asp Phe Asn
            275                 280                 285
Arg Phe His Cys His Phe Ser Pro Arg Asp Trp Gln Arg Leu Ile Asn
        290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
            325                 330                 335
Asn Asn Leu Thr Ser Thr Ile Gln Val Phe Thr Asp Ser Glu Tyr Gln
        340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
            405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Gln Gly Thr Gln Gln Leu Leu
    450                 455                 460
Phe Ser Gln Ala Gly Pro Ala Asn Met Ser Ala Gln Ala Lys Asn Trp
465                 470                 475                 480
Leu Pro Gly Pro Cys Tyr Arg Gln Gln Arg Val Ser Thr Thr Leu Ser
            485                 490                 495
Gln Asn Asn Asn Ser Asn Phe Ala Trp Thr Gly Ala Thr Lys Tyr His
        500                 505                 510
Leu Asn Gly Arg Asp Ser Leu Val Asn Pro Gly Val Ala Met Ala Thr
        515                 520                 525
His Lys Asp Asp Glu Glu Arg Phe Phe Pro Ser Ser Gly Val Leu Met
    530                 535                 540
Phe Gly Lys Gln Gly Ala Gly Arg Asp Asn Val Asp Tyr Ser Ser Val
545                 550                 555                 560
Met Leu Thr Ser Glu Glu Ile Lys Thr Thr Asn Pro Val Ala Thr
            565                 570                 575
Glu Gln Tyr Gly Val Val Ala Asp Asn Leu Gln Gln Thr Asn Thr Gly
        580                 585                 590
Pro Ile Val Gly Asn Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
```

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
        645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 37
<211> LENGTH: 736
<212> TYPE: PRT
<213> ORGANISM: Unknown
<220> FEATURE:
<223> OTHER INFORMATION: capsid protein of rhesus adeno-associated
      virus, 43

<400> SEQUENCE: 37

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Glu Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Asn Thr Met Ala Ala Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Thr Trp Leu Gly Asp Arg Val Ile
225                 230                 235                 240

```
Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ala Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Arg Thr Gln Thr Thr Gly Gly Thr Ala Asn Thr Gln Thr Leu Gly Phe
        450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
            515                 520                 525

Lys Asp Asp Glu Glu Arg Phe Phe Pro Val Thr Gly Ser Cys Phe Trp
        530                 535                 540

Gln Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
            595                 600                 605

Asn Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
```

```
                        660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Tyr Lys Ser Thr Ser Val Asp Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 38
<211> LENGTH: 737
<212> TYPE: PRT
<213> ORGANISM: Unknown
<220> FEATURE:
<223> OTHER INFORMATION: capsid protein of adeno-associated virus, hu.48

<400> SEQUENCE: 38

Arg Met Ala Ala Asp Gly Tyr Leu Pro Asp Trp Leu Glu Asp Asn Leu
1               5                   10                  15
Ser Glu Gly Ile Arg Glu Trp Trp Asp Leu Lys Pro Gly Ala Pro Lys
            20                  25                  30
Pro Lys Ala Asn Gln Gln Lys Gln Asp Asp Gly Arg Gly Leu Val Leu
        35                  40                  45
Pro Gly Tyr Lys Tyr Leu Gly Pro Phe Asn Gly Leu Asp Lys Gly Glu
    50                  55                  60
Pro Val Asn Ala Ala Asp Ala Ala Ala Leu Glu His Asp Lys Ala Tyr
65                  70                  75                  80
Asp Gln Gln Leu Lys Ala Gly Asp Asn Pro Tyr Leu Arg Tyr Asn His
                85                  90                  95
Ala Asp Ala Glu Phe Gln Glu Arg Leu Gln Glu Asp Thr Ser Phe Gly
            100                 105                 110
Gly Asn Leu Gly Arg Ala Val Phe Gln Ala Lys Lys Arg Val Leu Glu
        115                 120                 125
Pro Leu Gly Leu Val Glu Glu Gly Ala Lys Thr Ala Pro Gly Lys Lys
    130                 135                 140
Arg Pro Val Glu Gln Ser Pro Gln Glu Pro Asp Ser Ser Ser Gly Ile
145                 150                 155                 160
Gly Lys Thr Gly Gln Gln Pro Ala Lys Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Thr Pro Ala Ala Val Gly Pro Thr Thr Met Ala Ser Gly Gly
        195                 200                 205
Gly Ala Pro Met Ala Asp Asn Asn Glu Gly Ala Asp Gly Val Gly Asn
    210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Thr Ser Thr Gly Ala Ser Asn Asp Asn
            260                 265                 270
His Tyr Phe Gly Tyr Gly Thr Pro Trp Gly Tyr Phe Asp Phe Asn Arg
        275                 280                 285
Phe His Cys His Phe Ser Pro Arg Asp Trp Gln Arg Leu Ile Asn Asn
```

```
             290                 295                 300
Asn Trp Gly Phe Arg Pro Lys Arg Leu Asn Phe Lys Leu Phe Asn Ile
305                 310                 315                 320
Gln Val Glu Glu Val Thr Thr Asn Asp Gly Val Thr Thr Ile Ala Asn
                    325                 330                 335
Asn Leu Thr Ser Thr Val Gln Val Phe Ser Asp Ser Glu Tyr Gln Leu
                340                 345                 350
Pro Tyr Val Leu Gly Ser Ala His Gln Gly Cys Leu Pro Pro Phe Pro
            355                 360                 365
Ala Asp Val Phe Met Ile Pro Gln Tyr Gly Tyr Leu Thr Leu Asn Asn
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Thr Phe Ser Tyr Thr
                    405                 410                 415
Phe Glu Glu Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Asn
            435                 440                 445
Arg Thr Gln Asn Gln Ser Gly Ser Ala Gln Asn Lys Asp Leu Leu Phe
        450                 455                 460
Ser Arg Gly Ser Pro Ala Gly Met Ser Val Gln Pro Lys Asn Trp Leu
465                 470                 475                 480
Pro Gly Pro Cys Tyr Arg Gln Gln Arg Val Ser Lys Thr Lys Thr Asp
                    485                 490                 495
Asn Asn Asn Ser Asn Phe Thr Trp Thr Gly Ala Ser Lys Tyr Asn Leu
                500                 505                 510
Asn Gly Arg Glu Ser Ile Ile Asn Pro Gly Thr Ala Val Ala Ser His
            515                 520                 525
Lys Asp Asp Glu Asp Lys Phe Phe Pro Met Ser Gly Val Met Ile Phe
        530                 535                 540
Gly Lys Glu Ser Ala Gly Ala Ser Ser Thr Ala Leu Asp Asn Val Met
545                 550                 555                 560
Ile Thr Asp Glu Glu Glu Ile Lys Ala Thr Asn Pro Val Ala Thr Glu
                    565                 570                 575
Arg Phe Gly Thr Val Ala Val Asn Phe Gln Ser Ser Ser Thr Asp Pro
                580                 585                 590
Ala Thr Gly Asp Val His Ala Met Gly Ala Leu Pro Gly Met Val Trp
            595                 600                 605
Gln Asp Arg Asp Val Tyr Leu Gln Gly Pro Ile Trp Ala Lys Ile Pro
        610                 615                 620
His Thr Asp Gly His Phe His Pro Ser Pro Leu Met Gly Gly Phe Gly
625                 630                 635                 640
Leu Lys Asn Pro Pro Pro Gln Ile Leu Ile Lys Asn Thr Pro Val Pro
                    645                 650                 655
Ala Asn Pro Pro Ala Glu Phe Ser Ala Thr Lys Phe Ala Ser Phe Ile
                660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Val Gln Tyr Thr Ser
        690                 695                 700
Asn Tyr Ala Lys Ser Ala Asn Val Asp Phe Thr Val Asp Asn Asn Gly
705                 710                 715                 720
```

```
Leu Tyr Thr Glu Pro Arg Pro Ile Gly Thr Arg Tyr Leu Thr Arg Pro
                725                 730                 735

Leu

<210> SEQ ID NO 39
<211> LENGTH: 738
<212> TYPE: PRT
<213> ORGANISM: Unknown
<220> FEATURE:
<223> OTHER INFORMATION: capsid protein of rhesus adeno-associated
      virus, 2

<400> SEQUENCE: 39

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335
```

```
Asn Asn Leu Thr Ser Thr Ile Gln Val Phe Thr Asp Ser Glu Tyr Gln
            340                 345                 350

Leu Pro Tyr Val Pro Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
            450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 40
<211> LENGTH: 729
<212> TYPE: PRT
<213> ORGANISM: Unknown
<220> FEATURE:
<223> OTHER INFORMATION: capsid protein of rhesus adeno-associated virus, 37

<400> SEQUENCE: 40

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Gly Ala Pro Thr Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Trp Gly Phe Arg
    290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365
```

-continued

```
Ile Pro Gln Tyr Gly Tyr Leu Thr Leu Asn Asn Gly Ser Gln Ser Val
370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
            405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Thr
            435                 440                 445

Thr Gly Ser Thr Arg Glu Leu Gln Phe His Gln Ala Gly Pro Asn Thr
450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
            485                 490                 495

Trp Thr Ala Ala Thr Lys Tyr His Leu Asn Gly Arg Asn Ser Leu Thr
            500                 505                 510

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
530                 535                 540

Lys Thr Thr Leu Glu Asn Val Leu Met Thr Ser Glu Glu Glu Ile Lys
545                 550                 555                 560

Thr Thr Asn Pro Val Ala Thr Glu Glu Tyr Gly Val Val Ser Ser Asn
            565                 570                 575

Leu Gln Ser Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
610                 615                 620

Ser Pro Leu Met Gly Gly Phe Gly Leu Glu His Pro Pro Gln Ile
625                 630                 635                 640

Leu Ile Lys Asn Thr Pro Val Pro Ala Asn Pro Glu Val Phe Thr
            645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Ala Lys Ser Asn Asn Val
690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
            725
```

<210> SEQ ID NO 41
<211> LENGTH: 736
<212> TYPE: PRT
<213> ORGANISM: Unknown
<220> FEATURE:
<223> OTHER INFORMATION: capsid protein of rhesus adeno-associated virus, 8

<400> SEQUENCE: 41

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Ser Gly Leu Gly Pro Asn Thr Met Ala Ser Gly Gly Gly
                195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Val Pro Gln Tyr Gly Tyr Leu Thr Leu Asn Asn
        370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415
```

```
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Val
            435                 440                 445
Arg Thr Gln Thr Thr Gly Thr Gly Thr Gln Thr Leu Ala Phe Ser
450                 455                 460
Gln Ala Gly Pro Ser Ser Met Ala Asn Gln Ala Arg Asn Trp Val Pro
465                 470                 475                 480
Gly Pro Cys Tyr Arg Gln Gln Arg Val Ser Thr Thr Thr Asn Gln Asn
                485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
        515                 520                 525
Asp Asp Asp Asp Arg Phe Phe Pro Ser Ser Gly Val Leu Ile Phe Gly
            530                 535                 540
Lys Gln Gly Ala Gly Asn Asp Gly Val Asp Tyr Ser Gln Val Leu Ile
545                 550                 555                 560
Thr Asp Glu Glu Glu Ile Lys Ala Thr Asn Pro Val Ala Thr Glu Glu
                565                 570                 575
Tyr Gly Ala Val Ala Ile Asn Asn Gln Ala Ala Asn Thr Gln Ala Gln
            580                 585                 590
Thr Gly Leu Val His Asn Gln Gly Val Ile Pro Gly Met Val Trp Gln
        595                 600                 605
Asn Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asp Pro Pro Leu Thr Phe Asn Gln Ala Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
690                 695                 700
Tyr Tyr Lys Ser Thr Asn Val Asp Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 42
<211> LENGTH: 735
<212> TYPE: PRT
<213> ORGANISM: Unknown
<220> FEATURE:
<223> OTHER INFORMATION: capsid protein of adeno-associated virus, hu.
      29

<400> SEQUENCE: 42

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
```

-continued

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Pro Val Lys Thr Ala Pro Gly Lys Lys Arg
            130                 135                 140

Pro Val Glu His Ser Pro Ala Glu Pro Asp Ser Ser Gly Thr Gly
145                 150                 155                 160

Lys Ser Gly Asn Gln Pro Ala Arg Lys Arg Leu Asn Phe Gly Gln Thr
                165                 170                 175

Gly Asp Ser Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Gly Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

```
Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Pro Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Ser Gly Asn Thr Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 43
<211> LENGTH: 738
<212> TYPE: PRT
<213> ORGANISM: Unknown
<220> FEATURE:
<223> OTHER INFORMATION: capsid protein of rhesus adeno-associated
      virus, 64

<400> SEQUENCE: 43

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Ser Val Gly Ser Gly Thr Met Ala Ala Gly Gly
            195                 200                 205

Gly Ala Pro Met Ala Asp Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Ser Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
            450                 455                 460

Phe Ser Gln Ala Gly Pro Ser Asn Met Ser Ala Gln Ala Arg Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510
```

```
Leu Asn Gly Arg Asp Ser Leu Val Asn Pro Gly Val Ala Met Ala Thr
            515                 520                 525

Asn Lys Asp Asp Glu Asp Arg Phe Phe Pro Ser Ser Gly Ile Leu Met
    530                 535                 540

Phe Gly Lys Gln Gly Ala Gly Lys Asp Asn Val Asp Tyr Ser Asn Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Thr Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Ala Phe Asn Gln Ala Lys Leu Asn Ser Phe
                660                 665                 670

Ile Thr Gln Tyr Ser Thr Gly Gln Val Ser Val Glu Ile Val Trp Glu
            675                 680                 685

Leu Gln Lys Glu Asn Ser Lys Arg Arg Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 44
<211> LENGTH: 737
<212> TYPE: PRT
<213> ORGANISM: Unknown
<220> FEATURE:
<223> OTHER INFORMATION: capsid protein of rhesus adeno-associated
      virus, 48

<400> SEQUENCE: 44

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Ala Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
                195                 200                 205
Gly Ala Pro Met Ala Asp Asn Asn Lys Gly Ala Asp Gly Val Gly Asn
    210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Gln Ser Ala Gly Ser Thr Asn Asp Asn
                260                 265                 270
Val Tyr Phe Gly Tyr Ser Thr Pro Trp Gly Tyr Phe Asp Phe Asn Arg
    275                 280                 285
Phe His Cys His Phe Ser Pro Arg Asp Trp Gln Arg Leu Ile Asn Ser
    290                 295                 300
Asn Trp Gly Phe Arg Pro Lys Lys Leu Asn Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Val Gln Val Phe Ser Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Ile Pro Gln Tyr Gly Tyr Leu Thr Leu Asn Asn
    370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Thr Phe Ser Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ala
            435                 440                 445
Arg Thr Gln Ser Asn Ala Gly Gly Thr Ala Gly Asn Arg Glu Leu Gln
    450                 455                 460
Phe Tyr Gln Gly Gly Pro Thr Thr Met Ala Glu Gln Ala Lys Asn Trp
465                 470                 475                 480
Leu Pro Gly Pro Cys Phe Arg Gln Gln Arg Val Ser Lys Thr Leu Asp
                485                 490                 495
Gln Asn Asn Asn Ser Asn Phe Ala Trp Thr Gly Ala Thr Lys Tyr His
            500                 505                 510
Leu Asn Gly Arg Asn Ser Leu Val Asn Pro Gly Val Ala Met Ala Thr
        515                 520                 525
His Lys Asp Asp Glu Glu Arg Phe Phe Pro Ser Ser Gly Val Leu Ile
    530                 535                 540
Phe Gly Lys Thr Gly Ala Ala Asn Lys Thr Thr Leu Glu Asn Val Leu
```

```
                545                 550                 555                 560
Met Thr Asn Glu Glu Ile Arg Pro Thr Asn Pro Val Ala Thr Glu
                    565                 570                 575
Glu Tyr Gly Thr Val Ser Ser Asn Leu Gln Ala Ala Asn Thr Ala Ala
                580                 585                 590
Gln Thr Gln Val Val Asn Asn Gln Gly Ala Leu Pro Gly Met Val Trp
                595                 600                 605
Gln Asn Arg Asp Val Tyr Leu Gln Gly Pro Ile Trp Ala Lys Ile Pro
                610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                    645                 650                 655
Ala Asn Pro Pro Glu Val Phe Thr Pro Ala Lys Phe Ala Ser Phe Ile
                660                 665                 670
Thr Gln Tyr Ser Thr Gly Gln Val Ser Val Glu Ile Glu Trp Glu Leu
                675                 680                 685
Gln Lys Glu Asn Ser Lys Arg Trp Asn Pro Glu Ile Gln Tyr Thr Ser
                690                 695                 700
Asn Phe Asp Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                    725                 730                 735
Leu

<210> SEQ ID NO 45
<211> LENGTH: 736
<212> TYPE: PRT
<213> ORGANISM: Unknown
<220> FEATURE:
<223> OTHER INFORMATION: capsid protein of adeno-associated virus, hu.44

<400> SEQUENCE: 45

Met Ala Ala Asp Gly Tyr Leu Pro Asp Trp Leu Glu Asp Thr Leu Ser
1               5                   10                  15
Glu Gly Ile Arg Gln Trp Trp Lys Leu Arg Pro Gly Pro Pro Pro
                20                  25                  30
Lys Pro Ala Glu Arg His Lys Asp Asp Ser Arg Gly Leu Val Leu Pro
                35                  40                  45
Gly Tyr Lys Tyr Leu Gly Pro Phe Asn Gly Leu Asp Lys Gly Glu Pro
            50                  55                  60
Val Asn Glu Ala Asp Ala Ala Leu Glu His Asp Lys Ala Tyr Asp
65              70                  75                  80
Arg Gln Leu Asp Ser Gly Asp Asn Pro Tyr Leu Lys Tyr Asn His Ala
                    85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Glu Thr Ala Pro Gly Lys Lys Arg
        130                 135                 140
Pro Val Glu Gln Ser Pro Gln Gly Pro Asp Ser Ser Ser Gly Ile Gly
145                 150                 155                 160
Lys Thr Gly Gln Gln Pro Ala Lys Lys Arg Leu Asn Phe Gly Gln Thr
                    165                 170                 175
```

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Pro Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
            580                 585                 590
```

```
Thr Gly Asp Val His Ala Met Gly Ala Leu Pro Gly Met Val Trp Gln
            595                 600                 605

Gly Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 46
<211> LENGTH: 735
<212> TYPE: PRT
<213> ORGANISM: Unknown
<220> FEATURE:
<223> OTHER INFORMATION: capsid protein of adeno-associated virus
      chimpanzee 5

<400> SEQUENCE: 46

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220
```

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Glu Ser Gly Ala Thr Asn Asp Asn His Tyr
        260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
        290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Ile Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
            435                 440                 445

Gln Gly Thr Ser Gly Thr Thr Gln Gln Ser Arg Leu Gln Phe Ser Gln
450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
            485                 490                 495

Asn Ser Glu Phe Ala Trp Thr Ala Ala Thr Lys Tyr Tyr Leu Asn Gly
            500                 505                 510

Arg Asn Ser Leu Val Asn Pro Gly Pro Pro Met Ala Ser His Lys Asp
            515                 520                 525

Asp Glu Glu Lys Tyr Phe Pro Met His Gly Asn Leu Ile Phe Gly Lys
            530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
            565                 570                 575

Gly Gln Val Ala Thr Asn His Gln Ser Gln Asn Thr Thr Ala Ser Tyr
            580                 585                 590

Gly Ser Val Asp Ser Gln Gly Ile Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640
```

-continued

```
His Pro Pro Pro Gln Ile Leu Ile Lys Asn Thr Pro Val Pro Ala Asn
            645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
            725                 730                 735
```

<210> SEQ ID NO 47
<211> LENGTH: 737
<212> TYPE: PRT
<213> ORGANISM: Unknown
<220> FEATURE:
<223> OTHER INFORMATION: capsid protein of rhesus adeno-associated
      virus, 67

<400> SEQUENCE: 47

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Leu Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Ala Gly Ser Thr Asn Asp Asn
            260                 265                 270
```

```
Val Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
    435                 440                 445

Arg Thr Gln Ser Asn Ala Gly Gly Thr Ala Gly Asn Arg Glu Leu Gln
    450                 455                 460

Phe Tyr Gln Gly Gly Pro Thr Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
                500                 505                 510

Leu Asn Gly Arg Asn Ser Leu Val Asn Pro Gly Val Ala Met Ala Thr
            515                 520                 525

His Lys Asp Asp Glu Glu Arg Phe Phe Pro Ser Ser Gly Val Leu Ile
    530                 535                 540

Phe Gly Lys Thr Gly Ala Ala Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Thr Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685
```

-continued

```
Gln Lys Glu Asn Ser Lys Arg Trp Asn Pro Glu Ile Gln Tyr Thr Ser
    690             695                 700
Asn Phe Asp Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                725                 730                 735
Leu
```

<210> SEQ ID NO 48
<211> LENGTH: 738
<212> TYPE: PRT
<213> ORGANISM: Unknown
<220> FEATURE:
<223> OTHER INFORMATION: capsid protein of rhesus adeno-associated
      virus, 58

<400> SEQUENCE: 48

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Ala Ala Lys Thr Ala Pro Gly Lys Lys Arg
130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Ala Pro Ser Ser Val Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
```

```
Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Ser Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Ser Asn Met Ser Ala Gln Ala Arg Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

Asn Lys Asp Asp Glu Asp Arg Phe Phe Pro Ser Ser Gly Ile Leu Met
530                 535                 540

Phe Gly Lys Gln Gly Ala Gly Lys Asp Asn Val Asp Tyr Ser Asn Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Thr Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Ser Thr Pro Val
                645                 650                 655

Pro Ala Asp Pro Pro Thr Ala Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Cys Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
```

Asn Leu

<210> SEQ ID NO 49
<211> LENGTH: 737
<212> TYPE: PRT
<213> ORGANISM: Unknown
<220> FEATURE:
<223> OTHER INFORMATION: capsid protein of rhesus adeno-associated virus, 54

<400> SEQUENCE: 49

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Ala Gly Ser Thr Asn Asp Asn
            260                 265                 270

Val Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
```

```
            340                 345                 350
Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ser Val Gly Arg Ser Ser Phe Cys Leu Glu Tyr Phe
385                 390                 395                 400

Pro Ser Gln Val Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ala
                435                 440                 445

Arg Thr Gln Ser Asn Pro Gly Gly Thr Ser Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
                500                 505                 510

Leu Asn Gly Arg Asn Ser Leu Val Asn Pro Gly Val Ala Met Ala Thr
                515                 520                 525

His Lys Asp Asp Glu Asp Arg Phe Phe Pro Ser Ser Gly Val Leu Ile
                530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Phe Asp Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

METHOD OF INCREASING THE FUNCTION OF AN AAV VECTOR

CROSS-REFERENCE TO RELATED APPLICATIONS

This application is a continuation of U.S. patent application Ser. No. 15/408,567, filed Jan. 18, 2017, which is a continuation of U.S. patent application Ser. No. 14/624,671, filed Feb. 18, 2015, which is a division of U.S. patent application Ser. No. 11/887,679, filed Oct. 2, 2007, now U.S. Pat. No. 8,999,678, issued Apr. 7, 2015, which is a national stage of PCT/US2006/013375, filed Apr. 7, 2006, which claims the benefit of U.S. patent application Ser. No. 60/669,083, filed Apr. 7, 2005, and U.S. patent application Ser. No. 60/733,497, filed Nov. 4, 2005, which are hereby incorporated by reference.

GOVERNMENT SUPPORT

This invention was made with government support under grant/contract number P01 HL 059407 awarded by the National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "R3895C2US_Seq_List_ST25.txt".

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, *Dependovirus*, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

AAV vectors have been described for use as delivery vehicles for both therapeutic and immunogenic molecules. To date, there have been several different well-characterized AAVs isolated from human or non-human primates (NHP).

Recently, investigators have described a large number of AAVs of different sequences [G. Gao, et al., *Proc Natl Acad Sci USA*, 100(10):6081-6086 (May 13, 2003); US-2003-0138772-A1 (Jul. 24, 2003)] and characterized these AAVs into different serotypes and clades [G. Gao, et al., *J. Vivol.*, 78(12):6381-6388 (June 2004); International Patent Publication No. WO 2005/033321]. It has been reported that different AAVs exhibit different transfection efficiencies, and also exhibit tropism for different cells or tissues.

What is desirable are AAV-based constructs for delivery of heterologous molecules to different cell types.

SUMMARY OF THE INVENTION

The present invention provides a method of improving vectors derived from AAV which are non-functional and/or which perform weakly.

In one aspect, the method provides a method for correcting singletons in a selected AAV sequence in order to increase the packaging yield, transduction efficiency, and/or gene transfer efficiency of the selected AAV. This method involves altering one or more singletons in the parental AAV capsid to conform the singleton to the amino acid in the corresponding position(s) of the aligned functional AAV capsid sequences.

In another aspect, the invention provides modified AAV sequences, i.e., sequences with one or more singletons eliminated.

In yet another aspect, the invention provides AAV vectors having modified AAV capsids according to the present invention.

Other aspects and advantages of the invention will be readily apparent from the following detailed description of the invention.

BRIEF DESCRIPTION OF THE DRAWINGS

FIG. 1 is a graph illustrating in vitro 293 transduction of singleton corrected AAV vectors. Singleton corrections are indicated after the vector name with—if present—a number to indicate the number of mutations performed.

Figure 4A:
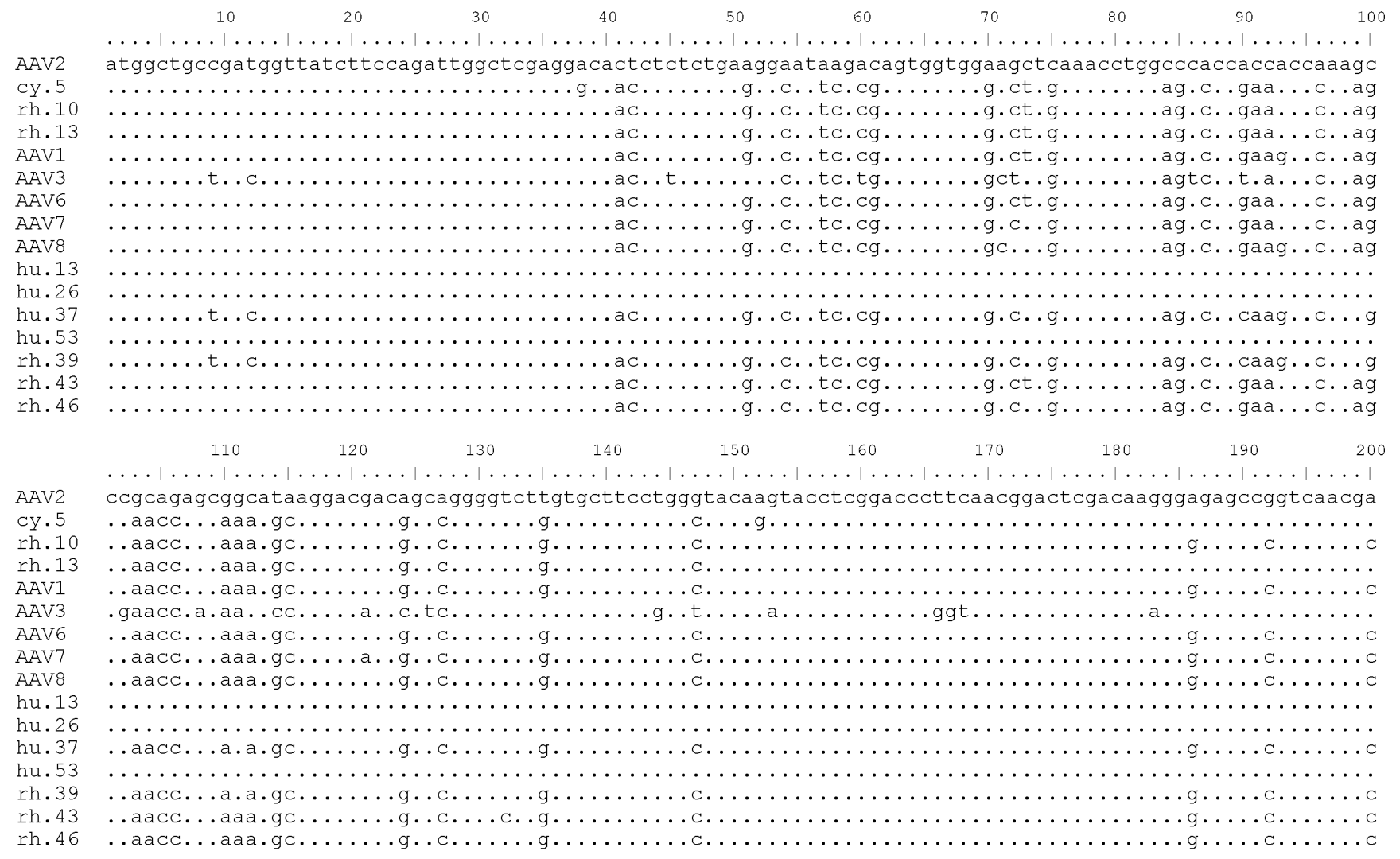
Figure 4B:
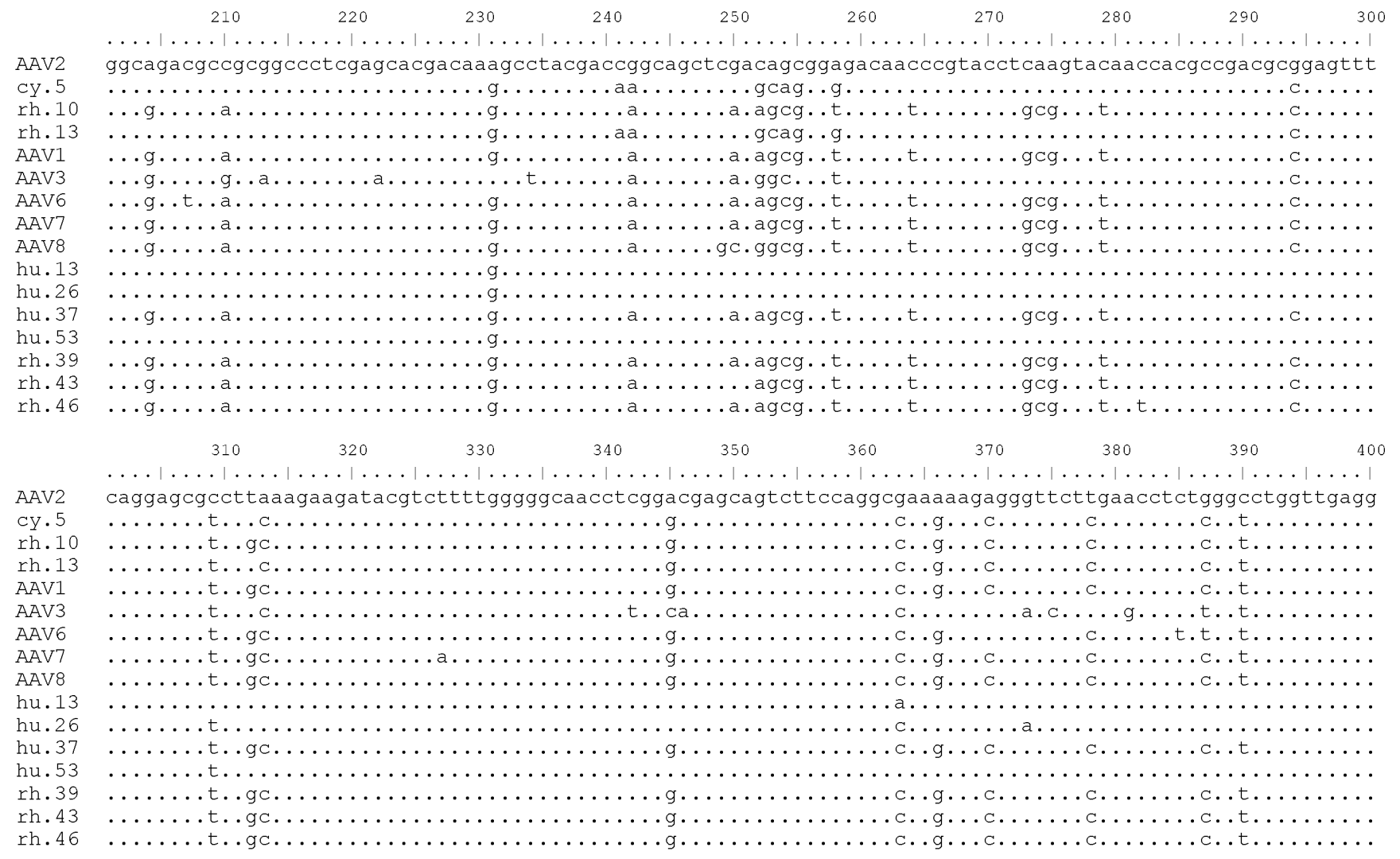
Figure 4C:
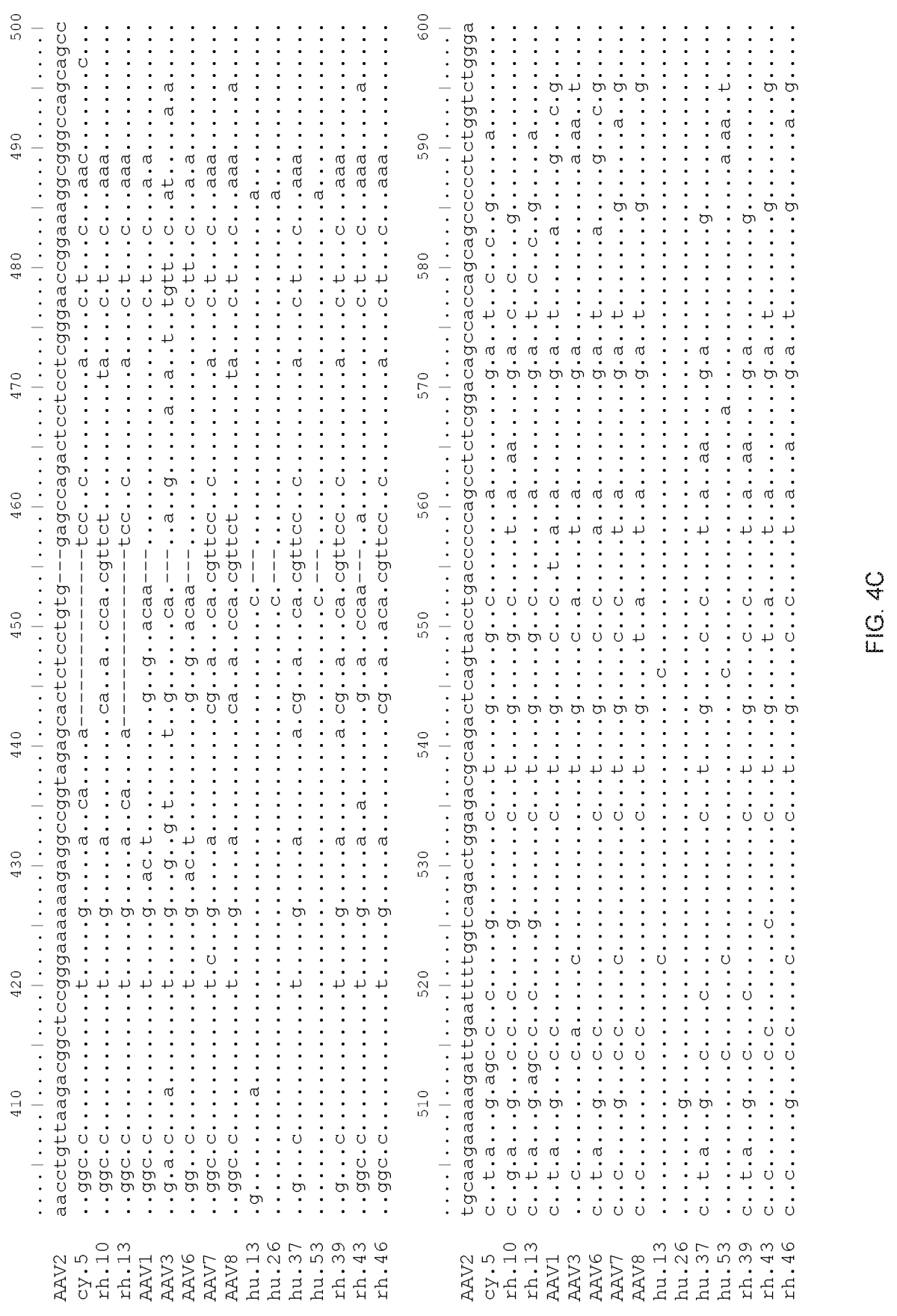
Figure 4D:
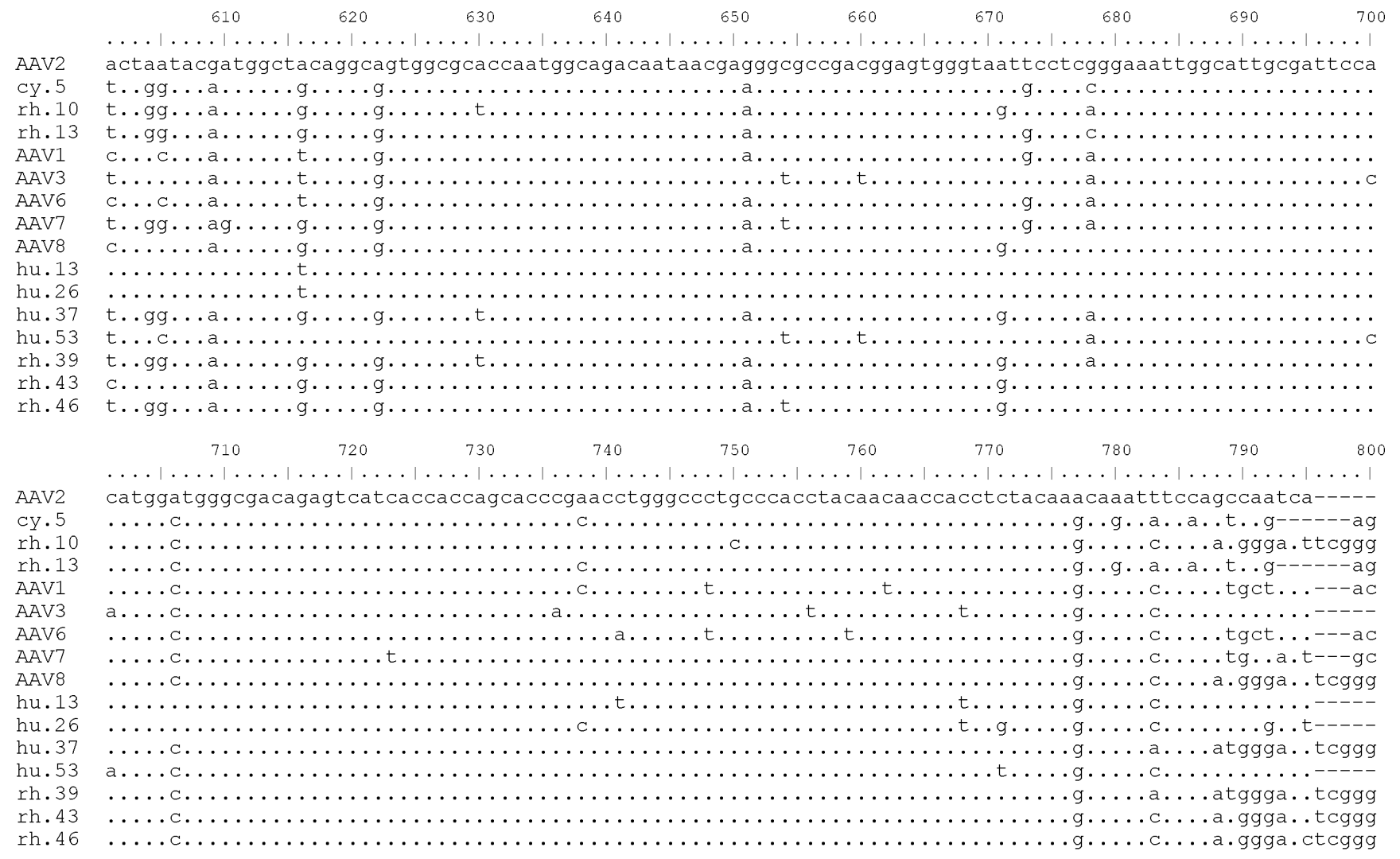
Figure 4E:
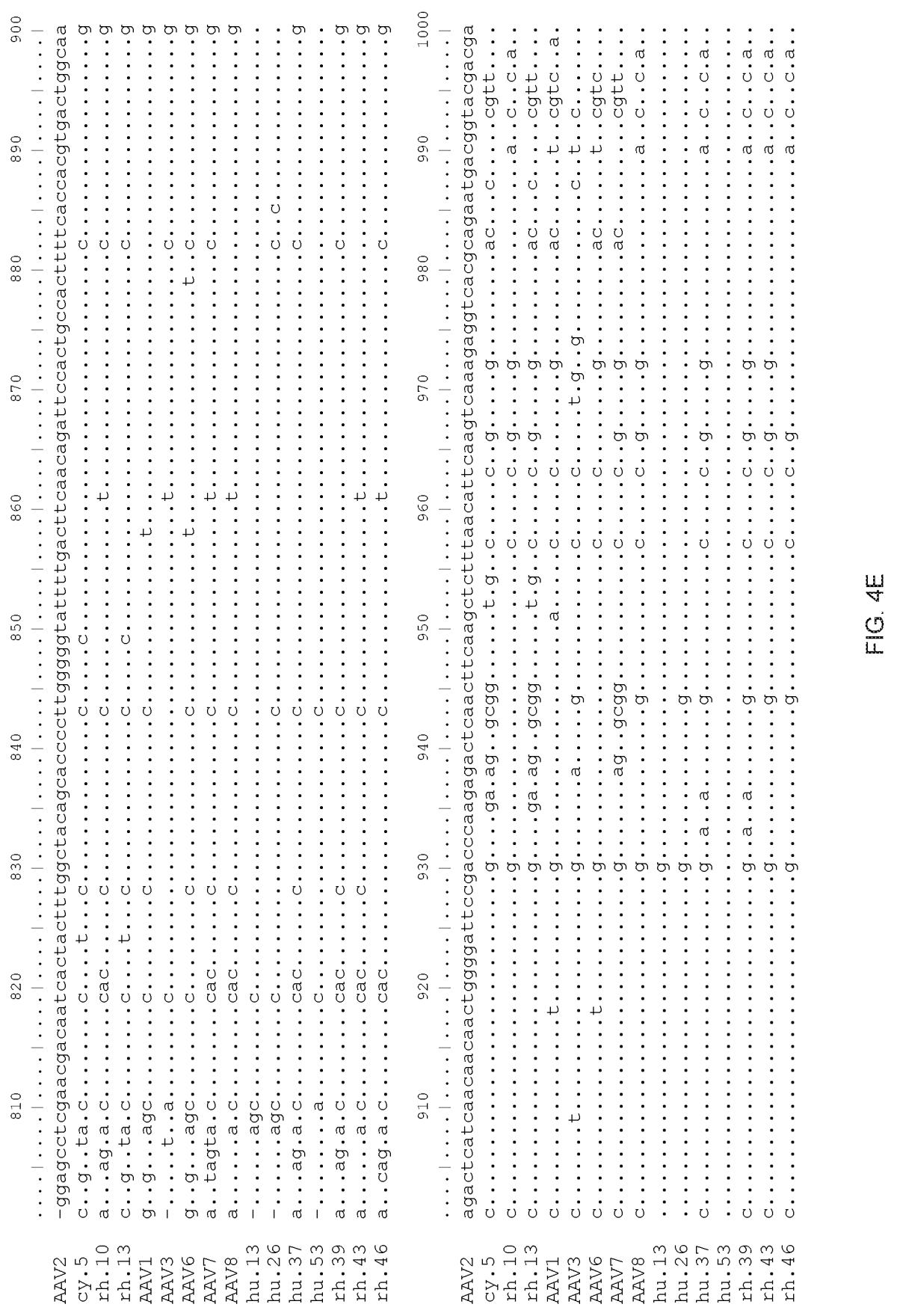
Figure 4F:
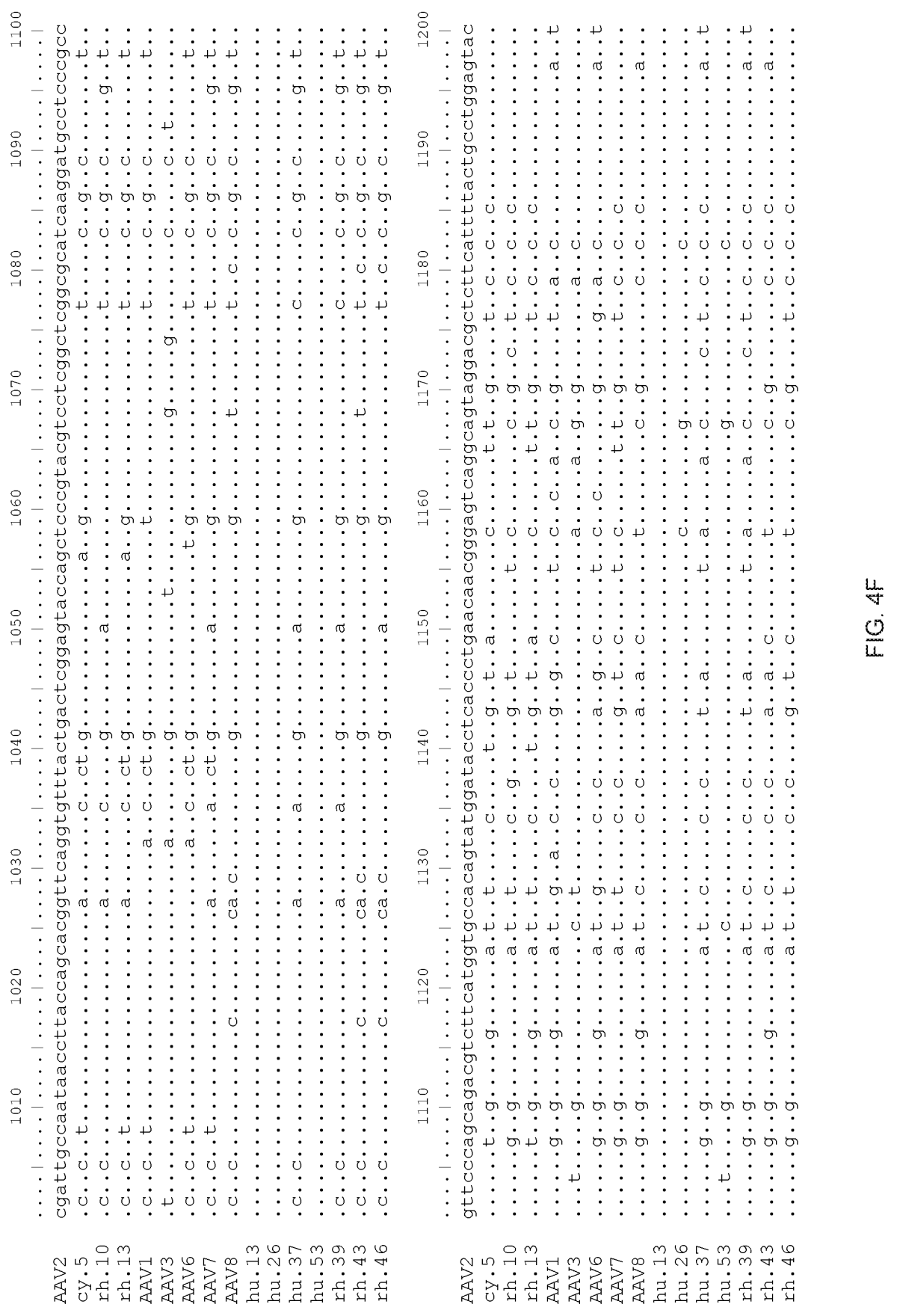
Figure 4G:
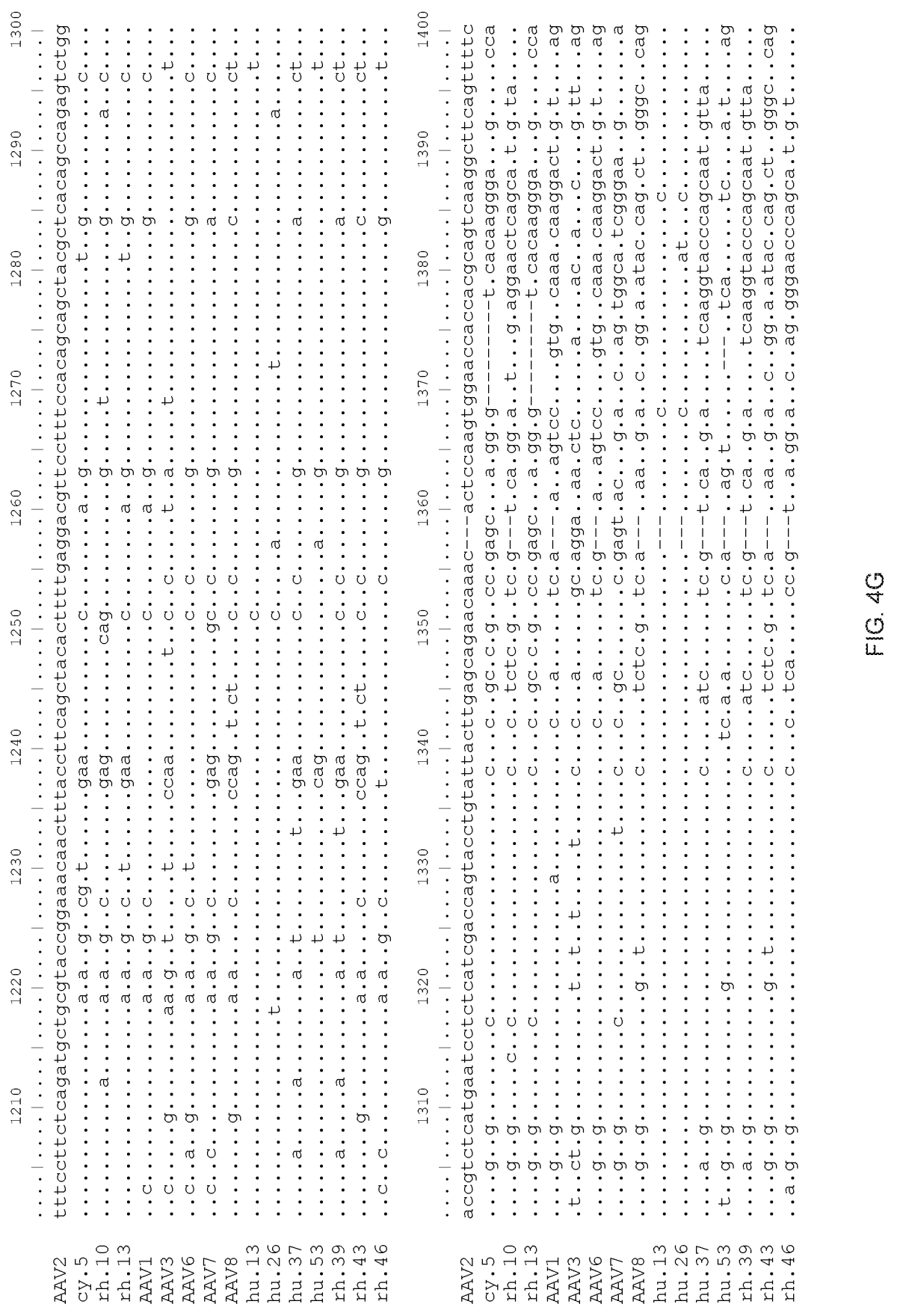
Figure 4H:
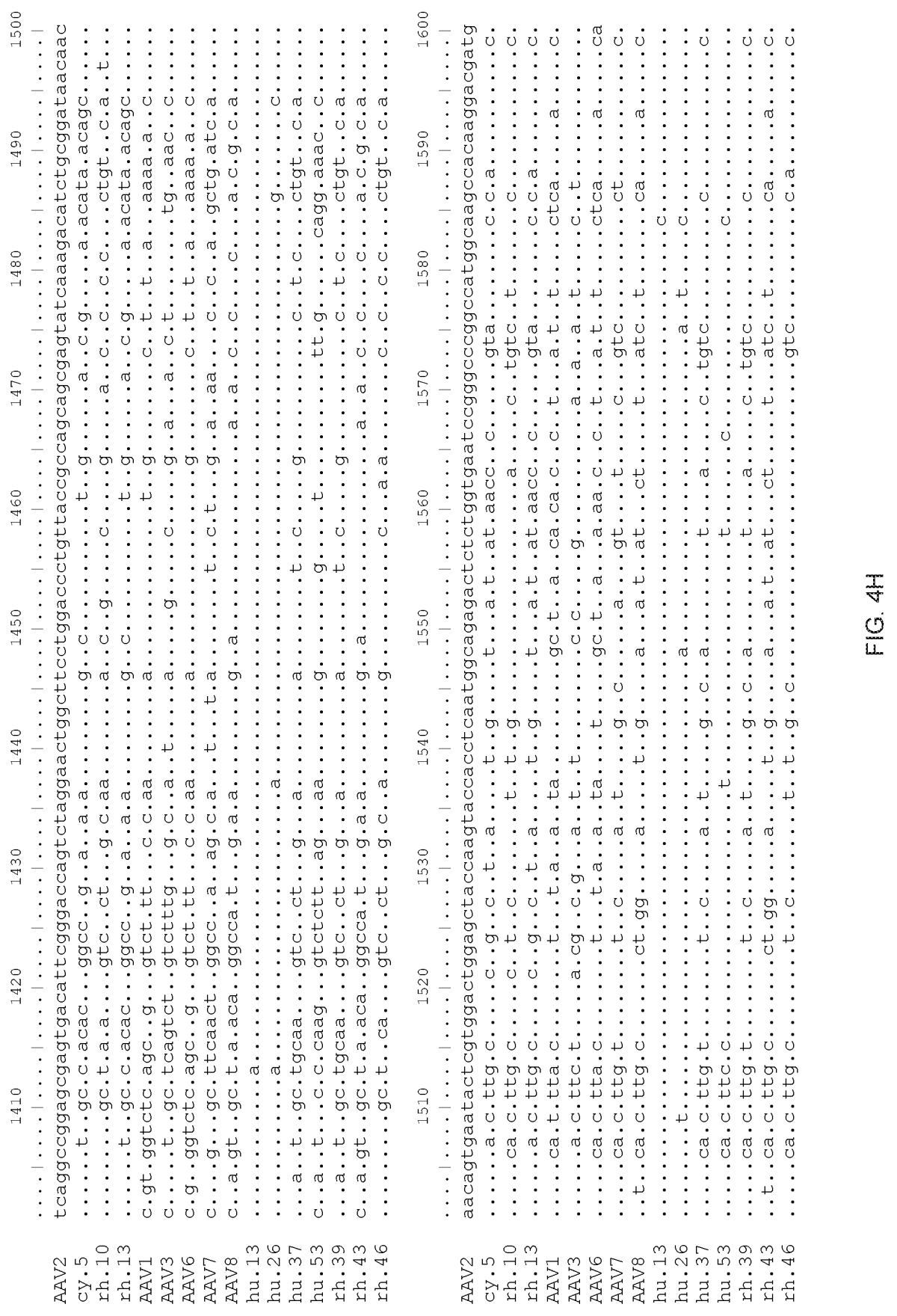
Figure 4I:
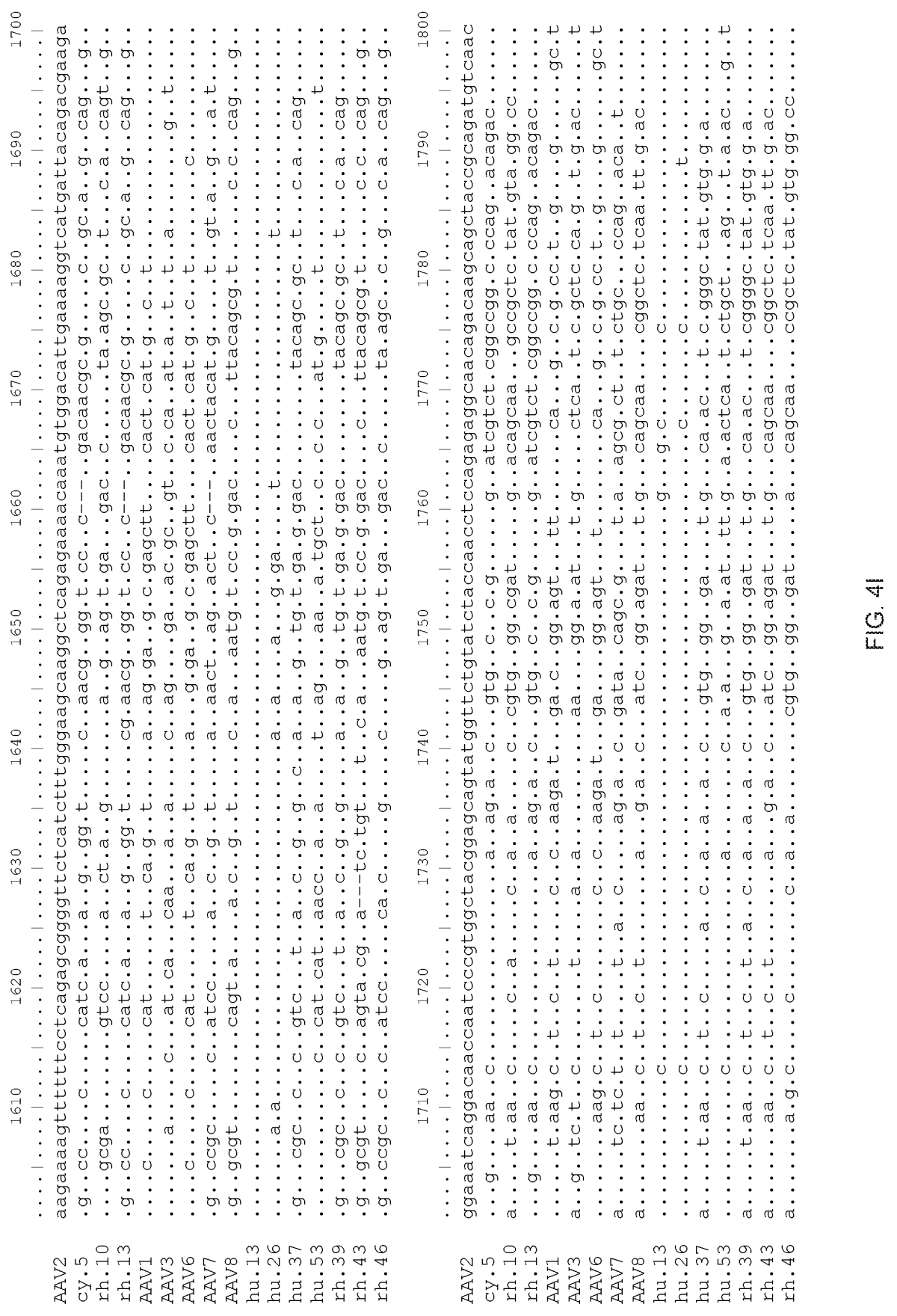
Figure 4J:
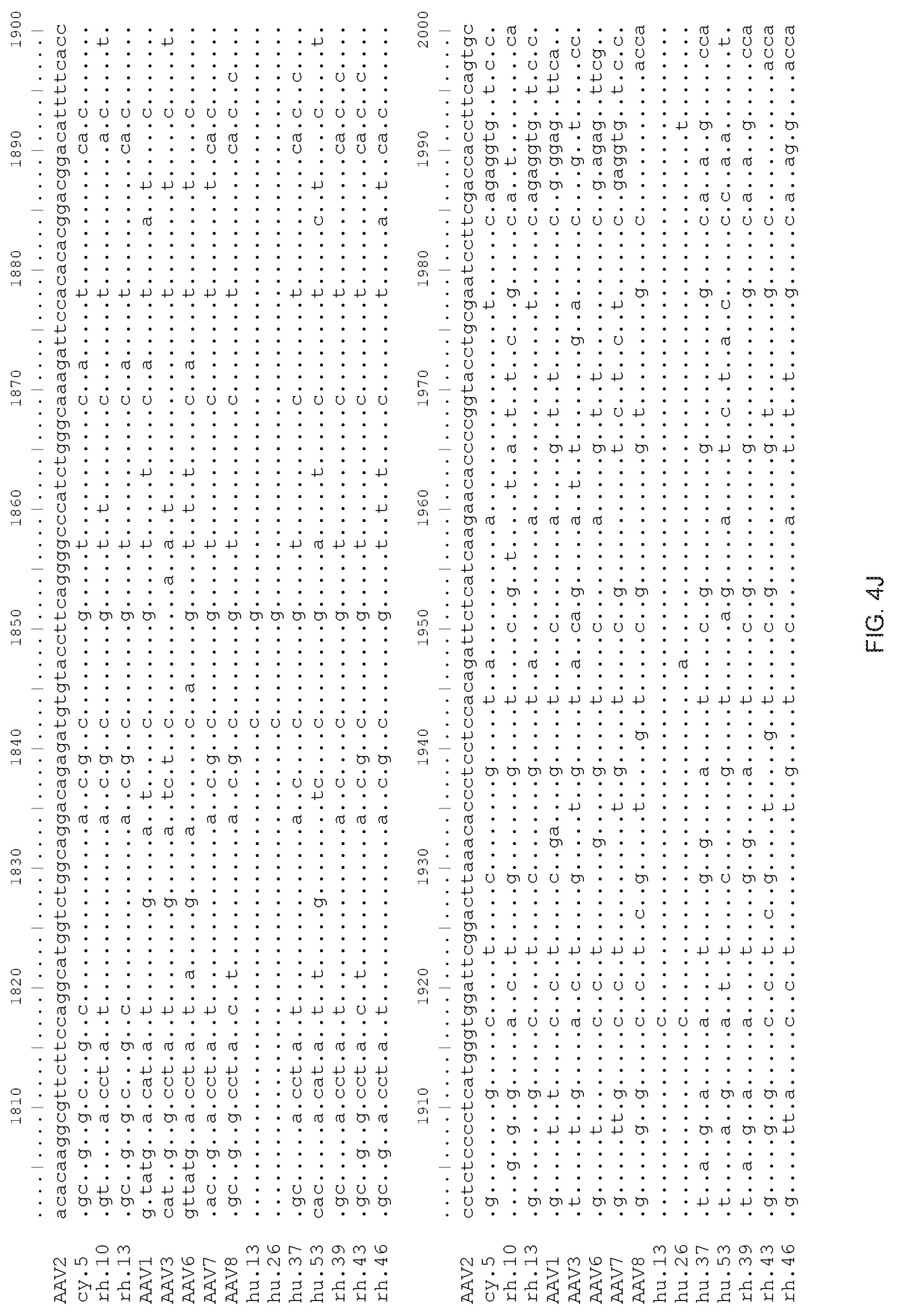
Figure 4K:
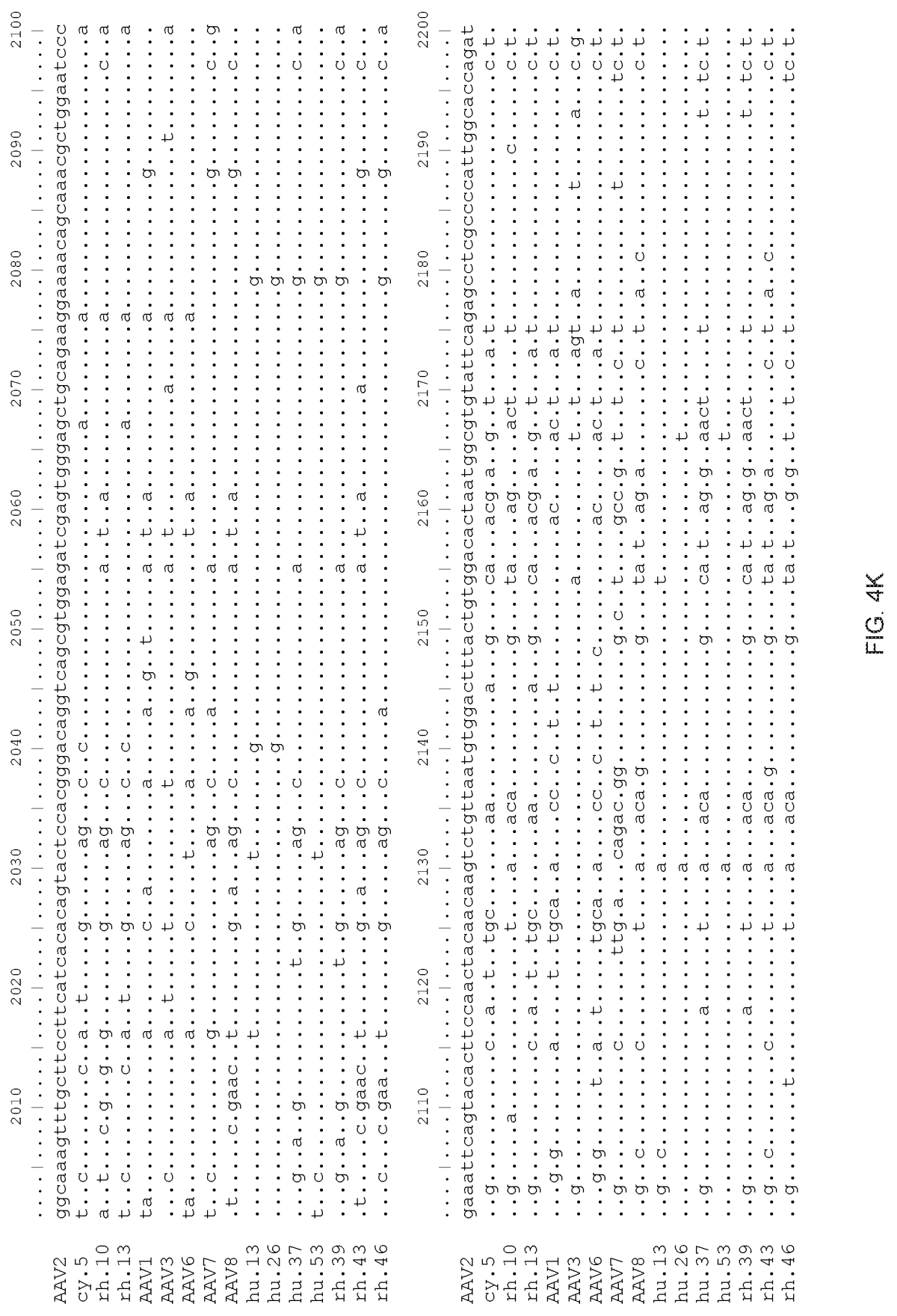

FIGS. 4A-4L are an alignment of the nucleic acid sequences of the capsid protein (vp1) of AAV2 [SEQ ID NO:7], cy.5 [SEQ ID NO:8], rh.10 [SEQ ID NO: 9], rh.13 [SEQ ID NO: 10], AAV1 [SEQ ID NO: 11], AAV3 [SEQ ID NO: 12], AAV6 [SEQ ID NO: 13], AAV7 [SEQ ID NO: 14], AAV8 [SEQ ID NO: 15], hu.13 [SEQ ID NO:16], hu.26 [SEQ ID NO: 17], hu.37 [SEQ ID NO: 18], hu.53 [SEQ ID NO: 19], rh.39 [SEQ ID NO: 20], rh.43 [SEQ ID NO: 21] and rh.46 [SEQ ID NO: 22].

Figure 5A:
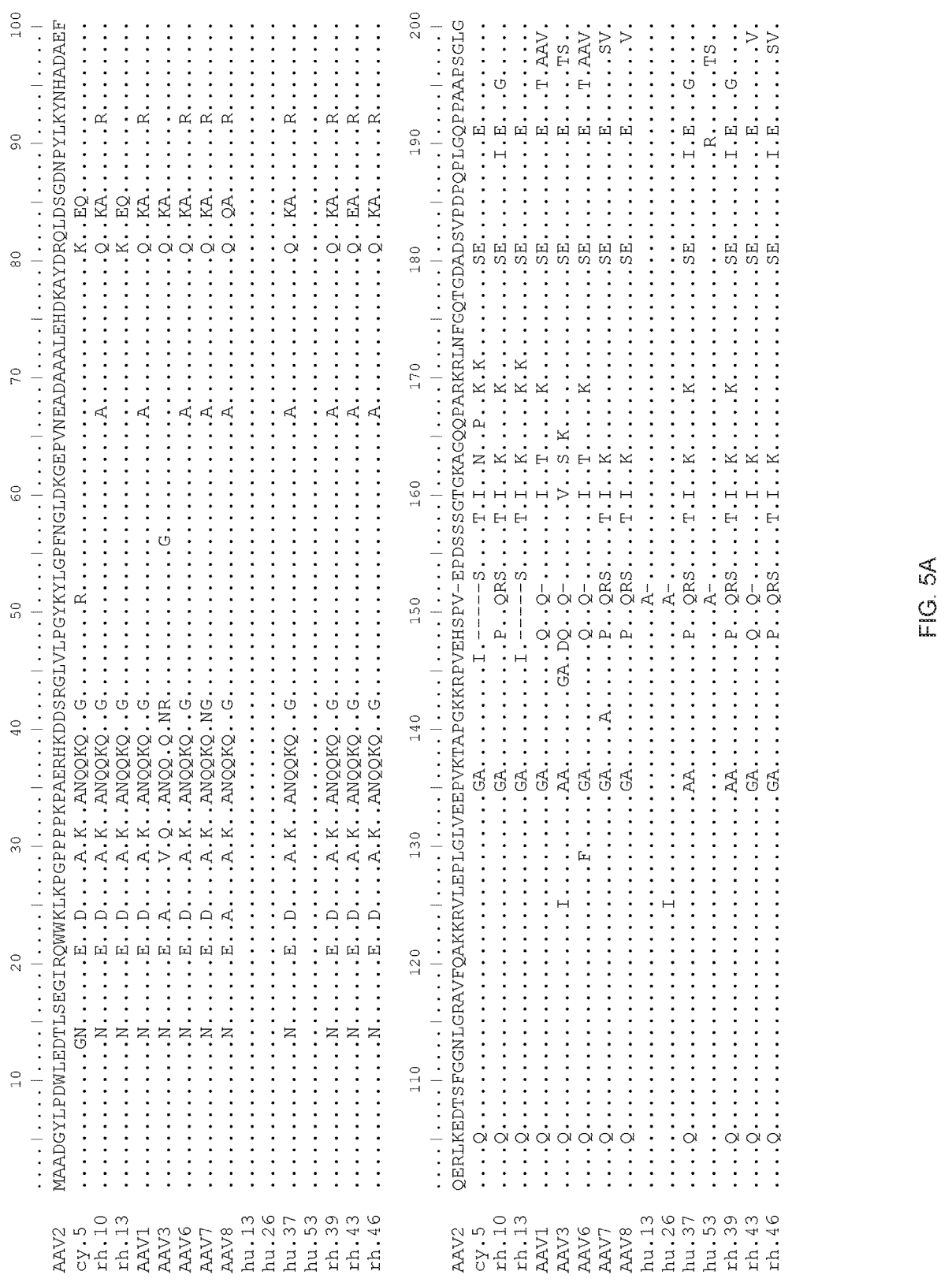
Figure 5C:
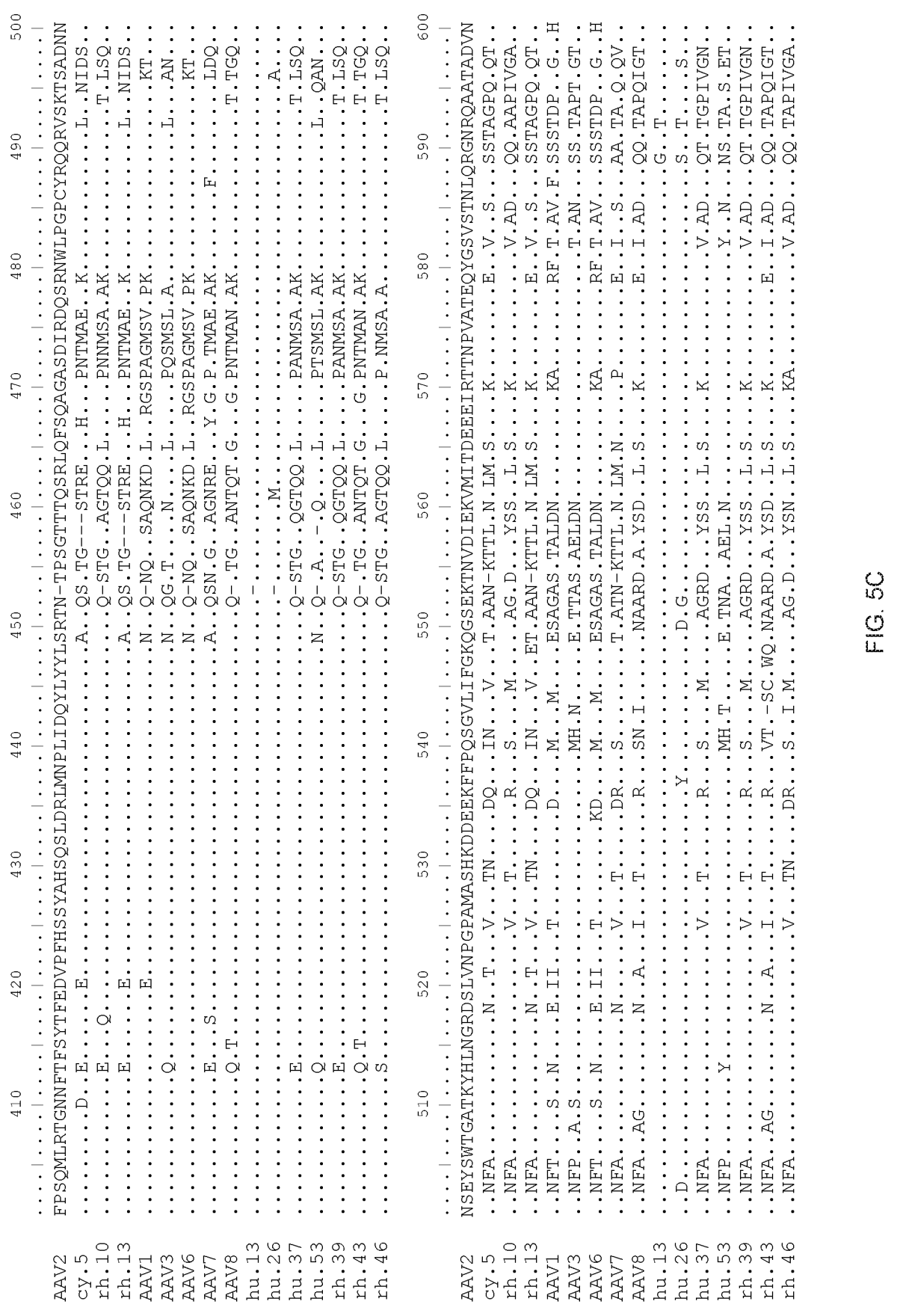

FIGS. 5A-5D are an alignment of the amino acid sequences of the capsid protein (vp1) of AAV2 [SEQ ID NO: 23], cy.5 [SEQ ID NO: 24], rh.10 [SEQ ID NO: 25], rh.13 [SEQ ID NO: 26], AAV1 [SEQ ID NO: 27], AAV3 [SEQ ID NO: 28], AAV6 [SEQ ID NO: 29], AAV7 [SEQ ID NO: 30], AAV8 [SEQ ID NO: 31], hu.13 [SEQ ID NO: 32], hu.26 [SEQ ID NO: 33], hu.37 [SEQ ID NO: 34], hu.53 [SEQ ID NO: 35], rh.39 [SEQ ID NO: 36], rh.43 [SEQ ID NO: 37] and rh.46 [SEQ ID NO: 38].

FIGS. 6A-6B are an alignment of the amino acid sequences of the capsid protein (vp1) of rh.13 [SEQ ID NO: 26], rh2 [SEQ ID NO: 39], rh.8 [SEQ ID NO: 41], hu.29 [SEQ ID NO: 42], and rh.64 [SEQ ID NO: 43].

DETAILED DESCRIPTION OF THE INVENTION

Figure 2A:
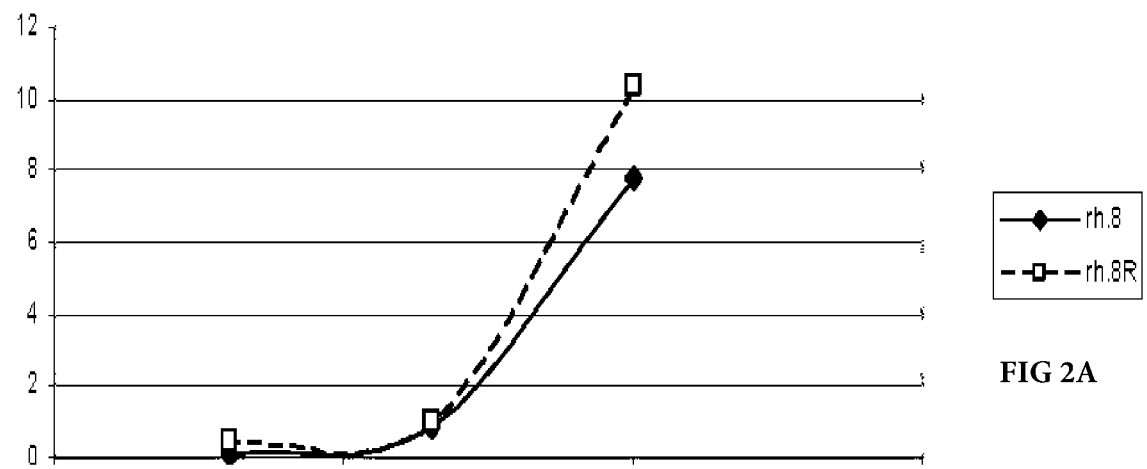
FIGS. 2A-2C are line graphs illustrating the titration of AAV vectors on 293 cells at multiplicities of infection ranging from $10^1$ to $10^4$, with a comparison between parent rh.8 and singleton-corrected rh.8 (rh.8R) in FIG. 2A, parent rh.37 and modified rh.37 (FIG. 2B), and AAV2 and AAV8 in FIG. 2C. As a control, a similar titration of AAV2 and AAV2/8 eGFP expressing vector is presented. Percent (%) of eGFP positive cells is presented on the Y-axis and was assayed by flow cytometry.
Figure 2B:
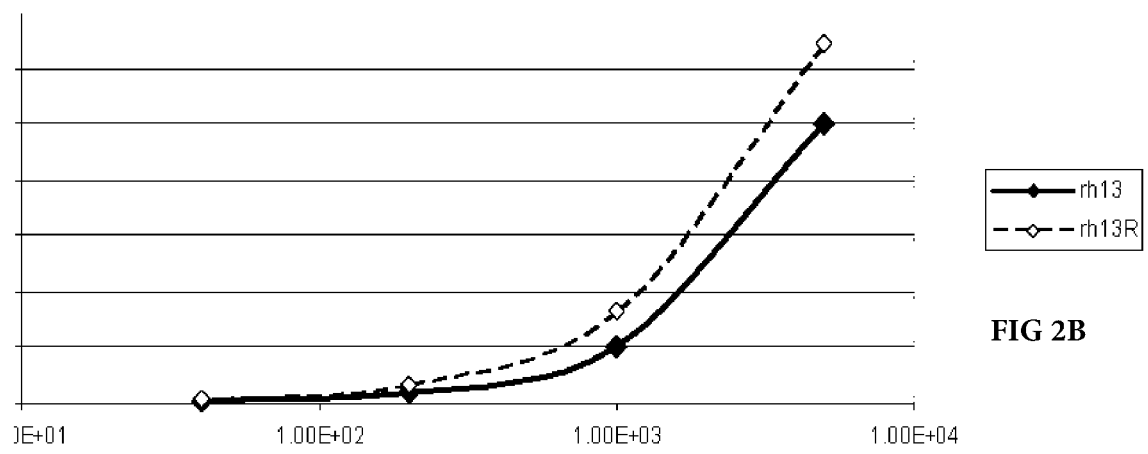
Figure 2C:
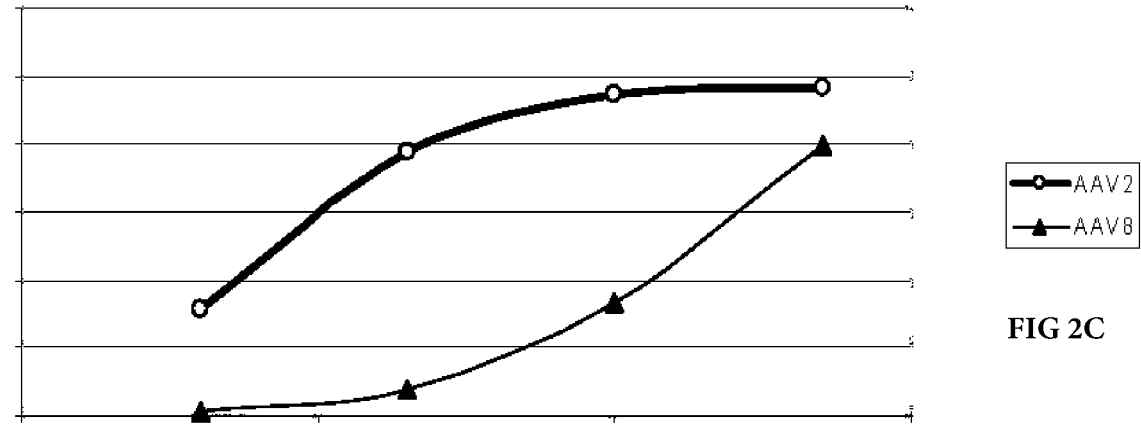
Figure 3:
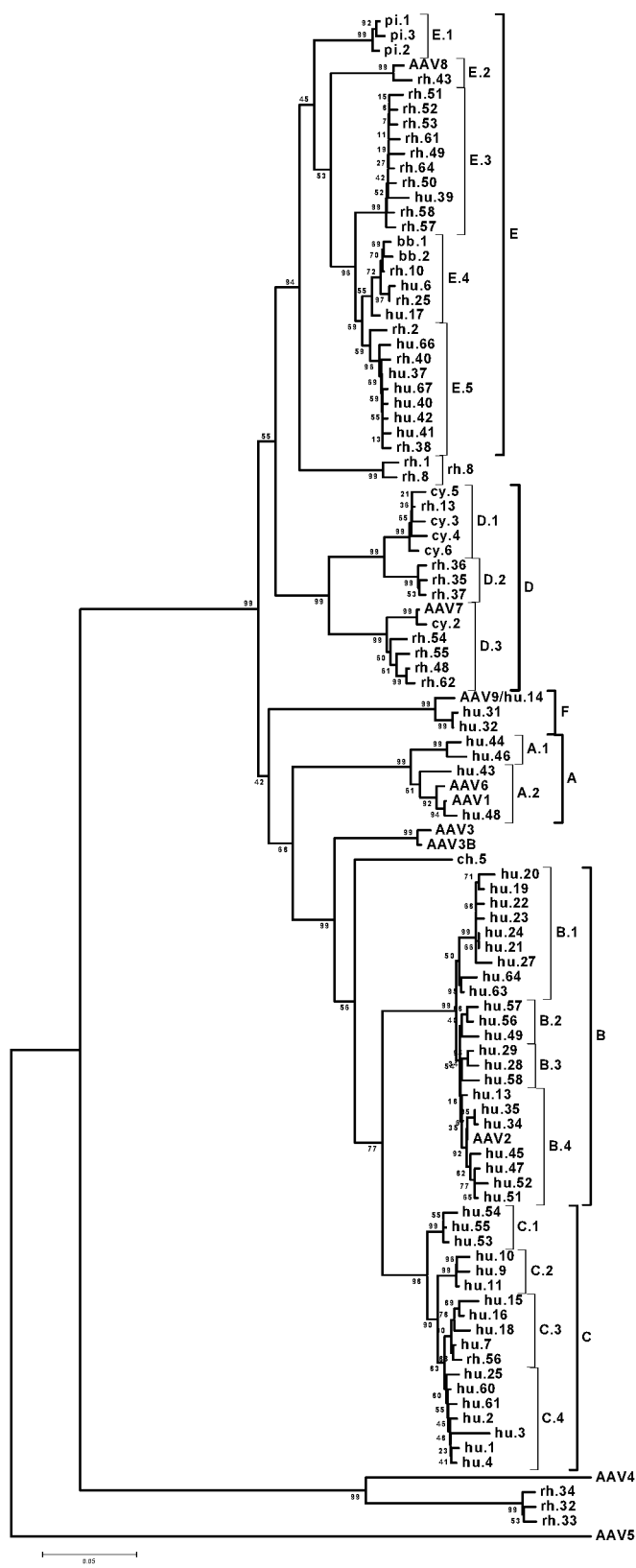
FIG. 3 is a phylogenetic tree of AAV sequences, which indicates their phylogenetic relationship and clades.
Figure 5B:
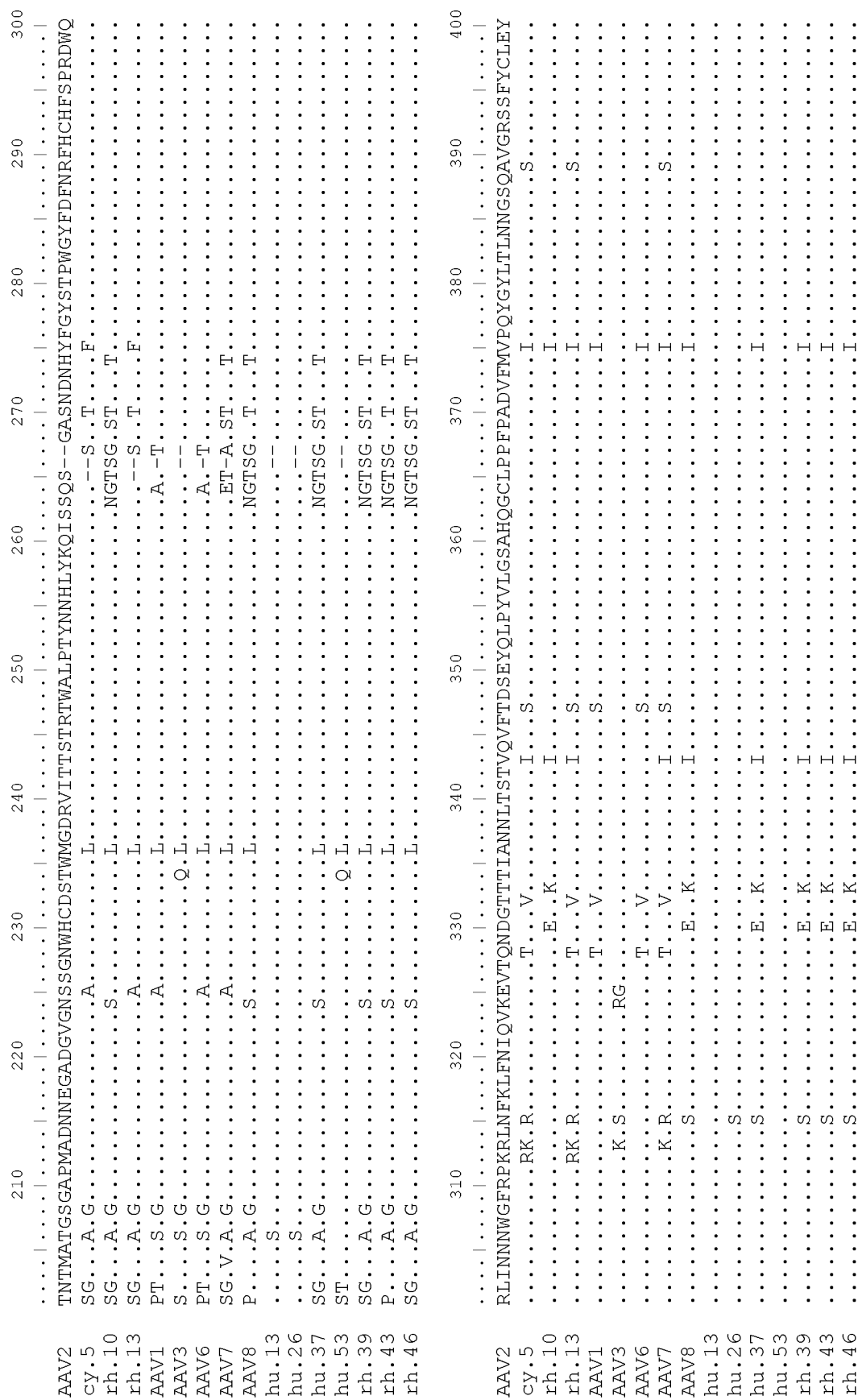

The present invention provides a method for improving the function of an AAV vector. The present invention is particularly well suited to improve the packaging yield, transduction efficiency, and/or gene transfer efficiency of an AAV vector having a capsid of an AAV which contains one or more singletons. The invention further provides novel AAV capsid sequences identified and prepared according to the method of the invention.

As used throughout this specification and the claims, the terms "comprising" and "including" are inclusive of other components, elements, integers, steps and the like. Conversely, the term "consisting" and its variants are exclusive of other components, elements, integers, steps and the like.

SINGLETON METHOD OF INVENTION

As used herein, the term "singleton" refers to a variable amino acid in a given position in a selected (i.e., parental) AAV capsid sequence. The presence of a variable amino acid is determined by aligning the sequence of the parental AAV capsid with a library of functional AAV capsid sequences. The sequences are then analyzed to determine the presence of any variable amino acid sequences in the parental AAV capsid where the sequences of the AAV in the library of functional AAVs have complete conservation. The parental AAV sequence is then altered to change the singleton to the conserved amino acid identified in that position in the functional AAV capsid sequences. According to the present invention, a parental AAV sequence may have 1 to 6, 1 to 5, 1 to 4, 1 to 3, or 2 singletons. A parental AAV sequence may have more than 6 singletons.

Once modified, the modified AAV capsid can be used to construct an AAV vector having the modified capsid. This vector can be constructed using techniques known to those of skill in the art.

The AAV selected for modification according to the invention method is one for which it is desirable to increase any one or more of the following three functional properties of AAV, i.e., packaging into the viral particle having the capsid of the selected AAV sequence, increasing transduction efficiency, or increasing gene transfer efficiency as compared to the parental AAV. For example, the parental AAV may be characterized by having a lower packaging efficiency than other, closely related AAV. In another example, the parental AAV may have a lower transduction efficiency as compared to closely related AAVs. In another example, the parental AAV may have a lower gene transfer efficiency (i.e., a lower ability to deliver a target molecule in vivo) as compared to closely related AAVs. In other examples, the parental AAV is characterized by adequate function in each of these categories, but increased function one or more of these areas is desired.

Thus, the invention provides a library of functional AAVs, the sequences of which are to be compared to the selected (parental) AAV. Suitably, the library contains AAVs which have a desired function which is targeted for improvement in the selected parental AAV. In other words, each of the sequences in the library of functional AAVs is characterized by a desired level of packaging ability, a desired level of in vitro transduction efficiency, or a desired level of in vivo gene transfer efficiency (i.e., the ability to deliver to a target selected target tissue or cell in a subject). The functional AAVs which compose the library may individually have one, two or all of these functional characteristics. Other desired functions for the library may be readily determined by one of skill in the art.

In one embodiment, a functional AAV is an AAV characterized by the ability to produce viral particles with equivalent or greater packaging and transduction efficiency as any one of AAV1, AAV2, AAV7, AAV8 or AAV9. Function may be assessed in a pseudotyping setting with AAV2 rep and AAV2 ITRs. Thus, an altered parental AAV can be constructed using conventional techniques and the AAV vector is considered functional if virus is produced from the parental AAV at titers of at least 50% when compared to production of AAV2. Further, the ability of AAV to transduce cells can be readily determined by one of skill in the art. For example, a parental AAV can be constructed such that it contains a marker gene which allows ready detection of virus. For example, the AAV contains eGFP or another gene which allows fluorescent detection. Where the AAV contains CMV-eGFP, when the virus produced from the altered parental AAV capsid is transduced into 293 cells at a multiplicity of infection of $10^4$, function is demonstrated where transduction efficiency is greater than 5% GFP fluorescence of total cells in a context where the cells were pretreated with wild-type human adenovirus type 5 at a multiplicity of infection of 20 for 2 hours.

Suitably, a library is composed of at least three or at least four functional AAV capsid sequences which represent at least two different clades. Preferably, at least two sequences from each of the represented clades is included in the library. In certain embodiments, three, four, five, six, or more clades are represented.

A "clade" is a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence.

The Neighbor-Joining algorithm has been described extensively in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades.

While the AAV clades are based primarily upon naturally occurring AAV vp1 capsids, the clades are not limited to naturally occurring AAV. The clades can encompass non-naturally occurring AAV, including, without limitation, recombinant, modified or altered, chimeric, hybrid, synthetic, artificial, etc., AAV which are phylogenetically related as determined using a Neighbor-Joining algorithm at least 75% (of at least 1000 replicates) and a Poisson correction distance measurement of no more than 0.05, based on alignment of the AAV vp1 amino acid sequence.

The AAV clades which have been described include Clade A (represented by AAV1 and AAV6), Clade B (represented by AAV2) and Clade C (represented by the AAV2-AAV3 hybrid), Clade D (represented by AAV7), Clade E (represented by AAV8), and Clade F (represented by human AAV9). These clades are represented by a member of the clade that is a previously described AAV serotype. Previously described AAV1 and AAV6 are members of a single clade (Clade A) in which 4 isolates were recovered from 3 humans. Previously described AAV3 and AAV5 serotypes are clearly distinct from one another, but were not detected in the screen described herein, and have not been included in any of these clades.

Further discussion of AAV clades is provided in G. Gao, et al., J. Virol., 78(12):6381-6388 (June 2004) and International Patent Publication Nos. WO 2004/028817 and WO2005/033321. The latter document also provides novel human AAV sequences, which are incorporated by reference herein.

In one embodiment, the libraries used in the method of the invention exclude AAV5. In another embodiment, the libraries used in the method of the invention exclude AAV4. However, in certain embodiments, e.g., where the parental AAV is similar to AAV5, it may be desirable to include this sequence in the alignment.

Although a library can be constructed that contains the minimal number of sequences, efficiency in identifying singletons may be optimized by utilizing a library containing a larger number of sequences. Suitably, the library contains a minimum of four sequences, with at least two clades being represented. Preferably, the library contains at least two sequences from each of the represented clades. In one embodiment, the library contains more than 100 AAV sequences. In another embodiment, the library contains at least three to 100 AAV sequences. In still another embodiment, the library contains at least six to 50 AAV sequences.

Suitable AAVs for use in the functional libraries of the invention include, e.g., AAV1, AAV2, AAV6, AAV7, AAV8, AAV9, and other sequences which have been described [G. Gao, et al, *Proc Natl. Acad Sci.*, 100(10):6081-6086 (May 13, 2003); International Patent Publication Nos. WO 2004/042397 and WO 2005/033321]. One of skill in the art can readily select other AAVs, e.g., those isolated using the methods described in International Patent Publication No. WO 03/093460 A1 (Nov. 13, 2003) and US Patent Application Publication No. 2003-0138772 A1 (Jul. 24, 2003).

According to the present invention, the at least three sequences within the library are least 85% identical over the full-length of their aligned capsid sequences.

The term "percent (%) identity" may be readily determined for amino acid sequences, over the full-length of a protein, or a fragment thereof. Suitably, a fragment is at least about 8 amino acids in length, and may be up to about 700 amino acids. Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13):2682-2690 (1999).

Multiple sequence alignment programs are also available for nucleic acid sequences. Examples of such programs include, "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

According to the invention, the sequences of the target or parental AAV capsid suspected of containing a singleton are compared to the sequences of the AAV capsids within the library. This comparison is performed using an alignment of the full-length vp1 protein of the AAV capsid.

A singleton is identified where, for a selected amino acid position when the AAV sequences are aligned, all of the AAVs in the library have the same amino acid residue (i.e., are completely conserved), but the parental AAV has a different amino acid residue.

Typically, when an alignment is prepared based upon the AAV capsid vp1 protein, the alignment contains insertions and deletions which are so identified with respect to a reference AAV sequence (e.g., AAV2) and the numbering of the amino acid residues is based upon a reference scale provided for the alignment. However, any given AAV sequence may have fewer amino acid residues than the reference scale. In the present invention, when discussing the parental AAV and the sequences of the reference library, the term "the same position" or the "corresponding position" refers to the amino acid located at the same residue number in each of the sequences, with respect to the reference scale for the aligned sequences. However, when taken out of the alignment, each of the AAV vp1 proteins may have these amino acids located at different residue numbers.

Optionally, the method of the invention can be performed using a nucleic acid alignment and identifying as a singleton a codon which encodes a different amino acid (i.e., a non-synonymous codon). Where the nucleic acid sequences of a given codon are not identical in the parental AAV as compared to the sequences of that codon in the library, but encode the same amino acid, they are considered synonymous and are not a singleton.

According to the present invention, a parental AAV containing a singleton is altered such that the singleton residue is replaced with the conserved amino acid residue of the AAVs in the library.

Conveniently, this replacement can be performed by using conventional site-directed mutagenesis techniques on the codon for the variable amino acid. Typically, the site-directed mutagenesis is performed using as few steps as required to obtain the desired codon for the conserved amino acid residue. Such methods are well known to those of skill in the art and can be performed using published methods and/or commercially available kits [e.g., available from Stratagene and Promega]. The site-directed mutagenesis may be performed on the AAV genomic sequence. The AAV sequence may be carried by a vector (e.g., a plasmid backbone) for convenience. Alternatively, one of skill in the art can alter the parental AAV using other techniques know to those of skill in the art.

A parental AAV may have more than one singleton, e.g., two, three, four, five, six or more. However, improvement in function may be observed after correction of one singleton. In the embodiment where a parental AAV carries multiple singletons, each singleton may be altered at a time, followed by assessment of the modified AAV for enhancement of the desired function. Alternatively, multiple singletons may be altered prior to assessment for enhancement of the desired function.

Even where a parental AAV contains multiple singletons and functional improvement is observed altered of a first singleton, it may be desirable to optimize function by altering the remaining singleton(s).

Typically, a parental AAV which has had one or more singleton(s) altered according to the method of the invention, is assessed for function by packaging the AAV into an AAV particle. These methods are well known to those of skill in the art. See, e.g., G. Gao et al, Proc Natl Acad Sci., cited above; Sambrook et al, Molecular Cloning: A Laboratory Manual, Cold Spring Harbor Press, Cold Spring Harbor N.Y.

These altered AAVs have novel capsids produced according to the method of the invention and are assessed for function. Suitable methods for assessing AAV function have been described herein and include, e.g., the ability to produce DNAse protected particles, in vitro cell transduction efficiency, and/or in vivo gene transfer. Suitably, the altered AAVs of the invention have a sufficient number of singletons altered to increase function in one or all of these characteristics, as compared to the function of the parent AAV.

II. Novel AAV of the Invention

The invention further provides a method of predicting whether a novel AAV will be functional. The method involves using the singleton method of the invention and identifying the absence of a singleton in the sequence of the selected AAV, i.e., an AAV which lacks a singleton.

Thus, in one embodiment, the invention provides a method of selecting an AAV for use in producing a vector. This method involves selecting a parental AAV capsid sequence for analysis and identifying the absence of any singletons in the parental AAV capsid in an alignment comprising the parental AAV capsid sequence and a library of functional AAV capsid sequences. Once the absence of a singleton in a selected AAV capsid is determined, the AAV can be used to generate a vector according to known techniques.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity", "percent sequence identity", or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to about 99% of the aligned sequences and in certain embodiments, about 97% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "serotype" is a distinction with respect to an AAV having a capsid which is serologically distinct from other AAV serotypes. Serologic distinctiveness is determined on the basis of the lack of cross-reactivity between antibodies to the AAV as compared to other AAV. Cross-reactivity is typically measured in a neutralizing antibody assay. For this assay polyclonal serum is generated against a specific AAV in a rabbit or other suitable animal model using the adeno-associated viruses. In this assay, the serum generated against a specific AAV is then tested in its ability to neutralize either the same (homologous) or a heterologous AAV. The dilution that achieves 50% neutralization is considered the neutralizing antibody titer. If for two AAVs the quotient of the heterologous titer divided by the homologous titer is lower than 16 in a reciprocal manner, those two vectors are considered as the same serotype. Conversely, if the ratio of the heterologous titer over the homologous titer is 16 or more in a reciprocal manner the two AAVs are considered distinct serotypes.

In a further embodiment, the invention provides AAV having novel capsids, including rh. 20, rh.32/33, rh.39, rh.46, rh.73, and rh.74. The sequences of rh.20 have the amino acid sequence of SEQ ID NO:1, or a sequence 95 to 99% identical over the full-length of SEQ ID NO:1. The capsid of rh.32/33 has an amino acid sequence of SEQ ID NO:2, or sequences 95% to 99% identical thereto over the full-length of SEQ ID NO:2. The capsid of rh.39 has an amino acid sequence of SEQ ID NO:3, or sequences 95% to 99% identical thereto over the full-length of SEQ ID NO:3. The capsid of rh.46 has an amino acid sequence of SEQ ID NO:4, or sequences 95% to 99% identical thereto over the full-length of SEQ ID NO:4. The capsid of rh.73 has an amino acid sequence of SEQ ID NO:5, or sequences 95% to 99% identical thereto over the full-length of SEQ ID NO:5. The capsid of rh.74 has an amino acid sequence of SEQ ID NO:6, or sequences 95% to 99% identical thereto over the full-length of SEQ ID NO:6. Preferably, the sequence identity of these novel AAV capsids is such that it lacks any singletons. The sequences of the novel AAV are provided in the Sequence Listing.

In still another embodiment, the novel AAV sequences of the invention include the singleton-corrected AAV capsid proteins and the sequences encoding these capsid proteins. Examples of suitable singleton-correct AAV sequences include, AAV6.1, AAV6.2, AAV6.1.2, rh.8R, rh.48.1, rh.48.2, rh.48.1.2, hu.44R1, hu.44R2 hu.44R3, hu.29R, ch.5R1, rh.67, rh.54, hu.48R1, hu.48R2, and hu.48R3. For example, the singleton-corrected AAV6, including AAV6.1, AAV6.2 and AAV6.12 have shown significant functional improvement over the parental AAV6 sequence.

Particularly desirable proteins include the AAV capsid proteins, which are encoded by the nucleotide sequences identified above. The AAV capsid is composed of three proteins, vp1, vp2 and vp3, which are alternative splice variants. Other desirable fragments of the capsid protein include the constant and variable regions, located between hypervariable regions (HVR). Other desirable fragments of the capsid protein include the HVR themselves.

An algorithm developed to determine areas of sequence divergence in AAV2 has yielded 12 hypervariable regions (HVR) of which 5 overlap or are part of the four previously described variable regions. [Chiorini et al, J. Vivol, 73:1309-19 (1999); Rutledge et al, J. Virol., 72:309-319] Using this algorithm and/or the alignment techniques described herein, the HVR of the novel AAV serotypes are determined. For example, the HVR are located as follows: HVR1, aa 146-152; HVR2, aa 182-186; HVR3, aa 262-264; HVR4, aa 381-383; HVR5, aa 450-474; HVR6, aa 490-495; HVR7, aa 500-504; HVR8, aa 514-522; HVR9, aa 534-555; HVR10, aa 581-594; HVR11, aa 658-667; and HVR12, aa 705-719 [the numbering system is based on an alignment which uses the AAV2 vp1 as a point of reference]. Using the alignment provided herein performed using the Clustal X program at default settings, or using other commercially or publicly available alignment programs at default settings such as are described herein, one of skill in the art can readily determine corresponding fragments of the novel AAV capsids of the invention.

Suitably, fragments are at least 8 amino acids in length. However, fragments of other desired lengths may be readily utilized. Such fragments may be produced recombinantly or by other suitable means, e.g., by chemical synthesis.

The invention further provides other AAV sequences which are identified using the sequence information provided herein. For example, given the sequences provided herein, infectious may be isolated using genome walking technology (Siebert et al., 1995, Nucleic Acid Research, 23:1087-1088, Friezner-Degen et al., 1986, J. Biol. Chem. 261:6972-6985, BD Biosciences Clontech, Palo Alto, Calif.). Genome walking is particularly well suited for identifying and isolating the sequences adjacent to the novel sequences identified according to the method of the invention. This technique is also useful for isolating inverted terminal repeat (ITRs) of the novel AAV, based upon the novel AAV capsid and rep sequences provided herein.

The novel AAV amino acid sequences, peptides and proteins may be expressed from AAV nucleic acid sequences of the invention. Additionally, these amino acid sequences, peptides and proteins can be generated by other methods known in the art, including, e.g., by chemical synthesis, by other synthetic techniques, or by other methods. The sequences of any of the AAV capsids provided herein can be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well-known solid phase peptide synthesis methods (Merrifield, J. Am. Chem. Soc., 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

The sequences, proteins, and fragments of the invention may be produced by any suitable means, including recombinant production, chemical synthesis, or other synthetic means. Such production methods are within the knowledge of those of skill in the art and are not a limitation of the present invention.

III. Production of rAAV with Novel AAV Capsids

The invention encompasses novel AAV capsid sequences generated by mutation following use of the method of the invention for identifying singletons. The invention further encompasses the novel AAV rh.20, rh.32/33, rh.39, rh.46, rh.73, and rh.74 capsid sequences [SEQ ID Nos: 1-6].

In another aspect, the present invention provides molecules that utilize the novel AAV sequences of the invention, including fragments thereof, for production of viral vectors useful in delivery of a heterologous gene or other nucleic acid sequences to a target cell.

The molecules of the invention which contain AAV sequences include any genetic element (vector) which may be delivered to a host cell, e.g., naked DNA, a plasmid, phage, transposon, cosmid, episome, a protein in a non-viral delivery vehicle (e.g., a lipid-based carrier), virus, etc., which transfers the sequences carried thereon.

The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain, inter alia, sequences encoding an AAV capsid of the invention or a fragment thereof. In another embodiment, the vectors of the invention contain, at a minimum, sequences encoding an AAV rep protein or a fragment thereof. Optionally, vectors of the invention may contain both AAV cap and rep proteins. In vectors in which both AAV rep and cap are provided, the AAV rep and AAV cap sequences can originate from an AAV of the same clade. Alternatively, the present invention provides vectors in which the rep sequences are from an AAV source which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV source to form a chimeric AAV vector. Optionally, the vectors of the invention are vectors packaged in an AAV capsid of the invention. These vectors and other vectors described herein can further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV sequence. Alternatively, these vectors contain sequences encoding artificial capsids which contain one or more fragments of the singleton-corrected AAV capsid fused to heterologous AAV or non-AAV capsid proteins (or fragments thereof). These artificial capsid proteins are selected from non-contiguous portions of the singleton-corrected capsid or from capsids of other AAVs. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having a novel AAV capsid of the invention. Such a method involves culturing a host cell which contains a nucleic acid sequence encoding a novel AAV capsid protein of the invention, or fragment thereof, as defined herein; a functional rep gene; a minigene composed of, at a minimum, AAV inverted terminal repeats (ITRs) and a transgene; and sufficient helper functions to permit packaging of the minigene into the AAV capsid protein.

The components required to be cultured in the host cell to package an AAV minigene in an AAV capsid may be provided to the host cell in trans. Alternatively, one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.*, 70:520-532 (1993) and U.S. Pat. No. 5,478,745.

Unless otherwise specified, the AAV ITRs, and other selected AAV components described herein, may be readily selected from among any AAV, including, without limitation, AAV1, AAV2, AAV3, AAV4, AAV5, AAV6, AAV7, AAV9 and one of the other novel AAV sequences of the invention. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

A. The Minigene

The minigene is composed of, at a minimum, a transgene and its regulatory sequences, and 5' and 3' AAV inverted terminal repeats (ITRs). In one desirable embodiment, the ITRs of AAV serotype 2 are used. However, ITRs from other suitable sources may be selected. It is this minigene that is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), enhanced GFP (EGFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal Typically, suitable target sequences include oncologic targets and viral diseases. See, for examples of such targets the oncologic targets and viruses identified below in the section relating to immunogens.

The transgene may be used to correct or ameliorate gene deficiencies, which may include deficiencies in which normal genes are expressed at less than normal levels or deficiencies in which the functional gene product is not expressed. Alternatively, the transgene may provide a product to a cell which is not natively expressed in the cell type or in the host. A preferred type of transgene sequence encodes a therapeutic protein or polypeptide which is expressed in a host cell. The invention further includes using multiple transgenes. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Vivol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral *Rous sarcoma virus* (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Vivol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5' and 3' AAV ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3' AAV ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 µg to about 100 µg DNA, about 10 µg to about 50 µg DNA to about $1\times10^4$ cells to about $1\times10^{13}$ cells, or about $1\times10^5$ cells. However, the relative amounts of vector DNA to host cells may be adjusted by one of ordinary skill in the art, who may take into consideration such factors as the selected vector, the delivery method and the host cells selected.

B. Rep and Cap Sequences

In addition to the minigene, the host cell contains the sequences which drive expression of a novel AAV capsid protein of the invention (or a capsid protein comprising a fragment thereof) in the host cell and rep sequences of the same source as the source of the AAV ITRs found in the minigene, or a cross-complementing source. The AAV cap and rep sequences may be independently obtained from an AAV source as described above and may be introduced into the host cell in any manner known to one in the art as described above. Additionally, when pseudotyping an AAV vector, the sequences encoding each of the essential rep proteins may be supplied by different AAV sources (e.g., AAV1, AAV2, AAV3, AAV4, AAV5, AAV6, AAV7, AAV8, AAV9). For example, the rep78/68 sequences may be from AAV2, whereas the rep52/40 sequences may be from AAV8.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4 ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See International Patent Publication No. WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By "adenoviral DNA which expresses the E1a gene product", it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by other means, e.g., by exogenously added factors.

D. Host Cells and Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel singleton-corrected AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., CaPO4 transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

One of skill in the art will readily understand that the novel AAV sequences of the invention can be readily adapted for use in these and other viral vector systems for in vitro, ex vivo or in vivo gene delivery. Similarly, one of skill in the art can readily select other fragments of the AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

IV. Recombinant Viruses and Uses Therefor

Using the techniques described herein, one of skill in the art can generate a rAAV having a capsid of an AAV of the invention or having a capsid containing one or more fragments of an AAV of the invention. In one embodiment, a full-length capsid from a singleton-corrected AAV can be utilized.

A. Delivery of Viruses

In another aspect, the present invention provides a method for delivery of a transgene to a host which involves transfecting or infecting a selected host cell with a recombinant viral vector generated with the singleton-corrected AAV (or functional fragments thereof) of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences that direct expression thereof and the modified capsid proteins of the capsids.

Optionally, a sample from the host may be first assayed for the presence of antibodies to a selected AAV source (e.g., a serotype). A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W. C. Manning et al, *Human Gene Therapy*, 9:477-485 (Mar. 1, 1998). The results of this assay may be used to determine which AAV vector containing capsid proteins of a particular source are preferred for delivery, e.g., by the absence of neutralizing antibodies specific for that capsid source.

In one aspect of this method, the delivery of vector with AAV capsid proteins of the invention may precede or follow delivery of a gene via a vector with a different AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of sources (and preferably, different serotypes) which differ from the first vector. For example, if a first vector has a singleton-corrected capsid proteins, subsequently administered vectors may have capsid proteins selected from among the other AAV, optionally, from another serotype or from another clade.

Optionally, multiple rAAV vectors can be used to deliver large transgenes or multiple transgenes by co-administration of rAAV vectors concatamerize in vivo to form a single vector genome. In such an embodiment, a first AAV may carry an expression cassette which expresses a single transgene (or a subunit thereof) and a second AAV may carry an expression cassette which expresses a second transgene (or a different subunit) for co-expression in the host cell. A first AAV may carry an expression cassette which is a first piece of a polycistronic construct (e.g., a promoter and transgene, or subunit) and a second AAV may carry an expression cassette which is a second piece of a polycistronic construct (e.g., transgene or subunit and a polyA sequence). These two pieces of a polycistronic construct concatamerize in vivo to form a single vector genome that co-expresses the transgenes delivered by the first and second AAV. In such embodiments, the rAAV vector carrying the first expression cassette and the rAAV vector carrying the second expression cassette can be delivered in a single pharmaceutical composition. In other embodiments, the two or more rAAV vectors are delivered as separate pharmaceutical compositions which can be administered substantially simultaneously, or shortly before or after one another.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients.

For example, a therapeutically effective human dosage of the viral vector is generally in the range of from about 0.1 mL to about 100 mL of solution containing concentrations of from about $1\times10^9$ to $1\times10^{16}$ genomes virus vector. A preferred human dosage for delivery to large organs (e.g., liver, muscle, heart and lung) may be about $5\times10^{10}$ to $5\times10^{13}$ AAV genomes per 1 kg, at a volume of about 1 to 100 mL. A preferred dosage for delivery to eye is about $5\times10^9$ to $5\times10^{12}$ genome copies, at a volume of about 0.1 mL to 1 mL. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors α and β, interferons αa, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, Nature, 312:330 (1984); Vehar et al., Nature 312:337 (1984); and Toole et al, Nature, 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

As used herein, a therapeutically effective amount is an amount of AAV vector that produces sufficient amounts of Factor VIII to decrease the time it takes for a subject's blood to clot. Generally, severe hemophiliacs having less than 1% of normal levels of Factor VIII have a whole blood clotting time of greater than 60 minutes as compared to approximately 10 minutes for non-hemophiliacs.

The present invention is not limited to any specific Factor VIII sequence. Many natural and recombinant forms of Factor VIII have been isolated and generated. Examples of naturally occurring and recombinant forms of Factor VII can be found in the patent and scientific literature including, U.S. Pat. Nos. 5,563,045; 5,451,521; 5,422,260; 5,004,803; 4,757,006; 5,661,008; 5,789,203; 5,681,746; 5,595,886; 5,045,455; 5,668,108; 5,633,150; 5,693,499; 5,587,310; 5,171,844; 5,149,637; 5,112,950; 4,886,876; International Patent Publication Nos. WO 94/11503, WO 87/07144, WO 92/16557, WO 91/09122, WO 97/03195, WO 96/21035, and WO 91/07490; European Patent Application Nos. EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, and EP 0 160 457; Sanberg et al., XXth Int. Congress of the World Fed. Of Hemophilia (1992), and Lind et al., *Eur. J. Biochem.*, 232:19 (1995).

Nucleic acids sequences coding for the above-described Factor VIII can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, *Nature* 292:757 (1981); Nambari et al, *Science,* 223: 1299 (1984); and Jay et al, *J. Biol. Chem.* 259:6311 (1984).

Furthermore, the invention is not limited to human Factor VIII. Indeed, it is intended that the present invention encompass Factor VIII from animals other than humans, including but not limited to companion animals (e.g., canine, felines, and equines), livestock (e.g., bovines, caprines and ovines), laboratory animals, marine mammals, large cats, etc.

The AAV vectors may contain a nucleic acid coding for fragments of Factor VIII which is itself not biologically active, yet when administered into the subject improves or restores the blood clotting time. For example, as discussed above, the Factor VIII protein comprises two polypeptide chains, a heavy chain and a light chain separated by a B-domain which is cleaved during processing. As demonstrated by the present invention, co-tranducing recipient cells with the Factor VIII heavy and light chains leads to the expression of biologically active Factor VIII. Because most hemophiliacs contain a mutation or deletion in only one of the chains (e.g., heavy or light chain), it may be possible to administer only the chain defective in the patient to supply the other chain.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Suitably, the AAV vectors of the invention avoid the generation of immune responses to the AAV sequences contained within the vector. However, these vectors may nonetheless be formulated in a manner that permits the expression of a transgene carried by the vectors to induce an immune response to a selected antigen. For example, in order to promote an immune response, the transgene may be expressed from a constitutive promoter, the vector can be adjuvanted as described herein, and/or the vector can be put into degenerating tissue.

Examples of suitable immunogenic transgenes include those selected from a variety of viral families. Examples of desirable viral families against which an immune response would be desirable include, the picornavirus family, which includes the genera *rhinoviruses*, which are responsible for about 50% of cases of the common cold; the genera *enteroviruses*, which include polioviruses, coxsackieviruses, echoviruses, and human *enteroviruses* such as hepatitis A virus;

and the genera apthoviruses, which are responsible for foot and mouth diseases, primarily in non-human animals. Within the picornavirus family of viruses, target antigens include the VP1, VP2, VP3, VP4, and VPG. Other viral families include the astroviruses and the calcivirus family. The calcivirus family encompasses the Norwalk group of viruses, which are an important causative agent of epidemic gastroenteritis. Still another viral family desirable for use in targeting antigens for inducing immune responses in humans and non-human animals is the togavirus family, which includes the genera *alphavirus*, which include *Sindbis viruses, Ross River virus*, and Venezuelan, Eastern & Western Equine encephalitis, and rubivirus, including *Rubella virus*. The flaviviridae family includes dengue, yellow fever, Japanese encephalitis, St. Louis encephalitis and tick borne *encephalitis viruses*. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog), and human respiratory *coronaviruses*, which may cause the common cold and/or non-A, B or C hepatitis, and which include the putative cause of sudden acute respiratory syndrome (SARS). Within the coronavirus family, target antigensinclude the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the arterivirus family and the rhabdovirus family. The rhabdovirus family includes the genera *vesiculovirus* (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and *Ebola virus* may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera *bunyavirus* (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. Another source of antigens is the bornavirus family. The reovirus family includes the genera *reovirus, rotavirus* (which causes acute gastroenteritis in children), orbiviruses, and cultivirus (Colorado Tick fever, Lebombo (humans), equine encephalosis, blue tongue). The retrovirus family includes the sub-family oncorivirinal which encompasses such human and veterinary diseases as feline leukemia virus, HTLVI and HTLVII, lentivirinal (which includes HIV, simian immunodeficiency virus, feline immunodeficiency virus, equine infectious anemia virus, and spumavirinal).

With respect to HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. For example, suitable fragments of the envelope (env) protein include, e.g., gp41, gp140, and gp120. In addition, a variety of modifications to these and other HIV and SIV antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R. Amara, et al, Science, 292:69-74 (6 April 2001). These proteins or subunits thereof may be delivered alone, or in combination via separate vectors or from a single vector.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family includes feline parvovirus (feline enteritis), feline panleucopeniavirus, canine parvovirus, and porcine parvovirus. The herpesvirus family includes the sub-family alphaherpesvirinae, which encompasses the genera *simplexvirus* (HSVI, HSVII), *varicellovirus* (pseudorabies, varicella zoster) and the sub-family betaherpesvirinae, which includes the genera *cytomegalovirus* (HCMV, muromegalovirus) and the sub-family gammaherpesvirinae, which includes the genera *lymphocryptovirus*, EBV (Burkitts lymphoma), human herpesviruses 6A, 6B and 7, Kaposi's sarcoma-associated herpesvirus and cercopithecine herpesvirus (B virus), infectious rhinotracheitis, Marek's disease virus, and rhadinovirus. The poxvirus family includes the sub-family chordopoxvirinae, which encompasses the genera *orthopoxvirus* (Variola major (Smallpox) and Vaccinia (Cowpox)), *parapoxvirus, avipoxvirus, capripoxvirus, leporipoxvirus, suipoxvirus*, and the sub-family entomopoxvirinae. The hepadnavirus family includes the Hepatitis B virus. One unclassified virus which may be suitable source of antigens is the Hepatitis delta virus, Hepatitis E virus, and prions. Another virus which is a source of antigens is Nipan Virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative bacilli include enterobacteriaceae; *pseudomonas*, acinetobacteria and *eikenella; melioidosis; salmonella; shigella; haemophilus; moraxella; H. ducreyi* (which causes chancroid); *brucella* species (brucellosis); *Francisella tularensis* (which causes tularemia); *Yersinia pestis* (plague) and other *yersinia* (pasteurella); *streptobacillus moniliformis* and *spirillum*; Gram-positive bacilli include Listeria monocytogenes; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever (*Coxiella burnetti*), and Rickettsialpox. Examples of mycoplasma and chlamydial infections include: Mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or the toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of TCRs which are involved in the disease have been characterized. These TCRs include V-3, V-14, V-17 and V-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and V-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and V-16, V-3C, V-7, V-14, V-15, V-16, V-28 and V-12. Thus, delivery of a nucleic acid molecule that encodes at least one of these polypeptides will elicit an immune response that will target T cells involved in scleroderma.

Thus, a rAAV-derived recombinant viral vector of the invention provides an efficient gene transfer vehicle which can deliver a selected transgene to a selected host cell in vivo or ex vivo even where the organism has neutralizing antibodies to one or more AAV sources. In one embodiment, the rAAV and the cells are mixed ex vivo; the infected cells are cultured using conventional methodologies; and the transduced cells are re-infused into the patient.

These compositions are particularly well suited to gene delivery for therapeutic purposes and for immunization, including inducing protective immunity. AAV of the invention and compositions containing same can also be used in immunization regimens such as those described in co-owned U.S. patent application Ser. No. 60/565,936, filed Apr. 28, 2004 for "Sequential Adenovirus and AAV-Mediated Delivery of Immunogenic Molecules".

Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

Example 1

According to the method of the invention, AAV sequences have been identified as having singletons, when placed in an alignment with a library of sequences containing representatives of each of clades A, B, C, D, E, and F (represented by AAV9). The following table illustrates the capsid sequences and the singleton to be altered to a conserved sequence. For certain mutations, the singleton is followed by an * and then the amino acid reside which replaces it. For other mutations, the singleton is followed by its amino acid position and the residue which replaced it.

The amino acid numbering is based upon the published sequences for each of these AAV capsids. See, e.g., G. Gao, et al., *J. Virol.*, 78(12):6381-6388 (June 2004) and International Patent Publication No. WO 2004/042397 [all sequences therein deposited with GenBank], and International Patent Publication No. WO 2005/033321, filed Sep. 30, 2004, which are incorporated by reference.

For example, with reference to the following table, the nomenclature should be read as follow. Cy5R1 refers to the amino acid sequence of SEQ ID NO. 24, which has been modified to contain an aspartic acid (D) in amino acid residue position 13; cy5 has a glycine in its native amino acid sequence at residue number 13. Cy5R2 refers to the amino acid sequence of SEQ ID NO:24, which has been modified to contain an aspartic acid in amino acid position 13 (glycine in the native sequence) and an asparagine in amino acid residue position 403 (aspartic acid in the native sequence). Cy5R3 has the amino acid sequence of SEQ ID NO:24, which has been modified to have the same modifications as the Cy5R2 and, additionally, a lysine at position 158 (natively an asparagine) and a glutamine at position 161

(natively a proline). Given this information, one of skill in the art should be readily able to determine the other singleton modifications recited in the following table.

| Name | SEQ ID NO: (Parent AAV) | Sites Mutated | | | | Clade |
|---|---|---|---|---|---|---|
| cy5 | 24 | | | | | |
| Cy5R1 | | G13D | | | | D |
| Cy5R2 | | G13D | D403N | | | D |
| Cy5R3 | | G13D | D403N | R51K | | D |
| Cy5R4 | | G13D | D403N | R51K | N158K + P161Q | D |
| rh.13 | 26 | | | | | D |
| Rh.13R | | E538K | | | | D |
| Rh37 | 40 | | | | | D |
| Rh37R2 | | E634K | T207M | | | D |
| Rh.2 | 39 | | | | | E |
| rh.2R | | V651I | | | | E |
| Rh.8 | 41 | | | | | |
| rh.8R | | D531E | | | | |
| Rh.48 | 44 | | | | | |
| Rh.48.1 | | K217E | | | | B |
| Rh.48.2 | | S304N | | | | B |
| Rh.48.1.2 | | K217E | S304N | | | B |

| Name | SEQ ID NO: (Parent AAV) | Sites Mutated | | | Clade |
|---|---|---|---|---|---|
| Hu.44 | 45 | | | | A |
| Hu.44R1 | | E137K | | | A |
| Hu.44R2 | | E137K | P446L | | A |
| Hu.44R3 | | E137K | P446L | G609D | A |
| Rh32/33 | 2 | | | | |
| Hu. 29 | 42 | | | | B |
| Hu.29R | | G396E | | | B |
| Ch.5 | 46 | | | | |
| Ch.5R1 | | T611I | | | |
| rh.67 | 47 | | | | D |
| rh.58 | 48 | | S653N | | E |
| Rh.64 | 43 | | | | E |
| Rh64R1 | | R697W | | | E |
| Rh64R2 | | R697W | V686E | | E |
| AAV6 | 29 | | | | A |
| AAV6.2 | | F129L | | | A |
| AAV6.1 | | K531E | | | A |
| AAV6.12 | | F129L | K531E | | A |
| rh.54 | 49 | V404M | | | D |
| hu.48 | 50 | | | | A |
| hu.48R1 | | G277S | | | A |
| hu.48R2 | | G277S | E322K | | A |
| hu.48R3 | | G277S | E322K | S552N | A |

Example 2

In a preliminary study, five clones were selected to test the singleton method of the invention. The table below provides the phenotype description of the 5 clones. The number of predicted singletons is given with the clade and serotype classification.

Packaging phenotype is considered insufficient when their titer is lower than $1\times10^{11}$GC, low when lower than $1\times10^{12}$GC, good when lower $1\times10^{13}$, excellent when higher.

Gene transfer phenotypes were established by CB.A1AT gene expression and indicated as follows; "+++" better than lead candidate for target tissue, "++", "+" and "−" respectively better than 50%, between 10-50% or lower than 10% of A1AT serum levels of lead candidates (muscle: AAV1, Liver:AAV8, Lung:AAV9). "n/a" indicated that vector could not be produced at sufficient levels for in vivo gene transfer studies.

Cloning of the singleton corrections went as follows. From the original packaging plasmid, site directed mutagenesis was performed. Subsequent to that, vector backbone integrity was assayed by a PstI digest and correction of the singleton was confirmed by sequencing. EGFP-expressing vector was then produced in triplicates on 12-well format side by side with the parental singleton-containing vector, AAV2 and AAV2/8 positive control and a production without presence of packaging plasmid as a negative control. Equal volume of harvested lysate after a 3× freeze was incubated on 293 cells. eGFP expressing was monitored by flow cytometry 72 h post transduction.

Site-directed mutagenesis of the singleton residues in clones rh.37, rh.2, ch.5, rh.13, and rh.8 was performed. These particular sequences were selected to represent a variety of phenotypes that were previously documented.

| | Packaging | Gene Transfer Phenotype | | | | Clade |
|---|---|---|---|---|---|---|
| Clone | Phenotype | Lung | Liver | Muscle | # Singleton | (serotype) |
| rh.37 | insufficient | n/a | n/a | n/a | 2 | D (AAV7) |
| rh.2 | Low | ++ | + | +++ | 1 | E (AAV8) |
| ch.5 | Good | − | − | − | 1 | Ch.5 |
| rh.13 | Excellent | + | + | + | 1 | D (AAV7) |
| rh.8 | Good | − | + | ++ | 1 | Rh.8 |

An increase in vector expression was noticed for 4 out of 5 clones. The increase was most dramatic for rh.37 and rh.2, vectors that were previously shown to have a low packaging yield. For these vectors productive particles were produced at levels sufficient for detection. Vectors rh.8 and rh.13 showed an increase in transduction.

In order to distinguish the effects of the singleton mutation on transduction versus packaging and assembly, small-scale vector preparations were made and titered for Dnase resistant particles by quantitative PCR. For rh.37, a two-log increase in vector production was observed. rh.8 showed a moderate 5 fold increase in titer whereas rh.13 performed equally. All titers of singleton corrected clones were within acceptable range in comparison to AAV2 and AAV2/8 production and when extrapolated to large-scale preparations. rh.2 was not assayed for titration.

Subsequently the effect of the singleton change was monitored in vitro in a transduction setting with equal particle number per cell. A titration on 293 cells was performed for rh.8 and rh.13. Moderate increases in transduction efficiency were described at all MOIs.

From this initial subset of 5 clones, 3 productively transduced cells. Two clones were unable to yield any eGFP expression in this setting. This is most likely due to a defect in packaging of the vector that could not be predicted by the singleton approach.

The method of the invention was utilized to correct four predicted singleton locations in AAV clone hu. 46, P156S R362C S393F A676. However, these modifications did not result in an AAV which could be rescued, indicating another type of fatal error in the hu. 46 sequence.

Example 3—In Vitro Analysis of Viral Vectors with Altered Capsids

Using the methods of the invention, the capsid proteins of rh.64 and hu.29 were altered and then used to construct viral vectors with the altered capsids using pseudotyping as described in Example 2 and in G. Gao et al., Proc Natl Acad Sci USA 99, 11854-9 (Sep. 3, 2002).

Briefly, vectors expressing enhanced green fluorescent protein (EGFP) were used to examine in vitro transduction efficiency of the vectors in human endothelial kidney cells (293 cells). These 293 cells were incubated in the presence of $10^4$ GC/cell pseudotyped AAVCMVeGFP particles after a short pre-incubation with wtAd5. The number of eGFP positive cells per 10,000 total cells was measured by FACS analysis with a limit of detection of 5 cells/10 K.

Modification of the Rh.64 capsid according to the invention afforded modified rh.64 particles which were over a 100-fold more efficient after a R697W change. A subsequent V686E mutation yielded a 2-fold increase in packaging capability.

Modification of the Hu.29 capsid according to the invention afforded modified rh.64 virions that were rescued from a deficient packaging capability by changing G396E. A greater than 1000-fold increase in production was observed.

Many of the over 20 modified AAV virions showed improvement in expression include, AAV6.1, hu.48R1, hu.48R2, hu.44R2, hu.44R3, rh.48.2, rh.48.2, rh.48.2.1.

Example 4—Singleton effect in In Vivo Gene Transfer Applications

The effects of the singleton mutants were studied in an in vivo setting. Gene transfers studies on C57B/6 mice have been initiated on a number of vectors modified according to the method of the invention. Muscle directed and liver directed studies were initiated and benchmarked versus the current lead candidates for the particular application.

Human α-antitrypsin (A1AT) was selected as a sensitive and quantitative reporter gene in the vectors and expressed under the control of CMV-enhanced chicken β-actin promoter. Employment of the CB promoter enables high levels of tissue non-specific and constitutive A1AT gene transfer to be achieved and also permits use of the same vector preparation for gene transfer studies in any tissue of interest.

Muscle was chosen as a first target tissue. 40 different novel vectors (based on 24 different clones each with their respective singleton mutant(s)) were injected intramuscularly in a hind limb of C57B/6 mice. All experiments were performed with $1 \times 10^{11}$ GC/animal with a CB.A1AT transgene cassette. Vectors were each time aliquoted at equal volume (50 μl) per mouse and group per Clade. Every individual study comprised one or two clades with control groups including the representative serotype, AAV2/8 and AAV2/1 that served as benchmarks for muscle targeted gene transfer. Transgene expression is detected at day 7, 14, 28 and 63 post injection and evaluated by a specific hAlAT ELISA.

For several isolates and singleton corrected versions, data on their performance after intraportal liver-directed infusion was generated. Preliminary results show that the majority of the corrected clones perform equal or better than the original isolated.

For one particular clone namely cy.5, the singleton correction seem to beneficial effect on muscle transduction. The clone cy.5R4 carrying 4 singleton corrections improved gene transfer efficiency on an already decent muscle tropism exhibited by the original isolate. The performance of cy.5R4 is equal or slightly better than the benchmark controls AAV2/1 and AAV2/7.

An isolate that was previously yielded too low titers for further evaluation, rh.64, performed exceptionally well in muscle after correction of one singleton. Rh.64R1 performed better than rh64.2 and gave hAlAT levels higher than those achieved by its closest relative serotype AAV2/8 but also than AAV2/7.

In other studies, mice were injected with vector in groups based on the clades. $1 \times 10^{11}$ GC/mouse was dosed with vector expressing CB.hA1AT. Serum levels of hA1AT were measured by specific hA1AT ELISA.

The effects of singleton on in vivo gene transfer seem to be dependent on isolate and target tissue. Several interesting observations were made.

For certain singleton clones, the effects are qualitatively similar in muscle and liver (e.g. rh.2, rh.13 or cy.5). Isolates hu.48 and rh.48 show an increased expression in muscle with increased number of singletons reverted.

Other clones like rh.64 and AAV6 show a particular expression profile. Isolate hu.48R2 for example packages about 10 fold less efficient when compared to hu.48R3 but the latter transduces muscle about 5-fold less efficient. AAV6 contains two singletons. Both have moderate effects on packaging and combined they bring AAV6 packaging up to benchmark level. In vitro, little difference is noticeable between the parental clone and the different clones. In vivo, in muscle, AAV6.1 and AAV6.1.2 show decreased gene transfer whereas AAV6.2 show a moderate increase.

Example 5—Evaluation of Singleton-Corrected AAV in Lung and Liver

AAV vectors optimized for packaging and gene transfer efficiency by the reversion of singleton residues were further evaluated in lung and liver. The data is presented for both vectors that were identified as non-singleton containing or for those for which the singleton residue was converted to the conserved amino-acid.

A. Evaluation of CB.A1AT AAV gene transfer to lung after Intratracheal injection mediated by pi2, rh32.33, AAV2/9, AAV2/5, rh.2R, ch5R.

Several AAV capsids are compared in their ability to target lung. hA1AT levels were measured in serum. The AAVs evaluated are either singleton free (pi2, rh32.33, AAV2/9, AAV2/5, rh.2R, ch5R) or contain one singleton residue (rh.2, rh.8). AAV2/5 and AAV2/9 are represented as benchmarks.

The gene transfer studies were performed in C57B/6 mice (male, 5 per group) using the vectors carrying either the CB.A1 AT expression cassette (i.e., AAV2 5' ITR, chicken β-actin promoter (CB), human al-antitrypsin (A1AT), AAV2 3' ITR) or the CB.nLacZ expression cassette (i.e., AAV2, 5'ITR, nuclear-localized β-galactosidase (nLacZ), AAV2 3'ITR) in the capsids described above. Briefly, 50 μL of these singleton-corrected or singleton-free vectors were co-instilled ($1 \times 10^{11}$ genome copies (GC)) intratracheally with vectors carrying the A1AT and the vectors carrying the nLacZ ($1 \times 10^{11}$ GC).

At days 12 and 20, 20 bleeds were taken and serum levels of A1AT were measured (ng AAT/mL serum). The data showed a dramatic increase of human al-antitrypsin expression in lung for rh.2 to rh.2R after intratracheal (IT) injection of $1 \times 10^{11}$ GC. In addition a variety AAV vectors that are free of singleton residues were evaluated. All vectors showed acceptable levels of expression in lung.

B. Evaluation of AAV6 singleton vectors in comparison to the AAV2/5 and AAV2/9

AAV6 singleton corrected clones were evaluated. Modified AAV6 (AAV6.2) was prepared using the singleton correction method of the invention, and the pseudotyping techniques described herein. The AAV6.2 particles carrying A1AT and LacZ expression cassettes, prepared as described in Example 5, were coinjected intranasally ($1 \times 10^{11}$ GC) and intratracheally. AAT expression was evaluated by ELISA in serum and in bronchial alveolar liquid (BAL). Expression levels were normalized for total protein. LacZ expression was measured by ELISA for β-galactosidase from lung homogenate. Necropsy was performed at day 21.

These vectors were compared to AAV2/6, a current clinical candidate for lung gene transfer, AAV 2/5 and AAV2/9 in a study involving C57 Bl/6 mice (male, n=8/group).

AAV6.2 presented statistically significant improvement over AAV6 in serum A1AT excretion. AAV6.2 also showed higher levels of A1AT levels as compared to the other vectors, including AAV2/9 and AAV2/5. Mild improvement in BAL was noted as was for LacZ expression in lung homogenate. However, due to large animal to animal variations, no conclusions could be drawn from LacZ quantitation.

When evaluating the localization of AAV gene expression, superior staining for nuclear localized LacZ in the AAV2/6.2 group was observed, as compared to AAV 2/6. There was marked improvement over AAV2/6 and AAV2/5 in lung airway epithelium, the primary target for diseases like cystic fibrosis.

C. Intraportal (iv) injection of AAV.CB.A1AT ($1 \times 10^{11}$ GC) in C57Bl/6 mice with clade B and clade C AAV members.

All vectors used are absent of singleton residues either from isolation (AAV2/8, AAV2, hu.13, hu.51, hu.11, hu.53) or by mutation (hu.29R) All vectors are compared to AAV2/8 (clade E) as a benchmark.

D. *Intravenous injection of AAV members of Clade E.* rh. 64R1, rh. 64R2, rh.2R are singleton optimized. All other vector are singleton free.

The expression from AAV Clade B and C members was found similar to equivalent for all members including hu.29R, a singleton optimized clone. This particular clone was reconstituted in packaging capability from a hu.29 and now presents similar gene transfer functionality to other members of the virus family.

For Clade E vectors evaluated, all vectors that are either singleton free naturally or corrected for singleton residues perform in the similar range as the current best performer for liver directed gene transfer, AAV2/8. Particularly AAV rh64R1 and rh.64R2 are of interest. rh.64, found to be defective in packaging, now performs equally well in liver directed gene transfer after conversion of one (rh.64R1) or two (rh.64R2) singletons. For rh.2 the singleton correction corresponds to a dramatic more than 10 fold increase in gene delivery.

All publications, including patents, cited in this specification are incorporated herein by reference. While the invention has been described with reference to particularly preferred embodiments, it will be appreciated that modifications can be made without departing from the spirit of the invention.

The invention claimed is:

1. A recombinant adeno-associated virus (AAV) having an AAV capsid comprising Clade E vp1 capsid proteins having the amino acid sequence of 1 to 738 of SEQ ID NO:43 with a R697W modification or an amino acid sequence having at least 97% identity thereto, wherein residue 697 is W and wherein residue 686 is V, Clade E vp2 proteins and Clade E vp3 proteins, wherein said recombinant further comprises, packaged within the capsid, a nucleic acid molecule comprising at least one AAV inverted terminal repeat (ITR) and a non-AAV nucleic acid sequence encoding an enzyme operably linked to sequences which direct expression of the enzyme in a host cell.

2. The recombinant AAV of claim 1 in which the enzyme comprises ornithine transcarbamylase, arginosuccinate synthetase, arginosuccinate lyase, arginase, fumarylacetacetate hydrolase, carbamoyl phosphate synthetase I, branched chain ketoacid decarboxylase, isovaleryl-coA dehydrogenase, propionyl-CoA carboxylase, methylmalonyl-CoA mutase, glutaryl-CoA dehydrogenase (GCDH), pyruvate carboxylate, hepatic phosphorylase, phosphorylase kinase, or glycine decarboxylase.

3. The recombinant AAV of claim 1 or claim 2 in which the ITR is from AAV2.

4. A recombinant adeno-associated virus (AAV) comprising Clade E vp1 capsid proteins, Clade E vp2 capsid proteins having the amino acid sequence of 138 to 738 of SEQ ID NO:43 with a R697W modification or an amino acid sequence having at least 97% identity thereto, wherein residue 697 is W and wherein residue 686 is V and Clade E vp3 capsid proteins wherein said recombinant further comprises, packaged within the capsid, a nucleic acid molecule comprising at least one AAV inverted terminal repeat (ITR) and a non-AAV nucleic acid sequence encoding an enzyme operably linked to sequences which direct expression of the enzyme in a host cell.

5. The recombinant AAV of claim 4 in which the enzyme comprises ornithine transcarbamylase, arginosuccinate synthetase, arginosuccinate lyase, arginase, fumarylacetacetate hydrolase, carbamoyl phosphate synthetase I, branched chain ketoacid decarboxylase, isovaleryl-coA dehydrogenase, propionyl-CoA carboxylase, methylmalonyl-CoA mutase, glutaryl-CoA dehydrogenase (GCDH), pyruvate carboxylate, hepatic phosphorylase, phosphorylase kinase, or glycine decarboxylase.

6. The recombinant AAV of claim 4 or 5 in which the ITR is from AAV2.

7. A recombinant adeno-associated virus (AAV) comprising Clade E vp1 capsid proteins, Clade E vp2 capsid proteins and Clade E vp3 capsid proteins having the amino acid sequence of 204 to 738 of SEQ ID NO:43 with a R697W modification or an amino acid sequence having at least 97% identity thereto, wherein residue 697 is W and wherein residue 686 is V, wherein said recombinant further comprises, packaged within the capsid, a nucleic acid molecule comprising at least one AAV inverted terminal repeat (ITR) and a non-AAV nucleic acid sequence encoding an enzyme operably linked to sequences which direct expression of the enzyme in a host cell.

8. The recombinant AAV of claim 7 in which the enzyme comprises ornithine transcarbamylase, arginosuccinate synthetase, arginosuccinate lyase, arginase, fumarylacetacetate hydrolase, carbamoyl phosphate synthetase I, branched chain ketoacid decarboxylase, isovaleryl-coA dehydrogenase, propionyl-CoA carboxylase, methylmalonyl-CoA mutase, glutaryl-CoA dehydrogenase (GCDH), pyruvate carboxylate, hepatic phosphorylase, phosphorylase kinase, or glycine decarboxylase.

9. The recombinant AAV of claim 7 or 8 in which the ITR is from AAV2.

10. A recombinant adeno-associated virus (AAV) comprising Clade E vp1 capsid proteins having the amino acid sequence of 1 to 738 of SEQ ID NO:43 with a R697W modification or an amino acid sequence having at least 97% identity thereto, wherein residue 697 is W and wherein residue 686 is V, Clade E vp2 capsid proteins and Clade E vp3 capsid proteins wherein said recombinant further comprises, packaged within the capsid, a nucleic acid molecule comprising at least one AAV inverted terminal repeat (ITR) and a non-AAV nucleic acid sequence encoding an immunoglobulin operably linked to sequences which direct expression of the immunoglobulin protein in a host cell.

11. The recombinant AAV of claim 10 in which the immunoglobulin protein comprises IgG, IgM, IgA, IgD, IgE, a chimeric immunoglobulin, a humanized antibody, and/or a single chain antibody.

12. The recombinant AAV of claim 10 or 11 in which the ITR is from AAV2.

13. A recombinant adeno-associated virus (AAV) comprising Clade E vp1 capsid proteins, Clade E vp2 capsid proteins having the amino acid sequence of 138 to 738 of SEQ ID NO:43 with a R697W modification or an amino acid sequence having at least 97% identity thereto, wherein residue 697 is W and wherein residue 686 is V, and Clade E vp3 capsid proteins wherein said recombinant further comprises, packaged within the capsid, a nucleic acid molecule comprising at least one AAV inverted terminal repeat (ITR) and a non-AAV nucleic acid sequence encoding an immunoglobulin operably linked to sequences which direct expression of the immunoglobulin protein in a host cell.

14. The recombinant AAV of claim 13 in which the immunoglobulin protein comprises IgG, IgM, IgA, IgD, IgE, a chimeric immunoglobulin, a humanized antibody, and/or a single chain antibody.

15. The recombinant AAV of claim 13 or 14 in which the ITR is from AAV2.

16. A recombinant adeno-associated virus (AAV) comprising Clade E vp1 capsid proteins, Clade E vp2 capsid proteins and Clade E vp3 capsid proteins having the amino acid sequence of 204 to 738 of SEQ ID NO:43 with a R697W modification or an amino acid sequence having at least 97% identity thereto, wherein residue 697 is W and wherein residue 686 is V, wherein said recombinant further comprises, packaged within the capsid, a nucleic acid molecule comprising at least one AAV inverted terminal repeat (ITR) and a non-AAV nucleic acid sequence encoding an immunoglobulin operably linked to sequences which direct expression of the immunoglobulin protein in a host cell.

17. The recombinant AAV of claim 16 in which the immunoglobulin protein comprises IgG, IgM, IgA, IgD, IgE, a chimeric immunoglobulin, a humanized antibody, and/or a single chain antibody.

18. The recombinant AAV of claim 16 or 17 in which the ITR is from AAV2.

19. A recombinant adeno-associated virus (AAV) comprising Clade E vp1 capsid proteins having the amino acid sequence of 1 to 738 of SEQ ID NO:43 with a R697W modification or an amino acid sequence having at least 97% identity thereto, wherein residue 697 is W and wherein residue 686 is V, Clade E vp2 capsid proteins and Clade E vp3 capsid proteins wherein said recombinant further comprises, packaged within the capsid, a nucleic acid molecule comprising at least one AAV inverted terminal repeat (ITR) and a non-AAV nucleic acid sequence encoding a blood clotting factor operably linked to sequences which direct expression of the blood clotting factor in a host cell.

20. The recombinant AAV of claim 19, wherein the protein useful for the blood clotting factor is Factor IX, Factor VIII, or variants thereof.

21. The recombinant AAV of claim 19 or 20, wherein the ITR is from AAV2.

22. A recombinant adeno-associated virus (AAV) comprising Clade E vp1 capsid proteins, Clade E vp2 capsid proteins having the amino acid sequence of 138 to 738 of SEQ ID NO:43 with a R697W modification or an amino acid sequence having at least 97% identity thereto, wherein residue 697 is W and wherein residue 686 is V, and Clade E vp3 capsid proteins wherein said recombinant further comprises, packaged within the capsid, a nucleic acid molecule comprising at least one AAV inverted terminal repeat (ITR) and a non-AAV nucleic acid sequence encoding a blood clotting factor operably linked to sequences which direct expression of the blood clotting factor in a host cell.

23. The recombinant AAV of claim 22, wherein the blood clotting factor is Factor IX, Factor VIII, or variants thereof.

24. The recombinant AAV of claim 22 or 23 in which the ITR is from AAV2.

25. A recombinant adeno-associated virus (AAV) comprising Clade E vp1 capsid proteins, Clade E vp2 capsid proteins and Clade E vp3 capsid proteins having the amino acid sequence of 204 to 738 of SEQ ID NO:43 with a R697W modification or an amino acid sequence having at least 97% identity thereto, wherein residue 697 is W and wherein residue 686 is V, and wherein said recombinant further comprises, packaged within the capsid, a nucleic acid molecule comprising at least one AAV inverted terminal repeat (ITR) and a non-AAV nucleic acid sequence encoding a blood clotting factor operably linked to sequences which direct expression of the blood clotting factor in a host cell.

26. The recombinant AAV of claim 25, wherein the blood clotting factor is Factor IX, Factor VIII, or variants thereof.

27. The recombinant AAV of claim 25 or 26, wherein the ITR is from AAV2.

* * * * *